(12) United States Patent
Haeuw

(10) Patent No.: US 8,697,855 B2
(45) Date of Patent: Apr. 15, 2014

(54) ANTI-CD151 ANTIBODIES AND THEIR USE IN THE TREATMENT OF CANCER

(75) Inventor: Jean-François Haeuw, Beaumont (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 0 days.

(21) Appl. No.: 13/440,259

(22) Filed: Apr. 5, 2012

(65) Prior Publication Data

US 2012/0284810 A1 Nov. 8, 2012

Related U.S. Application Data

(62) Division of application No. 12/576,824, filed as application No. PCT/FR2009/050612 on Apr. 8, 2009, now Pat. No. 8,232,372.

(30) Foreign Application Priority Data

Apr. 11, 2008 (FR) ...................................... 08 01985

(51) Int. Cl.
*C07H 21/00* (2006.01)

(52) U.S. Cl.
USPC ...................................................... 536/23.53

(58) Field of Classification Search
None
See application file for complete search history.

(56) References Cited

U.S. PATENT DOCUMENTS

2007/0054278 A1* 3/2007 Cargill .............................. 435/6
2008/0003605 A1* 1/2008 Weigert et al. .................... 435/6

* cited by examiner

*Primary Examiner* — Brad Duffy
(74) *Attorney, Agent, or Firm* — Finnegan

(57) ABSTRACT

The present invention relates to new antibodies capable of binding specifically to the human CD151 protein, especially monoclonal antibodies of murine origin, which are chimeric and humanized, and also to the amino acid and nucleic sequences coding for those antibodies. The invention also includes use of those antibodies as medicaments for the prophylactic and/or therapeutic treatment of cancers and in diagnostic methods or kits for diseases associated with overexpression of the CD151 protein. Finally, the invention includes products and/or compositions comprising such antibodies in association with antibodies and/or anti-cancer agents or conjugated with toxins and/or radioelements and their use in the prevention and/or treatment of certain cancers.

16 Claims, 33 Drawing Sheets
(19 of 33 Drawing Sheet(s) Filed in Color)

CD 151

- Nucleotide sequence atgggtgagt tcaacgagaa gaagacaaca tgtggcaccg tttgcctcaa gtacctgctg
tttacctaca attgctgctt ctggctggct ggctggctg tcatggcagt gggcatctgg
acgctggccc tcaagagtga ctacatcagc ctgctggct caggcaccta ctggccaca
gctacatcc tggtggtggc gggcactgtc gtcatggtga ctgggtctt ggctgctgc
gccacctca aggagctcg gaacctgctg cgctgtact tcatcctgct cctcatcatc
ttctgtgg agatcatcgc tggtatcctc gctacgcct actaccagca gctgaacacg
gagctcaagg agaacctgaa ggacaccatg accaXbcgct accaccagXc gggccatgag
gctgtgacca gcgctgtgga ccagctgcag caggagttcc actgctgtgg cagcaacaac
tcacaggact ggcgagacag tgagtggatc cgctcacagg aggccggtgg ccgtgtggtc
ccagacagct gctgcaagac ggtggtggct ctttgtgggc agcgagacca tgcctccaac
atctacaagg tggagggcgg ctgcatcacc aagttggaga ccttcatcca ggagcacctg
aXXgtcattg gggctgtggg gatcggcatt gcctgtgtgc aggtctttgg catgatcttc
agtgctgcc tgtacaggag tctcaagctg gagcactac

- Protein sequence (1 letter code)

MGEFNEKTT CGTVCLKYLL FTYNCCWLA GLAVMAVGIW TLALKSDYIS
LIASGTYLAT AYILVVAGTV VMVTGVLGCC ATKERRNLL RLYFILLLII
FLLEIIAGIL AYYQQLNT ELKENLKDTM XRYHQXHE AVTSAVDQLQ
QEFHCCGSNN SQDWRDSEWI RSQEAGGRVV PDSCCKTVVA LCGQRDHASN
IYKVEGGCIT KLETFIQEHL RVIGAVGIGI ACVQVFGMIF TCCLYRSLKL
EHY

Figure 1

ANTIBODY 203B6

Variable domain of the heavy chain (VH)

- *Nucleotide sequence*

GAAGTGAAGCTGGTGGAGTCTGGGGGAGGTTTAGTGCAGCCTGGAGGGTCCCTGAAACTCTC
CTGTGCAGCCTCTGGATTCACTTTCAGTACCTATACCATGTCTTGGGTTCGCCAGACTCCAG
                     CDR-H1
AGAAGAGGCTGGAGTGGGTCGCA TACATTAGTAGTGGTGGTGGTACTACCTATTATGCAGAC
                                     CDR-H2
ACTGTAAAGGC CGATTCACCATCTCCAGAGACAATGCAGGAACATCCTGTACCTGCAAAT
GAACAGTCTGAAGTCTGAGGACACGGCCATGTATTACTGTGCAACTCCCCGAATTGGGACGG
                                                          CDR-H3
GGTTTGCTTACTGGGGCCAAGGGACTCTGGTCACTGTCTCTGCT

- *Protein sequence (1 letter code)*

EVKLVESGGGLVQPGGSLKLSCAASGFTFSTYTMSWVRQTPEKRLEWVAISSGGGTTYYP
                              CDR-H1                                   CDR-H2
TYKGRFTISRDNARNTLYLQMNSLKSEDTAMYYC ATPRIGTGFAYWGQGTLVTVSA
                                                               CDR-H3

Variable domain of the light chain (VL)

- *Nucleotide sequence*

GACATTGTGCTCAGCCAATCTCCAGCTTCTTTGGCTCTGTCTCTGGGGCAGAGAGCCACCAT
CTCCTGCAGAGCCAGTGCCAGTGTTGAATATTATGGCACAAGTTTAATGCATTGGTACCAAC
                                      CDR-L1
AGAAACCAGGACAGCCACCTAAACTCCTCATCTATGAAGCATCCAATGTAGAATCTGGGGTC
                                                      CDR-L2
CCTGCCAGGTTTAGTGGCAGTGGGTCTGGGACAGACTTCAGCCTCAACATCCATCCTGTGGA
GGAGGATGATCTTGCAATATATTTCTGTCAGCAAAGTAGGAAGGCTCCTTACACGTTCGGAG
                                                      CDR-L3
GGGGACCAAGCTGGAAATAAAA

- *Protein sequence (1 letter code)*

DIVLSQSPASLALSLGQRATISC RASASVEYYGTSLMHWYQQKPGQPPRLLIYEASNVES GV
                                    CDR-L1                                              CDR-L2
PARFSGSGSGTDFSLNIHPVEEDDLAIYFCQQSRKAPYTFGGGTKLEIK
                                CDR-L3

Figure 3

ANTIBODY 205H8

Variable domain of the heavy chain (VH)

- *Nucleotide sequence*

CAGGTTACTCTGAAAGAGTCTGGCCCTGGGATATTGCAGCCCTCCCAGACCCTCAGTCTGAC

TTGTTCTTTCTCTGGTTTTACACTCAGTACTTCTGGTATGGGTGTGAGCTGGATTCGTCAGC
                              CDR-H1

CTTCAGGAAAGGGTCTGGAGTGGCTGGCATACATTTACTGGGATGATGACAAGCGTTATAAC
                                        CDR-H2

CCATCCCTGAAGAGCCGGCTCACAATCTCCAAGGATACCTCCAGAAACCAGGTATTCCTCAA

GATCACCAGTGTGGACACTGCAGATACTGCCACATACTACTGTGCTCGAAGAGACCACTATG
                                                  CDR-H3

GTGACTACTCCTATGCTATGGACTACTGGGGTCAAGGAACCTCAGTCACCGTCTCCTCA

- *Protein sequence (1 letter code)*

QVTLKESGPGILQPSQTLSLTCSFSGFTLSTSGMGVSWIRQPSGKGLEWLAIYWDDDKRYN
                        CDR-H1                             CDR-H2

PSLKSRLTISKDTSRNQVFLKITSVDTADTATYYCARRDHYGDYSYAMDYWGQGTSVTVSS
                                                CDR-H3

Variable domain of the light chain (VL)

- *Nucleotide sequence*

GACATTGTGATGACCCAGTCTCAAAAATTCATGTCCACATCAGAAGGAGACAGGGTCAGCAT

CACCTGCAAGGCCAGTCAGAATGTGGGTATTGCTGTAGCCTGGTATCAACAGAAACCAGGAC
                      CDR-L1

AATCTCCTAAACTACTGATTTACTCGGCATCCAATCGCTACACTGGAGTCCCTGATCGCTTC
                            CDR-L2

ACAGGCAGTGGATCTGGGACAGATTTCACTCTCACCATCAGCAATATGCAGTCTGAAGACCT

GGCAGATTATTTCTGCCAGCAATATAGCAGCAATCCCACGTTCGGTGCTGGGACCAAGTTGG
                       CDR-L3

AGCTGAAA

- *Protein sequence (1 letter code)*

DIVMTQSQKFMSTSEGDRVSITCKASQNVGIAVAWYQQKPGQSPKLLIYSASNRYTSVPDRF
                            CDR-L1                              CDR-L2

TGSGSGTDFTLTISNMQSEDLADYFCQQYSSNPTFGAGTKLELK
                                   CDR-L3

Figure 4

ANTIBODY 211F3

Variable domain of the heavy chain (VH)

*- Nucleotide sequence*

GAAGTGAAGCTGGTGGAGTCTGGGGGAGATTTAGTGCAGCCTGGAGGGTCCTTGAAACTCTC
CTGTGCAGCCTCTGGATTCACTTTCAGTACCTATACCATGTCTTGGGTTCGCCAGACTCCAG
                            CDR-H1
AGAAGAGGCTGGAGTGGGTCGCA<u>TACATTAGTAGTGGTGGTGTTACTACCTACTATCCAGAC</u>
                                                      CDR-H2
ACTATAAGGGCCGATTCACCATCTCCAGAGACAATGCCAAGAACACCCTGTTCCTGCAAAT
GAACAGTCTGAAGTCTGAAGACACGGCCATGTATTACTGTACAAGCCCCCGAACTGGGACGG
                                                                      CDR-H3
GGTTTGCTTACTGGGGCCAAGGGACTCTGGTCACTGTCTCTGCT

*- Protein sequence (1 letter code)*

EVKLVESGGDLVQPGGSLKLSCAASGFTFSTYTMSWVRQTPEKRLEWVAISSGGVTTYYPD
                        CDR-H1                                          CDR-H2
YIKGRFTISRDNAKNTLFLQMNSLKSEDTAMYYCTSPRTGTGFAYWGQGTLVTVSA
                                                      CDR-H3

Variable domain of the light chain (VL)

*- Nucleotide sequence*

GACATTGTGCTCACCCAATCTCCAGCTTCTTTGGCTCTGTCTCTGGGGCAGAGAGCCACCAT
CTCCTGCAGAGCCAGTGCAAGTGTTGATTATTATGGCACAAGTTTAATGCAGTGGTACCAAC
                                     CDR-L1
AGAAACCAGGACAGCCACCCAAACTCCTCATCTATGAAGCATCCAACGTAGAATCTGGGGTC
                                                        CDR-L2
CCTGCCAGGTTTAGTGGCAGTGGGTCTGGGACAGACTTCAGCCTCAACATCCATCCTGTGGA
GGAGGATGATCTTGCAATATATTTCTGTCAGCAAAGTAGGAAGGCTCCTTACACGTTCGGAG
                                                            CDR-L3
GGGGGACCAAGCTGGAAATAAAA

*- Protein sequence (1 letter code)*

DIVLTQSPASLALSLGQRATISCRASASVDYYGTSLMQWYQQKPGQPPKLLIYEASNVESGV
                               CDR-L1                                    CDR-L2
PARFSGSGSGTDFSLNIHPVEEDDLAIYFCQQSRKAPYTFGGGTKLEIK
                                     CDR-L3

Figure 5

ANTIBODY 214B2

Variable domain of the heavy chain (VH)

- *Nucleotide sequence*

CAGGTCCAACTGCAGCAGCCTGGGTCTGTGCTGGTGAGGCCTGGAGCTTCAGTGAAGCTGTC
CTGCAAGGCTTCTGGCTACACCTTCACCAGCTCCTCGATGCACTGGGCGAAGCAGAGGCCTG
              CDR-H1
GACAAGGCCTTGAGTGGATCGGAGAGATTCATCCTAATAGTGGTAATACTAACAACAATGAG
                          CDR-H2
AAGTTCAAGGGCAAGGCCACACTGACTGTAGACACATCCTCCAGCACAGCCTACGTGGATCT
CAGCAGCCTGTCATCTGAGGACTCTGCGGTCTATTACTGTGCAAGGGCGAGGTCCTTTTACT
                                                CDR-H3
ATGCTATGGACTGCTGGGGTCAAGGAACCTCAGTCACCGTCTCCTCA

- *Protein sequence (1 letter code)*

QVQLQQPGSVLVRPGASVKLSCKASGYTFTSSSMHWAKQRPGQGLEWIGEIHPNSGNTNNNE
                      CDR-H1                            CDR-H2
KFKGKATLTVDTSSSTAYVDLSSLSSEDSAVYYCARARSFYYAMDCWGQGTSVTVSS
                                              CDR-H3

Variable domain of the light chain (VL)

- *Nucleotide sequence*

AACATTGTAATGACCCAATCTCCCAAATCCATGTCCATGTCAGTAGGAGAGAGGGTCACCTT
GAGCTGCAAGGCCAGTGAGAATGTGGGTACTTATGTATCCTGGTATCAACAGAAACCAGAGC
                     CDR-L1
AGTCTCCTAAACTACTAATATACGGGGCATCCAACCGGTACACTGGGGTCCCCGATCGCTTC
                              CDR-L2
ACAGGCAGTGGGTCTGCAACAGATTTCACACTGACCATCAGCAGTGTGCAGGCTGAAGACCT
TGCAGACTATCACTGTGGACAGACTTACAGCTTTCCGTACACGTTCGGAGGGGGGACCAAGC
                        CDR-L3
TGGAAATAAAA

- *Protein sequence (1 letter code)*

NIVMTQSPKSMSMSVGERVTLSCKASENVGTYVSWYQQKPEQSPRLLIYGASNRYTGVPDRF
                          CDR-L1                              CDR-L2
TGSGSATDFTLTISSVQAEDLADYHCGQTYSFPYTFGGGTKLEIK
                              CDR-L3

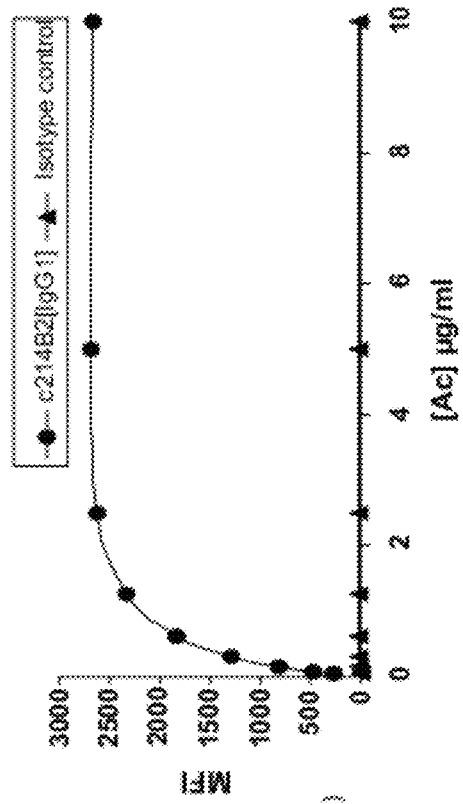
Figure 27A
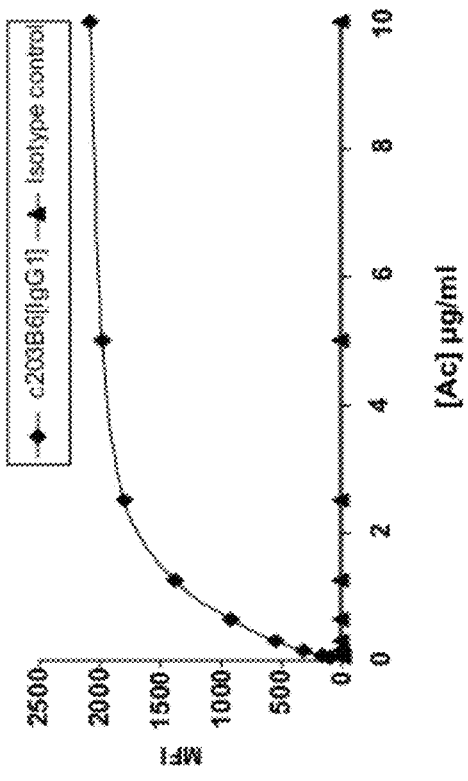
Figure 27B
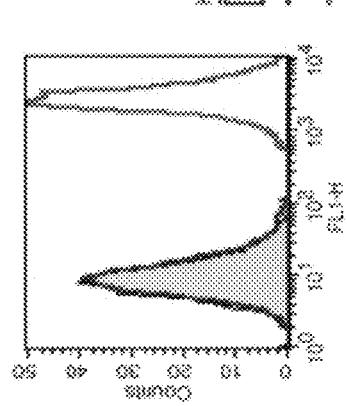
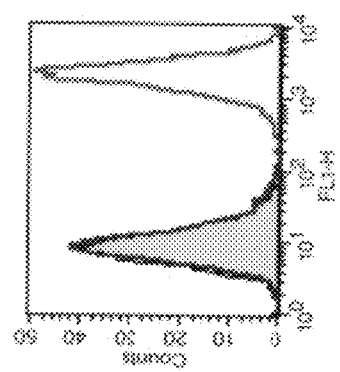

ANTI-CD151 ANTIBODIES AND THEIR USE IN THE TREATMENT OF CANCER

This application is a division of U.S. application Ser. No. 12/515,915, filed Sep. 17, 2009, now U.S. Pat. No. 8,232,372, which is the national stage filing under 35 U.S.C. §371 of International PCT/FR2009/050612, filed on Apr. 8, 2009, and claims the priority of French Application No. 0801985, filed on Apr. 11, 2008, the content of both of which is incorporated herein by reference.

The present invention relates to new antibodies, especially monoclonal antibodies of murine origin, which are chimeric and humanized, and which are capable of inhibiting tumour growth, and also to the amino acid and nucleic sequences coding for those antibodies. According to a particular aspect, the invention relates to new antibodies, derivative compounds or functional fragments, which are capable of inhibiting the proliferation of tumour cells. The invention also includes use of those antibodies as medicaments for the prophylactic and/or therapeutic treatment of cancers and also in cancer diagnostic methods or kits. Finally, the invention includes products and/or compositions comprising such antibodies in association, for example, with anti-cancer agents and/or antibodies or conjugated with toxins, and use thereof in the prevention and/or treatment of certain cancers.

CD151, also referred to as PETA-3 or SFA-1, is a membrane protein belonging to the tetraspanin family (Boucheix and Rubinstein, 2001, Cell Mol. Life. Sci. 58, 1189-1205; Hemler, 2001, J. Cell Biol. 155, 1103-1107). In humans, CD151 has 253 amino acids and includes 4 membrane fragments and 2 extracellular domains EC1 (18 amino acids, sequence [40-57]) and EC2 (109 amino acids, sequence [113-221]) which are also referred to as extracellular loops. It is to be noted, however, that, in the nucleotide sequence, two variants of CD151 have been identified hitherto, namely one having nucleotides A and C at positions 395 and 409, respectively, [Fitter et al., 1995, Blood 86(4), 1348-1355] and the other having, at the same positions, nucleotides G and T instead of nucleotides A and C [Hasegawa et al., 1996, J. Virol. 70(5), 3258-3263]. As a result, a mutation can be observed in the peptide sequence, namely a mutation of the residues K (Lys) and P (Pro) at positions 132 and 137, respectively, to the residues R (Arg) and S (Ser) [Fitter et al., 1995, Blood 86(4), 1348-1355/Hasegawa et al., 1996, J. Virol. 70(5), 3258-3263].

CD151 is overexpressed in numerous cancers such as, for example, cancers of the lung [Tokuhara et al., 2001, Clin. Cancer Res. 7, 4109-4114], colon [Hashida et al., 2003, Br. J. Cancer 89, 158-167], prostate [Ang et al., 2004, Cancer Epidemiol. Biomarkers Prev. 13, 1717-1721] or pancreas [Gesierich et al., 2005, Clin. Cancer Res. 11, 2840-2852].

The use of knock-out mice which do not express CD151 and of anti-CD151 antibodies and siRNA in order to block, in vitro, the functionality and expression of CD151 in various types of cell has allowed it to be shown that CD151 is involved in a number of phenomena related to cancer, such as cell adhesion (Nishiuchi et al., 2005, Proc. Natl. Acad. Sci. USA 102, 1939-1944; Winterwood et al., 2006, Mol. Biol. Cell 17, 2707-2721), cell motility (Kohno et al., 2002, Int. J. Cancer 97, 336-343), cell migration (Yauch et al., 1998, Mol. Biol. Cell 9, 2751-2765; Testa et al., 1999, Cancer Res. 59, 3812-3820; Penas et al., 2000, J. Invest. Dermatol. 114, 1126-1135; Klosek et al., 2005, Biochem. Biophys. Res. Commun. 336, 408-416), cell invasion (Kohno et al., 2002, Int. J. Cancer 97, 336-343; Shiomi et al., 2005, Lab. Invest. 85, 1489-1506; Hong et al., 2006, J. Biol. Chem. 281, 24279-24292) and angiogenesis (Yanez-Mo et al., 1998, J. Cell Biol. 141, 791-804; Sincock et al., 1999, J. Cell Sci. 112, 833-844; Takeda et al., 2007, Blood 109, 1524-1532).

One of the noteworthy properties of the tetraspanins is their ability to form associations amongst themselves and also with a large number of other surface molecules so as to form structured macromolecular complexes. Within those complexes, each tetraspanin is associated specifically with one or more surface molecules, thereby forming primary complexes composed of a tetraspanin and a partner molecule. The tetraspanins are capable of organising particular microdomains of the plasma membrane from which microdomains they may recruit their partner molecules, which may be functionally coupled. The set of interactions involving the tetraspanins has been referred to as the "network of tetraspanins" or "Tetraspanin Web".

CD151 interacts on the surface of cells with various membrane proteins. In particular, there have been identified highly stable complexes, resistant to the action of certain detergents, with laminin receptor integrins, more particularly with the integrins α3β1 or α6β4, whose preferred ligand is laminin 5 (Yauch et al., 1998, Mol. Biol. Cell 9, 2751-2765; Lammerding et al., 2003, Proc. Natl. Acad. Sci. USA 100, 7616-7621). This association involves the extracellular domains of CD151 and the integrins. The sequence QRD [194-196] of CD151, located in the EC2 loop, is very important in that association because mutation of this site causes loss of interaction with certain integrins (Kazarov et al., 2002, J. Cell Biol. 158, 1299-1309). Functional ternary complexes of CD151/integrin α6β4/c-Met (HGF receptor) have moreover been identified in tumour cells (Klosek et al., 2005, Biochem. Biophys. Res. Commun. 336, 408-416). Inhibition of the expression of CD151 as a result of treating cells with an interference RNA results in inhibition of the cell growth and migration caused by HGF.

The interactions, within a particular cell, between CD151 and other tetraspanins, necessary for formation of the network of tetraspanins, are thought to depend on the membrane and cytoplasmic regions of CD151 because it has been shown that deletion of the EC2 loop does not disrupt the association of CD151 with other tetraspanins (Berditchevski, 2001, J. Cell Sci. 114, 4143-4151).

CD151 is capable of regulating the phenomena of cell adhesion, migration and invasion by modulation of various signalling pathways such as, for example, the phosphoinositide pathway via an association with PI4-kinase (Yauch et al., 1998, Mol. Biol. Cell 9, 2751-2765), the c-Jun signalling pathway via the phosphorylation of FAK, Src, p38-MAPK and JNK (Hong et al., 2006, J. Biol. Chem. 281, 24279-24292), the phosphorylation of integrins by PKC (Zhang et al., 2001, J. Biol. Chem. 276, 25005-25013) and the activation of GTPases of the Rho family (Shigeta et al., 2003, J. Cell Biol. 163, 165-176).

Homophilic-type interactions between cells are also responsible for an increase in cell motility and in expression of the metalloproteinase MMP-9 (Hong et al., 2006, J. Biol. Chem. 281, 24279-24292). Those intercellular CD151-CD151 interactions bring about the activation of c-Jun via the phosphorylation of FAK, Src, p38-MAPK and JNK.

Despite the interest in the CD151 protein, two therapeutically aimed antibodies have been generated to date, namely the monoclonal antibodies 50-6 and SFA1.2B4. These 2 antibodies have comparable activities. Although they do inhibit the formation of metastases in vivo in animal models, no effect on tumour growth in vivo has been established.

The monoclonal antibody 50-6 (IgG1 isotype) directed to CD151 was generated in the mouse by subtractive immunizations with human epidermoid carcinoma HEp-3 cells (Testa et al., 1999, Cancer Res. 59, 3812-3820).

The antibody 50-6 is capable of inhibiting, in vitro, migration of human cervical carcinoma HeLa cells, transfected so as to overexpress CD151, and of HEp-3 cells and angiogenesis in a model of chorio-allantoic membrane neovascularisation caused by bFGF (basic fibroblast growth factor). In vivo it inhibits the metastases brought about by inoculation of HEp-3 cells in 2 chicken embryo models (Testa et al., 1999, Cancer Res. 59, 3812-3820). In these models, the inhibitory activity of the antibody 50-6 is determined by measurement of the activity of the protein huPA (human urokinase-type plasminogen activator) in lung extracts. According to the authors, this assay reflects the presence of human cells in the lungs. After assaying, the reduction in metastases (dissemination of HEp-3 cells into the chicken embryo lungs) that is brought about by the antibody 50-6 is estimated, by comparison with a control antibody, to be 74% in a so-called "spontaneous metastasis" model, in which inoculation of the cells is followed by injection of the antibody, and 57% in a so-called "experimental metastasis" model, in which the cells and the antibody are inoculated together. According to the authors, the anti-tumour properties of the antibody 50-6 that are observed in vivo do not seem to be related to a cytostatic or cytotoxic effect because the antibody showed no effect on the in vitro proliferation of HEp-3 cells.

The hybridoma producing the antibody 50-6 is available at the ATCC under the reference CRL-2696 (hybridoma initially deposited under the reference 50-6 [PTA-227]).

The anti-CD151 monoclonal antibody SFA 1.2B4 (IgG1 isotype) was generated in the mouse after immunisation by the intraperitoneal route with NIH 3T3 cells transfected by the human CD151 gene (Hasegawa et al., 1996, J. Virol. 70, 3258-3263). The antibody SFA1.2B4 is capable of inhibiting in vitro cell invasion and motility of various human tumour lines (Kohno et al., 2002, Int. J. Cancer 97, 336-343). It inhibits in vivo the pulmonary metastases caused by colon cancer RPMI14788 and fibrosarcoma HT1080 lines transfected so as to overexpress CD151 (Kohno et al., 2002, Int. J. Cancer 97, 336-343).

Other murine anti-CD151 antibodies have been described in the literature, such as, for example, the monoclonal antibodies 14A2H1 (Ashman et al., 1991, Br. J. Haematol. 79, 263-270; Roberts et al., 1995, Br. J. Haematol. 89, 853-860), TS151 and TS151R (Serru et al., 1999, Biochem. J. 340, 103-111; Geary et al., 2001, Tissue Antigens 58, 141-153; Charrin et al., J. Biol. Chem. 276, 14329-14337; Chometon et al., 2006, Exp. Cell Res. 312, 983-985). No in vivo anti-tumour activity has been described for those various antibodies.

Several experimental studies have shown the major role of the tetraspanins in the formation of metastases by acting either as suppressors or as promoters of metastases. Accordingly, the transfection of tetraspanins such as CD9, CD63 or CD82 reduces the metastatic potential of cancer lines. In contrast, expression of the tetraspanins CD151 and Co-029 seems to produce the opposite effect. These 2 tetraspanins are therefore thought to be promoters of metastasis. These results are consistent with various clinical studies which have shown that, in a number of cancers (breast, lung, esophagus, stomach, liver, pancreas, colon, prostate, melanoma, . . . ), CD9 and CD82 are less expressed in primary tumours when there is metastasis and that a reduction in their expression is predictive of a lower survival rate. In lung cancer, the combined reduction in the expression of CD9 and CD82 has been correlated with greater metastatic potential than when expression of just one of those two antigens is reduced.

Several retrospective studies have shown that overexpression of CD151 is associated with aggressiveness of certain cancers, such as lung, colon and prostate cancers, and that it might be considered to be a factor for poor prognosis (Tokuhara et al., 2001, Clin. Cancer Res. 7, 4109-4114; Hashida et al., 2003, Br. J. Cancer 89, 158-167; Ang et al., 2004, Cancer Epidemiol. Biomarkers Prev. 13, 1717-1721). In these cases, mean survival is in fact reduced in those patients having tumours which express CD151, compared to those having tumours which do not express CD151.

The overexpression of CD151 in various human tumor lines (HeLa, RPMI14788, A172, HT1080), brought about by transfection of the corresponding gene, causes an increase in motility, migration and invasion of the transfected cells (Testa et al., 1999, Cancer Res. 59, 3812-3820; Kohno et al., 2002, Int. J. Cancer 97, 336-343). These phenomena are inhibited in the presence of anti-CD151 antibodies.

In accordance with a first aspect, the invention relates to an isolated antibody, or one of its derivative compounds or functional fragments, capable of binding to the CD151 protein, said antibody being characterised in that it comprises at least one CDR selected from the CDRs of sequence SEQ ID No. 1-6, 17-22, 33-35, 43-48, 59-63, 69-73, 79-81 or 85-89 or at least one CDR whose sequence has at least 80%, preferably 85%, 90%, 95% and 98% identity, after optimal alignment, with the sequences SEQ ID No. 1-6, 17-22, 33-35, 43-48, 59-63, 69-73, 79-81 or 85-89.

A "functional fragment" of an antibody according to the invention is understood to refer to, especially, an antibody fragment, such as Fv, scFv (sc standing for "single chain"), Fab, F(ab')$_2$, Fab' or scFv-Fc fragments or diabodies, or any fragment whose half-life may have been increased. Such functional fragments will be described in detail hereinbelow in the present description.

A "derivative compound" of an antibody according to the invention is understood to denote, especially, a binding protein comprising a peptide framework or "scaffold" and at least one of the CDRs of the original antibody in order to preserve its recognition ability. Such derivative compounds are well known to the person skilled in the art and will be described in greater detail hereinbelow in the present description.

More preferably, the invention includes the antibodies, their derivative compounds or their functional fragments, according to the present invention, which are especially chimeric or humanized, that are obtained by genetic recombination or by chemical synthesis.

According to a preferred embodiment, the antibody, or one of its derivative compounds or functional fragments, according to the invention is characterised in that it consists of a monoclonal antibody.

A "monoclonal antibody" is to be understood as an antibody derived from a population of substantially homogeneous antibodies. More especially, the individual antibodies of a population are identical with the exception of a few possible mutations that may be produced naturally and that may be present in minimal amounts. In other words, a monoclonal antibody consists of a homogeneous antibody resulting from the proliferation of just one cell clone (for example, a hybridoma, a eukaryotic host cell transfected with a DNA molecule coding for the homogeneous antibody, a prokaryotic host cell transfected with a DNA molecule coding for the homogeneous antibody, etc.) and which is usually characterised by heavy chains of one and the same class and sub-class and light chains of just one type. Monoclonal antibodies are highly specific and are directed to a single antigen. In addition, in contrast to preparations of polyclonal antibodies which customarily comprise different antibodies directed to different determinants, or epitopes, each monoclonal antibody is directed to a single epitope of the antigen.

It must be understood herein that the invention does not relate to the antibodies in natural form, that is to say they are not taken from their natural environment but rather it has been possible to isolate them or obtain them by purification starting from natural sources, or else obtain them by genetic recombination, or by chemical synthesis, and they may accordingly contain non-natural amino acids as will be described hereinbelow.

More especially, in accordance with a first embodiment of the invention, there is described a first antibody which is characterised in that it comprises:
i) a light chain comprising at least one CDR selected from CDR-L1, CDR-L2 and CDR-L3, wherein
CDR-L1 is selected from the CDRs of sequence SEQ ID No. 1 or 59, or at least one sequence which has at least 80% identity, after optimal alignment, with sequence SEQ ID No. 1 or 59;
CDR-L2 is selected from the CDRs of sequence SEQ ID No. 2 or 60, or at least one sequence which has at least 80% identity, after optimal alignment, with sequence SEQ ID No. 2 or 60;
CDR-L3 is of sequence SEQ ID No. 3 or at least one sequence which has at least 80% identity, after optimal alignment, with the sequence SEQ ID No. 3; and/or
ii) a heavy chain comprising at least one CDR selected from CDR-H1, CDR-H2 and CDR-H3, wherein
CDR-H1 is selected from the CDRs of sequence SEQ ID No. 4 or 61, or at least one sequence which has at least 80% identity, after optimal alignment, with the sequence SEQ ID No. 4 or 61;
CDR-H2 is selected from the CDRs of sequence SEQ ID No. 5 or 62, or at least one sequence which has at least 80% identity, after optimal alignment, with the sequence SEQ ID No. 5 or 62;
CDR-H3 is selected from the CDRs of sequence SEQ ID No. 6 or 63, or at least one sequence which has at least 80% identity, after optimal alignment, with the sequence SEQ ID No. 6 or 63.

In accordance with a second embodiment of the invention, there is described a second antibody which is characterised in that it comprises:
i) a light chain comprising at least one CDR selected from CDR-L1, CDR-L2 and CDR-L3, wherein
CDR-L1 is selected from the CDRs of sequence SEQ ID No. 17 or 69, or at least one sequence which has at least 80% identity, after optimal alignment, with the sequence SEQ ID No. 17 or 69;
CDR-L2 is selected from the CDRs of sequence SEQ ID No. 18 or 70, or at least one sequence which has at least 80% identity, after optimal alignment, with the sequence SEQ ID No. 18 or 70;
CDR-L3 is of sequence SEQ ID No. 19 or at least one sequence which has at least 80% identity, after optimal alignment, with the sequence SEQ ID No. 19; and/or
ii) a heavy chain comprising at least one CDR selected from CDR-H1, CDR-H2 and CDR-H3, wherein
CDR-H1 is selected from the CDRs of sequence SEQ ID No. 20 or 71, or at least one sequence which has at least 80% identity, after optimal alignment, with the sequence SEQ ID No. 20 or 71;
CDR-H2 is selected from the CDRs of sequence SEQ ID No. 21 or 72, or at least one sequence which has at least 80% identity, after optimal alignment, with the sequence SEQ ID No. 21 or 72;
CDR-H3 is selected from the CDRs of sequence SEQ ID No. 22 or 73, or at least one sequence which has at least 80% identity, after optimal alignment, with the sequence SEQ ID No. 22 or 73.

In accordance with a further, third embodiment of the invention, there is described a third antibody which is characterised in that it comprises:
i) a light chain comprising at least one CDR selected from CDR-L1, CDR-L2 and CDR-L3, wherein
CDR-L1 is selected from the CDRs of sequence SEQ ID No. 33 or 79, or at least one sequence which has at least 80% identity, after optimal alignment, with the sequence SEQ ID No. 33 or 79;
CDR-L2 is selected from the CDRs of sequence SEQ ID No. 2 or 60, or at least one sequence which has at least 80% identity, after optimal alignment, with the sequence SEQ ID No. 2 or 60;
CDR-L3 is of sequence SEQ ID No. 3 or at least one sequence which has at least 80% identity, after optimal alignment, with the sequence SEQ ID No. 3; and/or
ii) a heavy chain comprising at least one CDR selected from CDR-H1, CDR-H2 and CDR-H3, wherein
CDR-H1 is selected from the CDRs of sequence SEQ ID No. 4 or 61, or at least one sequence which has at least 80% identity, after optimal alignment, with the sequence SEQ ID No. 4 or 61;
CDR-H2 is selected from the CDRs of sequence SEQ ID No. 34 or 80, or at least one sequence which has at least 80% identity, after optimal alignment, with the sequence SEQ ID No. 34 or 80;
CDR-H3 is selected from the CDRs of sequence SEQ ID No. 35 or 81, or at least one sequence which has at least 80% identity, after optimal alignment, with the sequence SEQ ID No. 35 or 81.

Lastly, in accordance with a final embodiment of the invention, there is described a fourth antibody which is characterised in that it comprises:
i) a light chain comprising at least one CDR selected from CDR-L1, CDR-L2 and CDR-L3, wherein
CDR-L1 is selected from the CDRs of sequence SEQ ID No. 43 or 85, or at least one sequence which has at least 80% identity, after optimal alignment, with the sequence SEQ ID No. 43 or 85;
CDR-L2 is selected from the CDRs of sequence SEQ ID No. 44 or 86, or at least one sequence which has at least 80% identity, after optimal alignment, with the sequence SEQ ID No. 44 or 86;
CDR-L3 is of sequence SEQ ID No. 45 or at least one sequence which has at least 80% identity, after optimal alignment, with the sequence SEQ ID No. 45; and/or
ii) a heavy chain comprising at least one CDR selected from CDR-H1, CDR-H2 and CDR-H3, wherein
CDR-H1 is selected from the CDRs of sequence SEQ ID No. 46 or 87, or at least one sequence which has at least 80% identity, after optimal alignment, with the sequence SEQ ID No. 46 or 87;
CDR-H2 is selected from the CDRs of sequence SEQ ID No. 47 or 88, or at least one sequence which has at least 80% identity, after optimal alignment, with the sequence SEQ ID No. 47 or 88;
CDR-H3 is selected from the CDRs of sequence SEQ ID No. 48 or 89, or at least one sequence which has at least 80% identity, after optimal alignment, with the sequence SEQ ID No. 48 or 89.

In general manner it is recalled here that a CDR region or CDR is understood to denote the hypervariable regions of the heavy chains and light chains of immunoglobulins. There are 3 heavy-chain CDRs and 3 light-chain CDRs. The term CDR or CDRs is used herein to denote, depending on the particular case, one of those regions or a plurality of, or indeed the entirety of, those regions which contain the majority of the amino acid residues responsible for the binding affinity of the antibody for the antigen or the epitope which it recognises.

According to a first approach, the CDRs can be defined in accordance with the IMGT system. The IMGT unique numbering system was defined so as to compare variable domains whatever the antigen, chain type or species [Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In this numbering system, the conserved amino acids always retain the same position, such as cysteine 23 (1st-CYS), tryptophan 41 (CONSERVED TRP), the hydrophobic amino acid 89, cysteine 104 (2nd-CYS), phenylalanine or tryptophan 118 (J-PHE or TRP). The IMGT unique numbering system accordingly provides standardised delimitation of the scaffold regions (FR1-IMGT: positions 1 to 26, FR2-IMGT: positions 39 to 55, FR3-IMGT: positions 66 to 104 and FR4_IMGT: positions 118 to 128) and also of the complementarity determining regions or CDRs (CDR1-IMGT: positions 27 to 38, CDR2-IMGT: positions 56 to 65 and CDR3-IMGT: positions 105 to 117). As the "holes" or "spaces" represent unoccupied positions, the lengths of the CDRs according to IMGT become crucial information. The IMGT system is used in 2D graphical representations which are then referred to as IMGT pearl necklaces [Ruiz, M. and Lefranc, M.-P., Immunogenetics, 53, 857-883 (2002); Kaas, Q. and Lefranc, M.-P., Current Bioinformatics, 2, 21-30 (2007)] and in 3D structures referred to as IMGT/3Dstructure-DB [Kaas, Q., Ruiz, M. and Lefranc, M.-P., T cell receptor and MHC structural data Nucl. Acids. Res., 32, D208-D210 (2004)].

In accordance with this first approach, the first antibody, or one of its derivative compounds or functional fragments, according to the invention comprises a light chain comprising at least one CDR selected from CDR-L1, CDR-L2 and CDR-L3 of sequence SEQ ID Nos. 1, 2 and 3, respectively, or having at least 80%, preferably 85%, 90%, 95% and 98%, identity, after optimal alignment, with the sequences SEQ ID No. 1, 2 and 3; and/or a heavy chain comprising at least one CDR selected from CDR-H1, CDR-H2 and CDR-H3 of sequence SEQ ID Nos. 4, 5 and 6, respectively, or having at least 80%, preferably 85%, 90%, 95% and 98%, identity, after optimal alignment, with the sequences SEQ ID Nos. 4, 5 and 6.

For more clarity, the protein sequences mentioned are the following:

| | |
|---|---|
| SEQ ID No. 1: | ASVEYYGTSL |
| SEQ ID No. 2: | EAS |
| SEQ ID No. 3: | QQSRKAPYT |
| SEQ ID No. 4: | GFTFSTYT |
| SEQ ID No. 5: | ISSGGGTT |
| SEQ ID No. 6: | ATPRIGTGFAY |

More especially, in preferred manner, the antibody, or one of its derivative compounds or functional fragments, according to the invention comprises a light chain comprising the three CDRs, as defined according to IMGT, of sequence SEQ ID Nos. 1, 2 and 3, respectively, or having at least 80%, preferably 85%, 90%, 95% and 98%, identity, after optimal alignment, with the sequences SEQ ID Nos. 1, 2 and 3.

In likewise preferred manner, the antibody, or one of its derivative compounds or functional fragments, according to the invention comprises a heavy chain comprising the three CDRs, as defined according to IMGT, of sequence SEQ ID Nos. 4, 5 and 6, respectively, or having at least 80%, preferably 85%, 90%, 95% and 98%, identity, after optimal alignment, with the sequences SEQ ID Nos. 4, 5 and 6.

In accordance with this same approach, the second antibody, or one of its derivative compounds or functional fragments, according to the invention comprises a light chain comprising at least one CDR selected from CDR-L1, CDR-L2 and CDR-L3 of sequence SEQ ID Nos. 17, 18 and 19, respectively, or having at least 80%, preferably 85%, 90%, 95% and 98%, identity, after optimal alignment, with the sequences SEQ ID Nos. 17, 18 and 19; and/or a heavy chain comprising at least one CDR selected from CDR-H1, CDR-H2 and CDR-H3 of sequence SEQ ID Nos. 20, 21 and 22, respectively, or having at least 80%, preferably 85%, 90%, 95% and 98%, identity, after optimal alignment, with the sequences SEQ ID Nos. 20, 21 and 22.

For more clarity, the protein sequences mentioned are the following:

| | |
|---|---|
| SEQ ID No. 17: | QNVGIA |
| SEQ ID No. 18: | SAS |
| SEQ ID No. 19: | QQYSSNPT |
| SEQ ID No. 20: | GFTLSTSGMG |
| SEQ ID No. 21: | IYWDDDK |
| SEQ ID No. 22: | ARRDHYGDYSYAMDY |

More especially, in preferred manner, the antibody, or one of its derivative compounds or functional fragments, according to the invention comprises a light chain comprising the three CDRs, as defined according to IMGT, of sequence SEQ ID Nos. 17, 18 and 18, respectively, or having at least 80%, preferably 85%, 90%, 95% and 98%, identity, after optimal alignment, with the sequences SEQ ID Nos. 17, 18 and 19.

In likewise preferred manner, the antibody, or one of its derivative compounds or functional fragments, according to the invention comprises a heavy chain comprising the three CDRs, as defined according to IMGT, of sequence SEQ ID Nos. 20, 21 and 22, respectively, or having at least 80%, preferably 85%, 90%, 95% and 98%, identity, after optimal alignment, with the sequences SEQ ID Nos. 20, 21 and 22.

Still in accordance with this same approach, the third antibody, or one of its derivative compounds or functional fragments, according to the invention comprises a light chain comprising at least one CDR selected from CDR-L1, CDR-L2 and CDR-L3 of sequence SEQ ID Nos. 33, 2 and 3, respectively, or having at least 80%, preferably 85%, 90%, 95% and 98%, identity, after optimal alignment, with the sequences SEQ ID Nos. 33, 2 and 3; and/or a heavy chain comprising at least one CDR selected from CDR-H1, CDR-H2 and CDR-H3 of sequence SEQ ID Nos. 4, 34 and 35, respectively, or having at least 80%, preferably 85%, 90%, 95% and 98%, identity, after optimal alignment, with the sequences SEQ ID Nos. 4, 34 and 35.

For more clarity, the protein sequences mentioned are the following:

```
SEQ ID No. 33:     ASVDYYGTSL
SEQ ID No. 34:     ISSGGVTT
SEQ ID No. 35:     TSPRTGTGFAY
```

More especially, in preferred manner, the antibody, or one of its derivative compounds or functional fragments, according to the invention comprises a light chain comprising the three CDRs, as defined according to IMGT, of sequence SEQ ID Nos. 33, 2 and 3, respectively, or having at least 80%, preferably 85%, 90%, 95% and 98%, identity, after optimal alignment, with the sequences SEQ ID Nos. 33, 2 and 3.

In likewise preferred manner, the antibody, or one of its derivative compounds or functional fragments, according to the invention comprises a heavy chain comprising the three CDRs, as defined according to IMGT, of sequence SEQ ID Nos. 4, 34 and 35, respectively, or having at least 80%, preferably 85%, 90%, 95% and 98%, identity, after optimal alignment, with the sequences SEQ ID Nos. 4, 34 and 35.

Finally, still in accordance with this same approach, the fourth and last antibody, or one of its derivative compounds or functional fragments, according to the invention comprises a light chain comprising at least one CDR selected from CDR-L1, CDR-L2 and CDR-L3 of sequence SEQ ID Nos. 43, 44 and 45, respectively, or having at least 80%, preferably 85%, 90%, 95% and 98%, identity, after optimal alignment, with the sequences SEQ ID Nos. 43, 44 and 45; and/or a heavy chain comprising at least one CDR selected from CDR-H1, CDR-H2 and CDR-H3 of sequence SEQ ID Nos. 46, 47 and 48, respectively, or having at least 80%, preferably 85%, 90%, 95% and 98%, identity, after optimal alignment, with the sequences SEQ ID Nos. 46, 47 and 48.

For more clarity, the protein sequences mentioned are the following:

```
SEQ ID No. 43:     ENVGTY
SEQ ID No. 44:     GAS
SEQ ID No. 45:     GQTYSFPYT
SEQ ID No. 46:     GYTFTSSS
SEQ ID No. 47:     IHPNSGNT
SEQ ID No. 48:     ARARSFYYAMDC
```

More especially, in preferred manner, the antibody, or one of its derivative compounds or functional fragments, according to the invention comprises a light chain comprising the three CDRs, as defined according to IMGT, of sequence SEQ ID Nos. 43, 44 and 45, respectively, or having at least 80%, preferably 85%, 90%, 95% and 98%, identity, after optimal alignment, with the sequences SEQ ID Nos. 43, 44 and 45.

In likewise preferred manner, the antibody, or one of its derivative compounds or functional fragments, according to the invention comprises a heavy chain comprising the three CDRs, as defined according to IMGT, of sequence SEQ ID Nos. 46, 47 and 48, respectively, or having at least 80%, preferably 85%, 90%, 95% and 98%, identity, after optimal alignment, with the sequences SEQ ID Nos. 46, 47 and 48.

According to a second approach, the CDRs can be defined according to the customary approach of Kabat et al. (Kabat et al., Sequences of proteins of immunological interest, 5$^{th}$ Ed., U.S. Department of Health and Human Services, NIH, 1991, and later editions).

In accordance with this first approach, the first antibody, or one of its derivative compounds or functional fragments, according to the invention comprises a light chain comprising at least one CDR selected from CDR-L1, CDR-L2 and CDR-L3 of sequence SEQ ID Nos. 59, 60 and 3, respectively, or having at least 80%, preferably 85%, 90%, 95% and 98%, identity, after optimal alignment, with the sequences SEQ ID Nos. 59, 60 and 3; and/or a heavy chain comprising at least one CDR selected from CDR-H1, CDR-H2 and CDR-H3 of sequence SEQ ID Nos. 61, 62 and 63, respectively, or having at least 80%, preferably 85%, 90%, 95% and 98%, identity, after optimal alignment, with the sequences SEQ ID Nos. 61, 62 and 63.

For more clarity, the protein sequences mentioned are the following:

```
SEQ ID No. 59:     RASASVEYYGTSLMH
SEQ ID No. 60:     EASNVES
SEQ ID No. 61:     STYTMS
SEQ ID No. 62:     YISSGGGTTYYPDTVKG
SEQ ID No. 63:     PRIGTGFAY
```

More especially, in preferred manner, the antibody, or one of its derivative compounds or functional fragments, according to the invention comprises a light chain comprising the three CDRs, as defined according to Kabat, of sequence SEQ ID Nos. 59, 60 and 3, respectively, or having at least 80%, preferably 85%, 90%, 95% and 98%, identity, after optimal alignment, with the sequences SEQ ID Nos. 59, 60 and 3.

In likewise preferred manner, the antibody, or one of its derivative compounds or functional fragments, according to the invention comprises a heavy chain comprising the three CDRs, as defined according to Kabat, of sequence SEQ ID Nos. 61, 62 and 63, respectively, or having at least 80%, preferably 85%, 90%, 95% and 98%, identity, after optimal alignment, with the sequences SEQ ID Nos. 61, 62 and 63.

In accordance with this same approach, the second antibody, or one of its derivative compounds or functional fragments, according to the invention comprises a light chain comprising at least one CDR selected from CDR-L1, CDR-L2 and CDR-L3 of sequence SEQ ID Nos. 69, 70 and 19, respectively, or having at least 80%, preferably 85%, 90%, 95% and 98%, identity, after optimal alignment, with the sequences SEQ ID Nos. 69, 70 and 19; and/or a heavy chain comprising at least one CDR selected from CDR-H1, CDR-H2 and CDR-H3 of sequence SEQ ID Nos. 71, 72 and 73, respectively, or having at least 80%, preferably 85%, 90%, 95% and 98%, identity, after optimal alignment, with the sequences SEQ ID Nos. 71, 72 and 73.

For more clarity, the protein sequences mentioned are the following:

```
SEQ ID No. 69:     KASQNVGIAVA
SEQ ID No. 70:     SASNRYT
SEQ ID No. 71:     STSGMGVS
SEQ ID No. 72:     HIYWDDDKRYNPSLKS
SEQ ID No. 73:     RDHYGDYSYAMDY
```

More especially, in preferred manner, the antibody, or one of its derivative compounds or functional fragments, according to the invention comprises a light chain comprising the three CDRs, as defined according to Kabat, of sequence SEQ ID Nos. 69, 70 and 19, respectively, or having at least 80%, preferably 85%, 90%, 95% and 98%, identity, after optimal alignment, with the sequences SEQ ID Nos. 69, 70 and 19.

In likewise preferred manner, the antibody, or one of its derivative compounds or functional fragments, according to the invention comprises a heavy chain comprising the three CDRs, as defined according to Kabat, of sequence SEQ ID Nos. 71, 72 and 73, respectively, or having at least 80%, preferably 85%, 90%, 95% and 98%, identity, after optimal alignment, with the sequences SEQ ID Nos. 71, 72 and 73.

Still in accordance with this same approach, the third antibody, or one of its derivative compounds or functional fragments, according to the invention comprises a light chain comprising at least one CDR selected from CDR-L1, CDR-L2 and CDR-L3 of sequence SEQ ID Nos. 79, 60 and 3, respectively, or having at least 80%, preferably 85%, 90%, 95% and 98%, identity, after optimal alignment, with the sequences SEQ ID Nos. 79, 60 and 3; and/or a heavy chain comprising at least one CDR selected from CDR-H1, CDR-H2 and CDR-H3 of sequence SEQ ID Nos. 61, 80 and 81, respectively, or having at least 80%, preferably 85%, 90%, 95% and 98%, identity, after optimal alignment, with the sequences SEQ ID Nos. 100, 101 and 102.

For more clarity, the protein sequences mentioned are the following:

| | |
|---|---|
| SEQ ID No. 79: | RASASVDYYGTSLMQ |
| SEQ ID No. 80: | YISSGGVTTYYPDTIKG |
| SEQ ID No. 81: | PRTGTGFAY |

More especially, in preferred manner, the antibody, or one of its derivative compounds or functional fragments, according to the invention comprises a light chain comprising the three CDRs, as defined according to Kabat, of sequence SEQ ID Nos. 79, 60 and 3, respectively, or having at least 80%, preferably 85%, 90%, 95% and 98%, identity, after optimal alignment, with the sequences SEQ ID Nos. 79, 60 and 3.

In likewise preferred manner, the antibody, or one of its derivative compounds or functional fragments, according to the invention comprises a heavy chain comprising the three CDRs, as defined according to Kabat, of sequence SEQ ID No. 61, 80 and 81, respectively, or having at least 80%, preferably 85%, 90%, 95% and 98%, identity, after optimal alignment, with the sequences SEQ ID Nos. 61, 80 and 81.

Finally, still according to this same approach, the fourth and final antibody, or one of its derivative compounds or functional fragments, according to the invention comprises a light chain comprising at least one CDR selected from CDR-L1, CDR-L2 and CDR-L3 of sequence SEQ ID Nos. 85, 86 and 45, respectively, or having at least 80%, preferably 85%, 90%, 95% and 98%, identity, after optimal alignment, with the sequences SEQ ID Nos. 85, 86 and 45; and/or a heavy chain comprising at least one CDR selected from CDR-H1, CDR-H2 and CDR-H3 of sequence SEQ ID Nos. 87, 88 and 89, respectively, or having at least 80%, preferably 85%, 90%, 95% and 98%, identity, after optimal alignment, with the sequences SEQ ID Nos. 87, 88 and 89.

For more clarity, the protein sequences mentioned are the following:

| | |
|---|---|
| SEQ ID No. 85: | KASENVGTYVS |
| SEQ ID No. 86: | GASNRYTGVPD |
| SEQ ID No. 87: | TSSSMH |
| SEQ ID No. 88: | EIHPNSGNTNNNEKFKG |
| SEQ ID No. 89: | ARSFYYAMDC |

More especially, in preferred manner, the antibody, or one of its derivative compounds or functional fragments, according to the invention comprises a light chain comprising the three CDRs, as defined according to Kabat, of sequence SEQ ID Nos. 85, 86 and 45, respectively, or having at least 80%, preferably 85%, 90%, 95% and 98%, identity, after optimal alignment, with the sequences SEQ ID Nos. 85, 86 and 45.

In likewise preferred manner, the antibody, or one of its derivative compounds or functional fragments, according to the invention comprises a heavy chain comprising the three CDRs, as defined according to Kabat, of sequence SEQ ID Nos. 87, 88 and 89, respectively, or having at least 80%, preferably 85%, 90%, 95% and 98%, identity, after optimal alignment, with the sequences SEQ ID Nos. 87, 88 and 89.

In the present description, the terms "polypeptides", "polypeptide sequences", "peptides" and "proteins" associated with the antibody compounds or their sequences are interchangeable.

It must be understood herein that the invention does not relate to the antibodies in natural form, that is to say they are not taken from their natural environment but may have been isolated or obtained by purification starting from natural sources, or else obtained by genetic recombination, or by chemical synthesis, and they may accordingly contain non-natural amino acids as will be described hereinbelow.

"Percentage identity" between two nucleic acid or amino acid sequences is understood by the present invention to denote the percentage of nucleotides or amino acid residues that are identical between the two sequences being compared, obtained after the best alignment (optimal alignment), this percentage being purely statistical and the differences between the two sequences being randomly distributed throughout their length. Sequence comparisons between two nucleic acid or amino acid sequences are customarily carried out by comparing those sequences after they have been optimally aligned, it being possible for said comparison to be carried out segment by segment or by means of a "comparison window". The optimal alignment of sequences for the comparison can, besides being carried out manually, be carried out by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444], or by means of computer software employing those algorithms (GAP, BESTFIT, FASTA and TFASTA in the Wisconsin Genetics Software Package, Genetics Computer Group, 575 Science Dr., Madison, Wis., or by the comparison software BLAST N or BLAST P).

The percentage identity between two nucleic acid or amino acid sequences is determined by comparing the two optimally aligned sequences in which the nucleic acid or amino acid sequence to be compared can contain additions or deletions with respect to the reference sequence for optimal alignment between those two sequences. The percentage identity is calculated by determining the number of identical positions where the nucleotide or amino acid residue is identical between the two sequences, dividing that number of identical positions by the total number of positions in the comparison window and multiplying the result obtained by 100 in order to obtain the percentage identity between the two sequences.

For example, there may be used the BLAST program "BLAST 2 sequences" (Tatusova et al., "Blast 2 sequences—a new tool for comparing protein and nucleotide sequences", FEMS Microbiol Lett. 174:247-250), the parameters used being those given as default (especially for the parameters "open gap penalty": 5, and "extension gap penalty": 2; the selected matrix being, for example, the "BLOSUM 62" matrix suggested by the program), the percentage identity between the two sequences for comparison being calculated directly by the program.

As an amino acid sequence having at least 80%, preferably 85%, 90%, 95% and 98%, identity with a reference amino acid sequence preference is given to one having, with respect to the reference sequence, certain modifications, especially a deletion, addition or substitution of at least one amino acid, a truncation or an extension. In the case of a substitution of one or more consecutive or non-consecutive amino acid(s) preference is given to substitutions in which the substituted amino acids are replaced by "equivalent" amino acids. The expression "equivalent amino acids" is intended herein to denote any amino acid capable of being substituted for one of the amino acids of the basic structure without, however, fundamentally modifying the biological activities of the corresponding antibodies, such as will be defined hereinbelow, especially in the Examples.

These equivalent amino acids can be determined either on the basis of their structural homology with the amino acids for which they are being substituted or on the basis of results of comparative biological activity tests between the various antibodies that may be produced.

By way of non-limiting example, Table 1 below recalls the substitution possibilities capable of being carried out without resulting in fundamental modification of the biological activity of the corresponding modified antibody, the reverse substitutions being feasible of course under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It is recognised by the person skilled in the art, as prior art, that the greatest variability (length and composition) between the 6 CDRs is located in the 3 CDRs of the heavy chain and, more especially, the CDR-H3 of that heavy chain. Consequently, it will be evident that the preferred characteristic CDRs of the antibody according to the invention will be the 3 CDRs of the heavy chain and, even more preferably, the CDR corresponding to the CDR-H3.

In a particular embodiment, the present invention relates to a murine antibody, or one of its derivative compounds or functional fragments, according to the invention.

According to another embodiment of the invention, said first antibody, or one of its derivative compounds or functional fragments, comprises a light chain comprising the three CDRs, as defined according to IMGT, of sequence SEQ ID Nos. 1, 2 and 3, respectively, or having at least 80%, preferably 85%, 90%, 95% and 98%, identity, after optimal alignment, with the sequences SEQ ID Nos. 1, 2 and 3; and a heavy chain comprising the three CDRs of sequence SEQ ID Nos. 4, 5 and 6, respectively, or having at least 80%, preferably 85%, 90%, 95% and 98%, identity, after optimal alignment, with the sequences SEQ ID Nos. 4, 5 and 6.

According to yet another embodiment of the invention, said first antibody, or one of its derivative compounds or functional fragments, comprises a light chain comprising the three CDRs, as defined according to Kabat, of sequence SEQ ID Nos. 59, 60 and 3, respectively, or having at least 80%, preferably 85%, 90%, 95% and 98%, identity, after optimal alignment, with the sequences SEQ ID Nos. 59, 60 and 3; and a heavy chain comprising the three CDRs of sequence SEQ ID Nos. 61, 62 and 63, respectively, or having at least 80%, preferably 85%, 90%, 95% and 98%, identity, after optimal alignment, with the sequences SEQ ID Nos. 61, 62 and 63.

According to yet another embodiment, the antibody, or one of its derivative compounds or functional fragments, according to the invention comprises a light chain having a sequence comprising the amino acid sequence SEQ ID No. 7 or having at least 80%, preferably 85%, 90%, 95% and 98%, identity, after optimal alignment, with the sequence SEQ ID No. 7, and/or it comprises a heavy chain having a sequence comprising the amino acid sequence SEQ ID No. 8 or having at least 80%, preferably 85%, 90%, 95% and 98%, identity, after optimal alignment, with the sequence SEQ ID No. 8.

For more clarity, the protein sequences mentioned are the following:

SEQ ID No. 7:
DIVLSQSPASLALSLGQRATISCRASASVEYYGTSLMHWYQQKPGQPPKL

LIYEASNVESGVPARFSGSGSGTDFSLNIHPVEEDDLAIYFCQQSRKAPY

TFGGGTKLEIK

SEQ ID No. 8:
EVKLVESGGGLVQPGGSLKLSCAASGFTFSTYTMSWVRQTPEKRLEWVAY

ISSGGGTTYYPDTVKGRFTISRDNARNTLYLQMNSLKSEDTAMYYCATPR

IGTGFAYWGQGTLVTVSA

According to another embodiment of the invention, said second antibody, or one of its derivative compounds or functional fragments, comprises a light chain comprising the three CDRs, as defined according to IMGT, of sequence SEQ ID Nos. 17, 18 and 19, respectively, or having at least 80%, preferably 85%, 90%, 95% and 98%, identity, after optimal alignment, with the sequences SEQ ID Nos. 17, 18 and 19; and a heavy chain comprising the three CDRs of sequence SEQ ID Nos. 20, 21 and 22, respectively, or having at least 80%, preferably 85%, 90%, 95% and 98%, identity, after optimal alignment, with the sequences SEQ ID Nos. 20, 21 and 22.

According to yet another embodiment of the invention, said second antibody, or one of its derivative compounds or functional fragments, comprises a light chain comprising the three CDRs, as defined according to Kabat, of sequence SEQ ID Nos. 69, 70 and 19, respectively, or having at least 80%, preferably 85%, 90%, 95% and 98%, identity, after optimal alignment, with the sequences SEQ ID Nos. 69, 70 and 19; and a heavy chain comprising the three CDRs of sequence SEQ ID Nos. 71, 72 and 73, respectively, or having at least 80%, preferably 85%, 90%, 95% and 98%, identity, after optimal alignment, with the sequences SEQ ID Nos. 71, 72 and 73.

According to yet another embodiment, the antibody, or one of its derivative compounds or functional fragments, according to the invention comprises a light chain having a sequence comprising the amino acid sequence SEQ ID No. 23 or having at least 80%, preferably 85%, 90%, 95% and 98%, identity, after optimal alignment, with the sequence SEQ ID No. 23, and/or comprises a heavy chain having a sequence comprising the amino acid sequence SEQ ID No. 24 or having at least 80%, preferably 85%, 90%, 95% and 98% identity, after optimal alignment, with the sequence SEQ ID No. 24.

For more clarity, the protein sequences mentioned are the following:

SEQ ID No. 23:
DIVMTQSQKFMSTSEGDRVSITCKASQNVGIAVAWYQQKPGQSPKLLIYS

ASNRYTGVPDRFTGSGSGTDFTLTISNMQSEDLADYFCQQYSSNPTFGAG

TKLELK

SEQ ID No. 24:
QVTLKESGPGILQPSQTLSLTCSFSGFTLSTSGMGVSWIRQPSGKGLEWL

AHIYWDDDKRYNPSLKSRLTISKDTSRNQVFLKITSVDTADTATYYCARR

DHYGDYSYAMDYWGQGTSVTVSS

According to another embodiment of the invention, said third antibody, or one of its derivative compounds or functional fragments, comprises a light chain comprising the three CDRs, as defined according to IMGT, of sequence SEQ ID Nos. 33, 2 and 3, respectively, or having at least 80%, preferably 85%, 90%, 95% and 98%, identity, after optimal alignment, with the sequences SEQ ID Nos. 33, 2 and 3; and a heavy chain comprising the three CDRs of sequence SEQ ID Nos. 4, 34 and 35, respectively, or having at least 80%, preferably 85%, 90%, 95% and 98%, identity, after optimal alignment, with the sequences SEQ ID Nos. 4, 34 and 35.

According to yet another embodiment of the invention, said third antibody, or one of its derivative compounds or functional fragments, comprises a light chain comprising the three CDRs, as defined according to Kabat, of sequence SEQ ID Nos. 79, 60 and 3, respectively, or having at least 80%, preferably 85%, 90%, 95% and 98%, identity, after optimal alignment, with the sequences SEQ ID Nos. 79, 60 and 3; and a heavy chain comprising the three CDRs of sequence SEQ ID Nos. 61, 80 and 81, respectively, or having at least 80%, preferably 85%, 90%, 95% and 98%, identity, after optimal alignment, with the sequences SEQ ID Nos. 61, 80 and 81.

According to yet another embodiment, the antibody, or one of its derivative compounds or functional fragments, according to the invention comprises a light chain having a sequence comprising the amino acid sequence SEQ ID No. 36 or having at least 80%, preferably 85%, 90%, 95% and 98%, identity, after optimal alignment, with the sequence SEQ ID No. 36, and/or comprises a heavy chain having a sequence comprising the amino acid sequence SEQ ID No. 37 or having at least 80%, preferably 85%, 90%, 95% and 98%, identity, after optimal alignment, with sequence SEQ ID No. 37.

For more clarity, the protein sequences mentioned are the following:

SEQ ID No. 36:
DIVLTQSPASLALSLGQRATISCRASASVDYYGTSLMQWYQQKPGQPPKL

LIYEASNVESGVPARFSGSGSGTDFSLNIHPVEEDDLAIYFCQQSRKAPY

TFGGGTKLEIK

SEQ ID No. 37:
EVKLVESGGDLVQPGGSLKLSCAASGFTFSTYTMSWVRQTPEKRLEWVAY

ISSGGVTTYYPDTIKGRFTISRDNAKNTLFLQMNSLKSEDTAMYYCTSPR

TGTGFAYWGQGTLVTVSA

According to another embodiment of the invention, said fourth antibody, or one of its derivative compounds or functional fragments, comprises a light chain comprising the three CDRs, as defined according to IMGT, of sequence SEQ ID Nos. 43, 44 and 45, respectively, or having at least 80%, preferably 85%, 90%, 95% and 98%, identity, after optimal alignment, with the sequences SEQ ID Nos. 43, 44 and 45; and a heavy chain comprising the three CDRs of sequence SEQ ID Nos. 46, 47 and 48, respectively, or having at least 80%, preferably 85%, 90%, 95% and 98%, identity, after optimal alignment, with the sequences SEQ ID Nos. 46, 47 and 48.

According to yet another embodiment of the invention, said fourth antibody, or one of its derivative compounds or functional fragments, comprises a light chain comprising the three CDRs, as defined according to Kabat, of sequence SEQ ID Nos. 85, 86 and 45, respectively, or having at least 80%, preferably 85%, 90%, 95% and 98%, identity, after optimal alignment, with the sequences SEQ ID Nos. 85, 86 and 45; and a heavy chain comprising the three CDRs of sequence SEQ ID Nos. 87, 88 and 89, respectively, or having at least 80%, preferably 85%, 90%, 95% and 98%, identity, after optimal alignment, with the sequences SEQ ID Nos. 87, 88 and 89.

According to yet another embodiment, the antibody, or one of its derivative compounds or functional fragments, according to the invention comprises a light chain having a sequence comprising the amino acid sequence SEQ ID No. 49 or having at least 80%, preferably 85%, 90%, 95% and 98%, identity, after optimal alignment, with the sequence SEQ ID No. 49, and/or comprises a heavy chain having a sequence comprising the amino acid sequence SEQ ID No. 50 or having at least 80%, preferably 85%, 90%, 95% and 98%, identity, after optimal alignment, with the sequence SEQ ID No. 50.

For more clarity, the protein sequences mentioned are the following:

SEQ ID No. 49:
NIVMTQSPKSMSMSVGERVTLSCKASENVGTYVSWYQQKPEQSPKLLIYG

ASNRYTGVPDRFTGSGSATDFTLTISSVQAEDLADYHCGQTYSFPYTFGG

GTKLEIK

SEQ ID No. 50:
QVQLQQPGSVLVRPGASVKLSCKASGYTFTSSSMHWAKQRPGQGLEWIGE

IHPNSGNTNNNEKFKGKATLTVDTSSSTAYVDLSSLSSEDSAVYYCARAR

SFYYAMDCWGQGTSVTVSS

As indicated hereinbefore, the invention is likewise directed at any compound derived from an antibody according to the invention.

More especially, the antibody, or one of its derivative compounds or functional fragments, according to the invention is characterised in that said derivative compound consists of a binding protein comprising a peptide scaffold onto which is grafted at least one CDR so as to preserve, in entirety or in part, the paratopic recognition properties of the initial antibody.

One or more sequences among the sequences of the CDRs described in this invention can also be provided on various protein scaffolds—or frameworks—of immunoglobulins. In this case, the protein sequence makes it possible to recreate a peptide skeleton favourable to the folding of the grafted CDR or CDRs, allowing it/them to preserve their paratopic properties of antigen recognition.

In general manner, the person skilled in the art will know how to determine the type of protein scaffold onto which to graft at least one of the CDRs derived from the original antibody. More especially, it is known that, in order to be selected, such scaffolds must meet the greatest number of criteria as listed below (Skerra A., J. Mol. Recogn. 13, 2000, 167-187):
- good phylogenetic conservation;
- known three-dimensional structure (such as, for example, from crystallography, NMR spectroscopy or any other technique known to the person skilled in the art);
- small size;
- few or no post-transcriptional modifications; and/or
- ease of production, expression and purification.

The origin of such protein scaffolds can be, but is not limited to, structures selected from: fibronectin and preferably the 10th domain of type 3 fibronectin, lipocalin, anticalin (Skerra A., J. Biotechnol., 2001, 74(4):257-75), protein Z derived from domain B of protein A of *Staphylococcus aureus*, thioredoxin A and also proteins having repeated motifs of the "ankyrin repeat" (Kohl et al., PNAS, 2003, vol. 100, No. 4, 1700-1705), "armadillo repeat", "leucine-rich repeat" or "tetratricopeptide repeat" types.

There may also be mentioned scaffolds derived from toxins such as, for example, the following toxins derived from scorpions, insects, plants, molluscs, etc. or protein inhibitors of neuronal NO synthase (PIN).

As an example—which is in no way limiting—of such hybrid structures there may be mentioned the insertion of the CDR-H1 (heavy chain) of an anti-CD4 antibody, namely 13B8.2, into one of the loops of PIN, the new binding protein thereby obtained retaining the same binding properties as the original antibody (Bes et al., BBRC 343, 2006, 334-344). There may also be mentioned, by way of illustration, the grafting of the CDR-H3 (heavy chain) of an anti-lysozyme VHH antibody onto one of the loops of neocarzinostatin (Nicaise et al., 2004).

Finally, as described hereinbefore, such peptide scaffolds can comprise from 1 to 6 CDR(s) derived from the original antibody. Preferably, but without its being a necessity, the person skilled in the art will select at least one CDR derived from the heavy chain, the latter being known to be principally responsible for the specificity of the antibody. Selection of the relevant CDR(s) will be obvious to the person skilled in the art, the latter employing known techniques for the purpose (Bes et al., FEBS letters 508, 2001 67-74).

Obviously, these examples are in no way limiting, and any other structure known or obvious to the skilled person must be considered as being included within the protection afforded by the present patent application.

The present invention accordingly relates to an antibody, or one of its derivative compounds or functional fragments, characterised in that said peptide scaffold is selected from proteins which a) are phylogenetically well conserved, b) are of robust architecture, c) have well-known three-dimensional molecular organisation, d) are of small size and/or e) comprise regions that can be modified by deletion and/or insertion without changes to the stability properties.

According to a preferred embodiment, the antibody, or one of its derivative compounds or functional fragments, according to the invention is characterised in that the peptide scaffold is selected from i) scaffolds derived from fibronectin, preferably the 10th domain of type 3 fibronectin, lipocalin, anticalin, protein Z derived from domain B of protein A of *Staphylococcus aureus*, thioredoxin A, ii) proteins having repeated motifs of the "ankyrin repeat", "armadillo repeat", "leucine-rich repeat" or "tetratricopeptide repeat" type and also iii) protein inhibitors of neuronal NO synthase (PIN).

In accordance with another aspect of the invention, mention is likewise made of the functional fragments of the antibody described hereinbefore.

More especially, the invention is directed to an antibody, or one of its derivative compounds or functional fragments, the invention characterised in that said functional fragment is selected from Fv, Fab, (Fab')$_2$, Fab', scFv and scFv-Fc fragments and diabodies, and any fragment whose half-life may have been extended such as pegylated fragments.

Such functional fragments of antibodies according to the invention consist, for example, of Fv, scFv (sc standing for single chain), Fab, F(ab')$_2$, Fab' or scFv-Fc fragments or diabodies, or any fragment whose half-life may have been extended by chemical modification, e.g. addition of poly (alkylene)glycol such as poly(ethylene)glycol ("PEGylation") (the PEGylated fragments being referred to as Fv-PEG, scFv-PEG, Fab-PEG, F(ab')$_2$-PEG or Fab'-PEG) ("PEG" from the designation Poly(Ethylene)Glycol), or by incorporation in a liposome, microspheres or PLGA, said fragments having at least one of the characteristic CDRs according to the invention and, especially, being capable of generally exerting activity, even partial, of the antibody from which it is derived.

Preferably, said functional fragments will be composed of or will comprise a partial sequence of the variable heavy or light chain of the antibody from which they are derived, said partial sequence being sufficient to retain the same binding specificity as the antibody from which it is derived and an adequate affinity, preferably equal to at least $1/100$th, more preferably at least $1/10$th, of that of the antibody from which it is derived.

Such a functional fragment will comprise at least 5 consecutive amino acids, preferably 10, 15, 25, 50 or 100 consecutive amino acids, from the sequence of the antibody from which it is derived.

Preferably, these functional fragments will be fragments of Fv, scFv, Fab, F(ab')$_2$, F(ab'), scFv-Fc type, or diabodies, which generally have the same fixing specificity as the antibody from which they are obtained. According to the present invention, fragments of antibodies of the invention can be obtained starting from antibodies as described hereinbefore by methods such as digestion using enzymes such as pepsin or papain and/or by cleavage of the disulfide bridges by means of chemical reduction. The antibody fragments included in the present invention can also be obtained by genetic recombination techniques that are likewise well-known to the person skilled in the art or by peptide synthesis by means of, for example, automatic peptide synthesisers such as those supplied by the company Applied Biosystems, etc.

According to another particular aspect, the present invention relates to a chimeric antibody, or one of its derivative compounds or functional fragments, according to the invention, characterised in that said antibody also comprises constant light chain and heavy chain regions derived from an antibody from a species heterologous to the mouse, especially from humans.

According to yet another aspect of the invention, the humanized antibody, or one of its derivative compounds or functional fragments, is characterised in that the constant light chain and heavy chain regions derived from a human antibody are the lambda or kappa region and the gamma-1, gamma-2 or gamma-4 region, respectively.

According to another aspect, the invention relates to a first murine hybridoma capable of secreting a monoclonal antibody according to the present invention, especially the hybridoma of murine origin as deposited at the Centre National de Cultures de Microorganismes (CNCM) (Institut Pasteur, Paris, France) on 22 Feb. 2008 under number I-3920. Said hybridoma was obtained by fusion of immunised Balb/c mice splenocytes and Sp 20 Ag 14 myeloma cell lines. Said hybridoma deposited at the CNCM on 22 Feb. 2008 under number I-3920 secretes the monoclonal antibody referred to herein as 203B6, or one of its derivative compounds or functional fragments.

According to another aspect, the invention relates to a first murine hybridoma capable of secreting a monoclonal antibody according to the present invention, especially the hybridoma of murine origin as deposited at the Collection Nationale de Cultures de Microorganismes (CNCM) (Institut Pasteur, 28, rue du Dr. Roux, 75724, Paris, Cédex 15, France) on 22 Feb. 2008 under number I-3920. Said hybridoma was obtained by fusion of immunised Balb/c mice splenocytes and Sp 2O Ag 14 myeloma cell lines. Said hybridoma deposited at the CNCM on 22 Feb. 2008 under number I-3920 secretes the monoclonal antibody referred to herein as 203B6, or one of its derivative compounds or functional fragments.

According to another aspect, the invention relates to a second murine hybridoma capable of secreting a monoclonal antibody according to the present invention, especially the hybridoma of murine origin as deposited at the Collection Nationale de Cultures de Microorganismes (CNCM) (Institut Pasteur, 28, rue du Dr. Roux, 75724, Paris, Cédex 15, France) on 22 Feb. 2008 under number I-3921. Said hybridoma was obtained by fusion of immunised Balb/c mice splenocytes and Sp 2O Ag 14 myeloma cell lines. Said hybridoma deposited at the CNCM on 22 Feb. 2008 under number I-3921 secretes the monoclonal antibody referred to herein as 205H8, or one of its derivative compounds or functional fragments.

According to another aspect, the invention relates to a third murine hybridoma capable of secreting a monoclonal antibody according to the present invention, especially the hybridoma of murine origin as deposited at the Collection Nationale de Cultures de Microorganismes (CNCM) (Institut Pasteur, 28, rue du Dr. Roux, 75724, Paris, Cédex 15, France) on 21 Feb. 2008 under number I-3918. Said hybridoma was obtained by fusion of immunised Balb/c mice splenocytes and Sp 2O Ag 14 myeloma cell lines. Said hybridoma deposited at the CNCM on 21 Feb. 2008 under number I-3918 secretes the monoclonal antibody referred to herein as 211F3, or one of its derivative compounds or functional fragments.

Finally, according to another aspect, the invention relates to a fourth murine hybridoma capable of secreting a monoclonal antibody according to the present invention, especially the hybridoma of murine origin as deposited at the Collection Nationale de Cultures de Microorganismes (CNCM) (Institut Pasteur, 28, rue du Dr. Roux, 75724, Paris, Cédex 15, France) on 21 Feb. 2008 under number I-3919. Said hybridoma was obtained by fusion of immunised Balb/c mice splenocytes and Sp 2O Ag 14 myeloma cell lines. Said hybridoma deposited at the CNCM on 21 Feb. 2008 under number I-3919 secretes the monoclonal antibody referred to herein as 214B2, or one of its derivative compounds or functional fragments.

For more clarity, Table 2 hereinbelow summarises the different amino acid sequences corresponding to the different antibodies according to the invention, with the CDR sequences defined according to IMGT in bold and those defined according to Kabat in italics.

TABLE 2

|  | 203B6 (I-3920) | | 205H8 (I-3921) | | 211F3 (I-3918) | | 214B2 (I-3919) | |
| --- | --- | --- | --- | --- | --- | --- | --- | --- |
| CDR-L1 | 1 | *59* | 17 | *69* | 33 | *79* | 43 | *85* |
| CDR-L2 | 2 | *60* | 18 | *70* | 2 | *60* | 44 | *86* |
| CDR-L3 | 3 | *3* | 19 | *19* | 3 | *3* | 45 | *45* |
| Light Chain (VL) | 7 | | 23 | | 36 | | 49 | |
| Chim. VL | 101 | | | | | | 95 | |
| CDR-H1 | 4 | *61* | 20 | *71* | 4 | *61* | 46 | *87* |
| CDR-H2 | 5 | *62* | 21 | *72* | 34 | *80* | 47 | *88* |
| CDR-H3 | 6 | *63* | 22 | *73* | 35 | *81* | 48 | *89* |
| Heavy Chain (VH) | 8 | | 24 | | 37 | | 50 | |
| IgG1 Chim. VH | 102 | | | | | | 96 | |
| IgG4 Chim. VH | 103 | | | | | | 97 | |

Antibodies according to the present invention also include chimeric or humanized antibodies.

A chimeric (also referred as chimaeric) antibody is understood as referring to an antibody which contains a natural variable (light chain and heavy chain) region derived from an antibody from a given species in association with the constant light chain and heavy chain regions of an antibody from a heterologous species to said given species.

Chimeric-type antibodies, or their fragments, according to the invention can be prepared using genetic recombination techniques. For example, the chimeric antibody may be produced by cloning a recombinant DNA comprising a promoter and a sequence coding for the variable region of a non-human, especially murine, monoclonal antibody according to the invention and a sequence coding for the constant region of a human antibody. A chimeric antibody of the invention encoded by such a recombinant gene may be, for example, a mouse-human chimaera, the specificity of that antibody being determined by the variable region derived from the murine DNA and its isotype determined by the constant region derived from the human DNA. For methods of preparing chimeric antibodies, reference may be made, for example to the document Verhoeyn et al. (BioEssays, 8:74, 1988).

In another aspect, the invention describes an antibody, or a derived compound or functional fragment of same, which consists in a chimeric antibody.

In a particular preferred embodiment, the chimeric antibody, or a derived compound or functional fragment of same, of the invention comprises a light chain sequence comprising the amino acid sequence SEQ ID No. 95, and in that it comprises a heavy chain sequence comprising the amino acid sequence SEQ ID No. 96 or 97.

The two heavy chain sequences, SEQ ID Nos. 96 and 97, are corresponding to the human isotype IgG1 and IgG4, respectively.

As a consequence, a first embodiment of the invention discloses a chimeric antibody c214B2[IgG1], or a derived compound or functional fragment of same, of the invention comprises a light chain sequence comprising the amino acid sequence SEQ ID No. 95, and in that it comprises a heavy chain sequence comprising the amino acid sequence SEQ ID No. 96.

A second embodiment of the invention discloses a chimeric antibody c214B2[IgG4], or a derived compound or functional fragment of same, of the invention comprises a light chain sequence comprising the amino acid sequence SEQ ID No. 95, and in that it comprises a heavy chain sequence comprising the amino acid sequence SEQ ID No. 97.

In another preferred embodiment, the chimeric antibody, or a derived compound or functional fragment of same, of the invention comprises a light chain sequence comprising the amino acid sequence SEQ ID No. 101, and in that it comprises a heavy chain sequence comprising the amino acid sequence SEQ ID No. 102 or 103.

The two heavy chain sequences, SEQ ID Nos. 102 and 103, are corresponding to the human isotype IgG1 and IgG4, respectively.

As a consequence, a first embodiment of the invention corresponding discloses a chimeric antibody c203B6[IgG1], or a derived compound or functional fragment of same, of the invention comprises a light chain sequence comprising the amino acid sequence SEQ ID No. 101, and in that it comprises a heavy chain sequence comprising the amino acid sequence SEQ ID No. 102.

A second embodiment of the invention discloses a chimeric antibody c203B6[IgG4], or a derived compound or functional fragment of same, of the invention comprises a light chain sequence comprising the amino acid sequence SEQ ID No. 101, and in that it comprises a heavy chain sequence comprising the amino acid sequence SEQ ID No. 103. A humanized antibody is understood as referring to an antibody which contains CDR regions derived from an antibody of non-human origin, the other parts of the antibody molecule being derived from one (or more) human antibody/antibodies or germline(s). In addition, some of the residues of the segments of the skeleton (referred to as FR) can be modified in order to preserve the binding affinity (Jones et al., Nature, 321:522-525, 1986; Verhoeyen et al., Science, 239: 1534-1536, 1988; Riechmann et al., Nature, 332:323-327, 1988).

The humanized antibodies according to the invention or fragments thereof can be prepared by techniques known to the person skilled in the art (such as, for example, those described in the documents Singer et al., J. Immun. 150:2844-2857, 1992; Mountain et al., Biotechnol. Genet. Eng. Rev., 10:1-142, 1992; or Bebbington et al., Bio/Technology, 10:169-175, 1992). Such humanized antibodies according to the invention are preferred for their use in in vitro diagnostic methods or in in vivo prophylactic and/or therapeutic treatment. Other humanization techniques are also known to the person skilled in the art, such as, for example, the technique of "CDR Grafting", described by PDL, which is the subject-matter of patents EP 0 451 261, EP 0 682 040, EP 0 939 127, EP 0 566 647 or also U.S. Pat. No. 5,530,101, U.S. Pat. No. 6,180,370, U.S. Pat. No. 5,585,089 and U.S. Pat. No. 5,693,761. There may also be mentioned the U.S. Pat. Nos. 5,639,641 or also 6,054, 297, 5,886,152 and 5,877,293.

In addition, the invention is also directed at the humanized antibodies derived from the murine and chimeric antibodies described hereinbefore.

Preferably, the constant light chain and heavy chain regions derived from a human antibody are the lambda or kappa region and the gamma-1, gamma-2 or gamma-4 region, respectively.

IgG4-derived antibodies can be further modified as described by Angam et al., 1993, in order to stabilize the hinge region leading to the expression of more homogenous antibodies (Ser226 to Pro modification).

In the embodiment corresponding to the IgG1 isotype, an additional to characteristic of the antibody is that of having effector functions such as ADCC (Antibody Dependent Cellular Cytotoxicity) and/or CDC (Complement Dependent Cytotoxicity).

In addition, as will emerge from the Examples hereinbelow, the antibody to which the present invention relates differs from hitherto known antibodies in that it is capable of inhibiting the proliferation of tumour cells.

As has been stated hereinbefore, the CD151 protein belongs to the tetraspanin family and, by virtue thereof, contains 2 extracellular domains EC1 (18 amino acids, sequence [40-57]) and EC2 (109 amino acids, sequence [113-221]), also referred to as extracellular loops.

According to the present invention, the antibodies used are capable of binding to at least one epitope located in the extracellular domain. Preferably, said antibody will fix itself to the loops EC1 and/or EC2.

More particularly, in accordance with a preferred embodiment of the invention, there is described the use of at least one anti-CD151 antibody, or one of its functional fragments, capable of binding to an epitope included in the extracellular loop 1 (EC1) and/or 2 (EC2), preferably EC2, corresponding to the amino acids 40-57 and 113-221, respectively, of the CD151 protein.

The EC1 loop [40-57] contains 18 amino acids and has a theoretical weight of 2002.2 Da.

The EC2 loop [113-221] has an N-glycosylation site (residue Asn159) and 6 cysteine residues forming 3 disulfide bridges. A structural model of the EC2 loop of the tetraspanins, and especially of CD151, has been proposed on the basis of the three-dimensional structure of the EC2 loop of the tetraspanin CD81 (Seigneuret et al., 2001, J. Biol. Chem. 276, 40055-40064). According to that model, the tetraspanins have a common, relatively conserved scaffold composed of 3 α helices and a specific variable domain. For CD151, that scaffold is thought to be composed of the regions [113-157] and [209-221], and the variable domain is thought to be composed of the region [158-208].

The variable domain of the EC2 loop is thought to be more especially involved in the specific interactions of CD151 with proteins of the integrin family. Directed to mutagenesis experiments have especially shown the importance of the region [193-208], and more precisely of the tripeptide QRD [194-196] and the cysteine residue at position 192, in the association of CD151 with certain laminin receptor integrins such as integrins α3β1 or α6β4 (Kazarov et al., 2002, J. Cell Biol. 158, 1299-1309).

Even more preferably, the present invention is directed at the use of at least one anti-CD151 antibody, or one of its functional fragments, capable of binding to an epitope of the EC2 region.

In a new aspect, the present invention relates to an isolated nucleic acid, characterised in that it is selected from the following nucleic acids:

a) a DNA or RNA nucleic acid coding for an antibody, or one of its derivative compounds or functional fragments, as defined hereinbefore;

b) a nucleic acid complementary to a nucleic acid as defined hereinbefore under a);

c) a nucleic acid of at least 18 nucleotides capable of hybridising under conditions of high stringency with at least one of the nucleic acid sequences SEQ ID No. 9-16, 25-32, 38-42, 51-58, 64-68, 74-78, 82-84, 90-94, 98-100 or 104-106 or with a sequence having at least 80%, preferably 85%, 90%, 95% and 98%, identity, after optimal alignment, with said sequences.

Table 3 hereinbelow summarises the different nucleotide sequences relating to antibodies according to the invention, with the CDR sequences defined according to IMGT in bold and those defined according to Kabat in italics.

TABLE 3

|  | 203B6 (I-3920) | | 205H8 (I-3921) | | 211F3 (I-3918) | | 214B2 (I-3919) | |
| --- | --- | --- | --- | --- | --- | --- | --- | --- |
| CDR-L1 | 9 | *64* | 25 | *74* | 38 | *82* | 51 | *90* |
| CDR-L2 | 10 | *65* | 26 | *75* | 10 | *65* | 52 | *91* |
| CDR-L3 | 11 | *11* | 27 | *27* | 11 | *11* | 53 | *53* |
| Light Chain (VL) | 15 | | 31 | | 41 | | 57 | |
| Chim. VL | 104 | | | | | | 98 | |
| CDR-H1 | 12 | *66* | 28 | *76* | 12 | *66* | 54 | *92* |
| CDR-H2 | 13 | *67* | 29 | *77* | 39 | *83* | 55 | *93* |
| CDR-H3 | 14 | *68* | 30 | *78* | 40 | *84* | 56 | *94* |
| Heavy Chain (VH) | 16 | | 32 | | 42 | | 58 | |
| IgG1 Chim. VH | 105 | | | | | | 99 | |
| IgG4 Chim. VH | 106 | | | | | | 100 | |

The terms nucleic acid, nucleic or nucleic acid sequence, polynucleotide, oligonucleotide, polynucleotide sequence, nucleotide sequence, which will be used interchangeably in the present description, are understood as referring to a precise concatenation of nucleotides, modified or not, making it possible to define a fragment or region of a nucleic acid, including or not including non-natural nucleotides, which may correspond equally to a double-stranded DNA, a single-stranded DNA and to transcription products of said DNAs.

It must also be understood herein that the present invention does not relate to the nucleotide sequences in their natural chromosomic environment, that is to say in the natural state. They are sequences which have been isolated and/or purified, that is to say they have been extracted directly or indirectly, for example by copying, their environment having been at least partially modified. They are also understood herein to refer to isolated nucleic acids obtained by genetic recombination using, for example, host cells or obtained by chemical synthesis.

Nucleic sequences having a percentage identity of least 80%, preferably 85%, 90%, 95% and 98%, after optimal alignment, with a preferred sequence are understood to denote the nucleic sequences having, with respect to the reference nucleic sequence, certain modifications such as, especially, a deletion, truncation, extension, chimeric fusion and/or substitution, especially pointwise substitution. They are preferably sequences whose sequences code for the same amino acid sequences as the reference sequence, this being due to the degeneracy of the genetic code, or complementary sequences which are capable of hybridising specifically with the reference sequences, preferably under conditions of high stringency, especially as defined hereinbelow.

Hybridisation under conditions of high stringency means that the conditions for temperature and ionic strength are so selected that they make it possible for hybridisation to be maintained between two complementary fragments of DNA. By way of illustration, conditions of high stringency of the hybridisation step for the purpose of defining the polynucleotide fragments described hereinbefore are advantageously as follows:

DNA-DNA or DNA-RNA hybridisation is carried out in two steps: (1) Prehybridization at 42° C. for 3 hours in phosphate buffer (20 mM, pH 7.5) containing 5×SSC (1×SSC corresponds to a solution of 0.15M NaCl+0.015M sodium citrate), 50% formamide, 7% sodium dodecyl sulfate (SDS), 10×Denhardt's, 5% dextran sulfate and 1% salmon sperm DNA; (2) hybridisation proper for 20 hours at a temperature depending on the size of the probe (i.e.: 42° C. for a probe of size >100 nucleotides) followed by 2 washings of 20 minutes at 20° C. in 2×SSC+2% SDS, 1 washing of 20 minutes at 20° C. in 0.1×SSC+0.1% SDS. The final washing is carried out in 0.1×SSC+0.1% SDS for 30 minutes at 60° C. for a probe of size >100 nucleotides. The high-stringency conditions described hereinbefore for a polynucleotide of defined size can be adapted by the person skilled in the art for oligonucleotides of larger or smaller size, in accordance with the teaching of Sambrook et al., (1989, Molecular cloning: a laboratory manual. 2nd Ed. Cold Spring Harbor).

The invention relates also to a vector comprising a nucleic acid according to the present invention.

The invention is directed especially at cloning and/or expression vectors containing a nucleotide sequence according to the invention.

The vectors according to the invention preferably comprise elements which allow the expression and/or secretion of the nucleotide sequences in a particular host cell. The vector must then comprise a promoter, translation initiation and termination signals and also appropriate transcription regulation regions. It must be capable of being maintained in stable manner in the host cell and it may optionally have particular signals specifying the secretion of the translated protein. These various elements will be selected and optimised by the person skilled in the art as a function of the cell host used. To that effect, the nucleotide sequences according to the invention can be inserted into self-replicating vectors within the selected host or can be integrative vectors of the selected host.

Such vectors are prepared by methods customarily used by the person skilled in the art, and the resulting clones can be introduced into a suitable host by standard methods such as lipofection, electroporation, heat shock or chemical methods.

The vectors according to the invention are, for example, vectors of plasmid or viral origin. They are useful in transforming host cells in order to clone or express the nucleotide sequences according to the invention.

The invention also includes the host cells transformed by or containing a vector according to the invention.

The cell host may be selected from prokaryotic or eukaryotic systems, for example, bacterial cells, but also yeast cells or animal cells, especially mammalian cells. Insect cells or plant cells can also be used.

The invention relates also to animals, with the exception of human beings, comprising a transformed cell according to the invention.

In accordance with another aspect, the invention relates to a method of producing an antibody, or one of its functional fragments, according to the invention, characterised in that it comprises the following steps:

a) culture of a host cell according to the invention in a suitable culture medium and under suitable culture conditions; and b) recovery of said antibodies, or a functional fragment thereof, thereby produced, from the culture medium or from said cultured cells.

The transformed cells according to the invention can be used in methods for the preparation of recombinant polypeptides according to the invention. The methods for the preparation of a polypeptide according to the invention in recombinant form, characterised in that they employ a vector and/or a cell transformed by a vector according to the invention, are themselves included in the present invention. Preferably, a cell transformed by a vector according to the invention is cultured under conditions enabling the expression of said polypeptide, and said recombinant peptide is recovered.

As has been stated, the cell host may be selected from prokaryotic or eukaryotic systems. In particular, it is possible to identify nucleotide sequences according to the invention which facilitate secretion in such a prokaryotic or eukaryotic system. A vector according to the invention carrying such a sequence can therefore be advantageously used in the production of recombinant proteins that are intended to be secreted. Indeed, purification of these recombinant proteins of interest will be facilitated by the fact that they are present in the supernatant of the cell culture rather than in the interior of the host cells.

It is also possible to prepare the polypeptides according to the invention by chemical synthesis. Such a preparation method is also included in the subject-matter of the invention. The person skilled in the art knows methods of chemical synthesis, for example techniques employing solid phases (see, especially, Steward et al., 1984, Solid phase peptides synthesis, Pierce Chem. Company, Rockford, 111, 2nd Ed., (1984)) or techniques using partial solid phases, by means of condensation of fragments or by conventional synthesis in solution. The polypeptides obtained by chemical synthesis, which may contain corresponding non-natural amino acids, are also included in the invention.

The antibodies, or one of their derivative compounds or functional fragments, capable of being obtained by a method according to the invention are also included in the present invention.

According to yet another aspect, the present invention relates to an antibody as described hereinbefore, characterised in that it is, additionally, bispecific, that is to say capable of binding specifically to a human protein or human receptor other than CD151.

The bispecific, or bifunctional, antibodies constitute a second generation of monoclonal antibodies in which two different variable regions are combined in the same molecule (Hollinger and Bohlen 1999 Cancer and metastasis rev. 18: 411-419). Their usefulness has been demonstrated both in the diagnostic field and in the therapeutic field by their ability to recruit new effector functions or to target a plurality of molecules on the surface of tumour cells. These antibodies can be obtained by chemical methods (Glennie M J et al. 1987 J. Immunol. 139, 2367-2375; Repp R. et al. 1995 J. Hemat. 377-382) or somatic methods (Staerz U. D. and Bevan M. J. 1986 PNAS 83, 1453-1457; Suresh M. R. et al. 1986 Method Enzymol. 121: 210-228) but also, and preferably, by genetic engineering techniques which make it possible to force heterodimerization and thereby facilitate the method of purifying the sought antibody (Merchand et al. 1998 Nature Biotech. 16: 677-681).

These bispecific antibodies can be constructed as whole IgGs, as bispecific Fab'2s, as Fab'PEGs or as diabodies or as bispecific scFvs but also as a tetravalent bispecific antibody in which two fixing sites are present for each antigen targeted (Park to et al. 2000 Mol. Immunol. 37(18): 1123-30) or fragments thereof as described hereinbefore.

Besides an economic advantage due to the fact that production and administration of a bispecific antibody is less onerous than production of two specific antibodies, the use of such bispecific antibodies has the advantage of reducing the toxicity of the treatment. The use of a bispecific antibody makes it possible, in fact, to reduce the overall amount of circulating antibodies and, as a result, the possible toxicity.

In a preferred embodiment of the invention, the bispecific antibody is a divalent or tetravalent antibody.

Finally, the present invention is directed to the antibody, or one of its derivative compounds or functional fragments, as described hereinbefore, as a medicament.

The invention relates also to a pharmaceutical composition comprising, as active ingredient, a compound consisting of an antibody, or one of its derivative compounds or functional fragments, according to the invention. Preferably, there is added to said antibody an excipient and/or a pharmaceutically acceptable carrier.

According to yet another embodiment, the present invention relates also to a pharmaceutical composition as described hereinbefore which additionally comprises, as a combination product for simultaneous, separate or time-staggered use, at least one other antibody, a cytotoxic/cytostatic agent, a cell toxin or a radioelement.

"Simultaneous use" is understood as the administration of the two compounds of the composition according to the invention contained in one and the same pharmaceutical form.

"Separate use" is understood as the administration, at the same time, of the two compounds of the composition according to the invention contained in separate pharmaceutical forms.

"Time-staggered use" is understood as the successive administration of the two compounds of the composition according to the invention, each contained in a separate pharmaceutical form.

In general manner, the composition according to the invention considerably increases the efficacy of the cancer treatment. In other words, the therapeutic effect of the antibody according to the invention is potentiated in unexpected manner by the to administration of a cytotoxic agent. Another major subsequent advantage produced by a composition according to the invention relates to the possibility of using lower effective doses of active ingredient, which makes it possible to avoid or reduce the risks of secondary effects appearing, especially the effect of the cytotoxic agent. Moreover, this composition according to the invention should make it possible to achieve the expected therapeutic effect more rapidly.

"Anti-cancer therapeutic agents" or "cytotoxic agents" should be understood as substances which, when administered to a patient, treats or prevents the development of the cancer in the patient. By way of non-limiting example of such agents there may be mentioned "alkylating" agents, antimetabolites, anti-tumour antibiotics, mitotic inhibitors, chromatin function inhibitors, anti-angiogenesis agents, anti-oestrogens, anti-androgens or immunomodulators.

Such agents are, for example, mentioned in the VIDAL, on the page devoted to oncology and haematology in the column "Cytotoxiques" (English: cytotoxic agents); such cytotoxic compounds mentioned by way of reference to that document are mentioned here as preferred cytotoxic agents.

"Alkylating agents" refer to any substance which is capable of covalently binding to or alkylating any molecule, preferably a nucleic acid (e.g.: DNA), within a cell. As examples of such alkylating agents there may be mentioned nitrogen mustards such as mechlorethamine, chlorambucil, melphalan hydrochloride, pipobroman, prednimustine disodium phosphate or estramustine; oxazophorines such as cyclophosphamide, altretamine, trofosfamide, sulfofosfamide or ifosfamide; aziridines or ethylene-imines such as thiotepa, triethyleneamine or altetramine; nitrosoureas such as carmustine, streptozocin, fotemustine or lomustine; alkyl sulfonates such as busulfan, treosulfan or improsulfan; triazenes such as dacarbazine; and also platinum complexes such as cisplatin, oxaliplatin or carboplatin.

"Antimetabolites" refer to substances which block cell growth and/or cell metabolism by interfering with certain activities, generally DNA synthesis. By way of example of antimetabolites there may be mentioned methotrexate, 5-fluorouracil, floxuridine, 5-fluorodeoxyuridine, capecitabine, cytarabine, fludarabine, cytosine arabinoside, 6-mercaptopurine (6-MP), 6-thioguanine (6-TG), chlorodeoxyadenosine, 5-azacytidine, gemcitabine, cladribine, deoxycoformycin and pentostatin.

"Anti-tumour antibiotics" refer to compounds which can prevent or inhibit the synthesis of DNA, of RNA and/or of proteins. Examples of such anti-tumour antibiotics include doxorubicin, daunorubicin, idarubicin, valrubicin, mitoxantrone, dactinomycin, mithramycin, plicamycin, mitomycin C, bleomycin and procarbazine.

"Mitotic inhibitors" prevent the normal progression of the cell cycle and mitosis. In general, the microtubule inhibitors or "taxoids" such as paclitaxel and docetaxel are capable of inhibiting mitosis. The vinca alkaloids such as vinblastine, vincristine, vindesine and vinorelbine are also capable of inhibiting mitosis.

"Chromatin function inhibitors" or "topoisomerase inhibitors" refer to substances which inhibit the normal function of chromatin remodelling proteins such as topoisomerases I and II. Examples of such inhibitors include, for topoisomerase I, camptothecin and also its derivatives such as irinotecan or topotecan and, for topoisomerase II, etoposide, etiposide phosphate and teniposide.

"Anti-angiogenesis agents" refer to any drug, compound, substance or agent which inhibits the growth of blood vessels. Examples of anti-angiogenesis agents include, without any limitation, razoxin, marimastat, batimastat, prinomastat, tanomastat, ilomastat, CGS-27023A, halofuginone, COL-3, neovastat, BMS-275291, thalidomide, CDC 501, DMXAA, L-651582, squalamine, endostatin, SU5416, SU6668, interferon-alpha, EMD121974, interleukin-12, IM862, angiostatin and vitaxin.

"Anti-oestrogens" or "anti-oestrogen agents" refer to any substance which reduces, antagonises or inhibits the action of oestrogens. Examples of such agents are tamoxifen, toremifene, raloxifene, droloxifene, iodoxyfene, anastrozole, letrozole and exemestane.

"Anti-androgens" or "anti-androgen agents" refer to any substance which reduces, antagonises or inhibits the action of an androgen. Examples of anti-androgens are flutamide, nilutamide, bicalutamide, spironolactone, cyproterone acetate, finasteride and cimitidine.

Immunomodulators are substances which stimulate the immune system. Examples of such immunomodulators include interferons, interleukins such as aldesleukin, OCT-43, denileukin diflitox or interleukin-2, tumour necrosis factors such as tasonermin, or other types of immunomodulators such as lentinan, sizofuran, roquinimex, pidotimod, pegademase, thymopentin, poly I:C, or levamisole in combination with 5-fluorouracil.

For further details, the person skilled in the art will be able to refer to the manual published by the French Association of Teachers of Therapeutic Chemistry entitled "Traité de chimie thérapeutique, Vol. 6, Médicaments antitumoraux et perspectives dans le traitement des cancers, ed. TEC & DOC, 2003".

In an especially preferred embodiment, said composition in the form of a combination product according to the invention is characterised in that said cytotoxic agent is chemically bound to said antibody for simultaneous use.

In an especially preferred embodiment, said composition according to the invention is characterised in that said cytotoxic/cytostatic agent is selected from spindle inhibitor or stabiliser agents, preferably vinorelbine and/or vinflunine and/or vincristine.

In order to facilitate binding between said cytotoxic agent and said antibody according to the invention, it will be possible, especially, to introduce spacer molecules between the two compounds to be bound, e.g. poly(alkylene)glycols such as polyethyleneglycol, or also amino acids, or, in another embodiment, to use active derivatives of said cytotoxic agents into which there will have been introduced functions capable of reacting with said antibody according to the invention. These binding techniques are will known to the person skilled in the art and will not be elaborated upon in the present description.

According to another aspect, the invention relates to a composition characterised in that one, at least, of said antibodies, or one of their derivative compounds or functional fragments, is conjugated with a cell toxin and/or a radioelement.

Preferably, said toxin or said radioelement is capable of preventing the growth or proliferation of the tumour cell, especially of totally inactivating said tumour cell.

Preference is also given to said toxin being an enterobacterial toxin, especially *Pseudomonas* exotoxin A.

The radioelements (or radioisotopes) employed in therapy, preferably conjugated with the antibody, are radioisotopes which emit gamma rays, preferably iodine$^{131}$, yttrium$^{90}$, gold$^{199}$, palladium$^{100}$, copper$^{67}$, bismuth$^{217}$ and antimony$^{211}$. Radioisotopes which emit beta and alpha rays may also be used in therapy.

A toxin or radioelement conjugated with at least one antibody, or a functional fragment thereof, according to the invention is understood to refer to any means making it possible to bind said toxin or said radioelement to said at least one antibody, especially by covalent binding between the two compounds, with or without introduction of a linking molecule.

Among the agents allowing chemical (covalent), electrostatic or non-covalent linkage of all or some of the conjugate's elements there may be mentioned, very especially, benzoquinone, carbodiimide and, more especially, EDC (1-ethyl-3-[3-dimethylaminopropyl]-carbodiimide hydrochloride), dimaleimide, dithiobis-nitro-benzoic acid (DTNB), N-succinimidyl S-acetyl thioacetate (SATA), agents referred to as "bridging" agents having one or more groups, with one or more phenylazide groups, reacting with ultraviolet (UV) and very preferably N-[-4-(azidosalicylamino)butyl]-3'-(2'-pyridyldithio)propionamide (APDP), N-succinimidyl 3-(2-pyridyldithio)propionate (SPDP) and 6-hydrazino-nicotinamide (HYNIC).

Another form of binding, very especially for radioelements, can consist of using a bifunctional ion chelator.

Among those chelators there may be mentioned the chelators derived from EDTA (ethylenediaminetetraacetic acid) or DTPA (diethylenetriaminepentaacetic acid) that have been developed for binding metals, especially radioactive metals, and immunoglobulins. Accordingly, DTPA and its derivatives can be substituted with different groups on the carbon chain so as to increase the stability and rigidity of the ligand-metal complex (Krejcarek et al. (1977); Brechbiel et al. (1991); Gansow (1991); U.S. Pat. No. 4,831,175).

For example, DTPA (diethylenetriaminepentaacetic acid) and its derivatives, which has long been used very widely in medicine and biology either in its free form or in the form of a complex with a metal ion, has the noteworthy characteristic of forming stable chelates with metal ions and of being bound to proteins of therapeutic or diagnostic interest such as antibodies for the development of radioimmunoconjugates in cancer therapy (Meases et al., (1984); Gansow et al. (1990)).

Also preferably, said at least one antibody forming said conjugate according to the invention is selected from its functional fragments, especially fragments lacking the Fc component such as scFv fragments.

The present invention additionally comprises use of the composition according to the invention in the preparation of a medicament intended for the prevention or treatment of cancer.

The present invention relates also to the use of an antibody, or one of its derivative compounds or functional fragments, preferably humanized, and/or of a composition according to the invention in the preparation of a medicament intended to inhibit the proliferation of tumour cells. In general manner, the present invention relates to the use of an antibody, or one of its derivative compounds or functional fragments, preferably humanized, and/or of a composition according to the invention in the preparation of a medicament intended for the prevention or treatment of cancer.

Among the cancers that may be prevented and/or treated, preference is given to prostate cancer, osteosarcomas, lung cancer, breast cancer, endometrial cancer, colon cancer, multiple myeloma or ovarian cancer, pancreatic cancer or any other cancer.

Preferably, said cancer is a cancer selected from prostate cancer, lung cancer, colon cancer, breast cancer and/or pancreatic cancer.

In accordance with yet another aspect, the present invention relates to the use of the antibody according to the invention in a, preferably in vitro, diagnostic method for diseases associated with a level of expression of CD 151. More especially, the invention is directed to an in vitro diagnostic method for diseases having overexpression or underexpression of the CD151 protein, starting from a biological sample in which the abnormal presence of the CD151 protein is suspected, said method consisting of placing said biological sample in contact with an antibody according to the invention, it being possible for said antibody, where appropriate, to be labelled.

Preferably, said diseases associated with the CD151 protein in said diagnostic method will be cancers.

Said antibody, or one of its functional fragments, can be in the form of an immunoconjugate or antibody labelled in order to obtain a detectable and/or quantifiable signal.

The antibodies labelled according to the invention or their functional fragments include, for example, antibodies referred to as immunoconjugates which can be conjugated, for example, with enzymes such as peroxidase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase or with a molecule such as biotin, digoxigenin or 5-bromo-deoxyuridine. Fluorescent labels can also be conjugated with the antibodies, or their functional fragments, according to the invention and include, especially, fluorescein and its derivatives, fluorochrome, rhodamine and its derivatives, GFP (Green Fluorescent Protein), dansyl, umbelliferone etc. In such conjugates, the antibodies of the invention or their functional fragments can be prepared by methods known to the person skilled in the art. They can be bound to the enzymes or fluorescent labels directly or by way of a spacer group or a linkage group such as a polyaldehyde, e.g. glutaraldehyde, ethylenediaminetetraacetic acid (EDTA) or diethylenetriaminepentaacetic acid (DPTA), or in the presence of binding agents such as those mentioned hereinbefore for the therapeutic conjugates. Conjugates comprising fluorescein-type labels can be prepared by reaction with an isothiocyanate.

Other conjugates can also include chemoluminescent labels such as luminol and dioxetanes, bioluminescent labels such as luciferase and luciferin, or also radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$, iodine$^{131}$. The methods known to the person skilled in the art that exist for binding radioisotopes to the antibodies, either directly or via a chelating agent such as EDTA or DTPA mentioned hereinbefore, can be used for the radioelements in diagnostics. There may also therefore be mentioned labelling with [I$^{125}$]Na by the chloramine T technique [Hunter W. M. and Greenwood F. C. (1962) Nature 194:4951 or also with technetium$^{99m}$ by the technique of Crockford et al. (U.S. Pat. No. 4,424,200) or fixed via DTPA as described by Hnatowich (U.S. Pat. No. 4,479,930).

The invention relates also to the use of an antibody according to the invention in the preparation of a medicament intended for the specific targeting of a biologically active compound at cells expressing or overexpressing the CD151 protein.

A biologically active compound is understood herein as referring to any compound capable of modifying, especially inhibiting, the activity of cells, especially their growth, their proliferation, or the transcription or translation of genes.

The invention relates also to an in vivo diagnostic reagent comprising an antibody according to the invention, or one of its functional fragments, preferably labelled, especially radiolabelled, and to its use in medical imaging, especially in the detection of cancer associated with the expression or overexpression of the CD151 protein by a cell.

The invention relates also to a composition in the form of a combination product or to an anti-CD151/toxin or radioelement conjugate, according to the invention, as a medicament.

Preferably, to said composition in the form of a combination product or to said conjugate according to the invention there will be added an excipient and/or a pharmaceutically acceptable carrier.

In the present description, a pharmaceutically acceptable carrier is understood as referring to a compound or combination of compounds included in a pharmaceutical composition which does not give rise to secondary reactions and which, for example, makes it possible to facilitate the administration of the active compound(s), to increase the life or efficacy thereof in the body, to increase the solubility thereof in solution or to improve its storage. Such pharmaceutically acceptable carriers are well-known and will be adapted by the person skilled in the art as a function of the nature and mode of administration of the selected active compound(s).

Preferably, those compounds will be administered by a systemic route, especially the intravenous route, by the intramuscular, intradermic, intraperitoneal or subcutaneous route, or by the oral route. More preferably, the composition comprising the antibodies according to the invention will be administered on a plurality of occasions staggered over time.

Their optimal modes of administration, dosage regimens and galenic forms can be determined according to criteria generally taken into consideration in establishing a suitable treatment for a patient such as, for example, the age or bodyweight of the patient, the severity of his or her general condition, the tolerability of the treatment and the secondary effects established.

The invention relates accordingly to the use of an antibody, or one of its functional fragments, in the preparation of a medicament intended for specifically targeting a biologically active compound at cells expressing or overexpressing CD151.

Other characteristics and advantages of the invention will emerge in the remainder of the description with the Examples and Figures, for which the legends are given hereinbelow.

LEGENDS FOR FIGURES

The patent or application file contains at least one drawing executed in color. Copies of this patent or patent application publication with color drawings will be provided by the Office upon request and payment of the necessary fee.

FIG. 1 shows the nucleotide (SEQ ID No. 107) and protein (SEQ ID No. 108) sequences of the human CD151 protein, on which sequences there are shown the EC1 and EC2 loops.

FIG. 3 shows the respective variable heavy chain nucleotide (SEQ ID NO. 16) and protein (SEQ ID NO. 8) sequences and variable light chain nucleotide (SEQ ID NO. 15) and protein (SEQ ID NO. 7) sequences of antibody 203B6 according to the invention. The CDRs defined according to the IMGT system are shown underlined and in bold whereas the CDRs defined according to Kabat are shown in boxes.

FIG. 4 shows the respective variable heavy chain nucleotide (SEQ ID NO. 32) and protein (SEQ ID NO. 24) sequences and variable light chain nucleotide (SEQ ID NO. 31) and protein (SEQ ID NO. 23) sequences of antibody 205H8 according to the invention. The CDRs defined according to the IMGT system are shown underlined and in bold whereas the CDRs defined according to Kabat are shown in boxes.

FIG. 5 shows the respective variable heavy chain nucleotide (SEQ ID NO. 42) and protein (SEQ ID NO. 41) sequences and variable light chain nucleotide (SEQ ID NO. 15) and protein (SEQ ID NO. 36) sequences of antibody 211F3 according to the invention. The CDRs defined according to the IMGT system are shown underlined and in bold whereas the CDRs defined according to Kabat are shown in boxes.

FIG. 6 shows the respective variable heavy chain nucleotide (SEQ ID NO. 58) and protein (SEQ ID NO. 50) sequences and variable light chain nucleotide (SEQ ID NO. 57) and protein (SEQ ID NO. 49) sequences of antibody 214B2 according to the invention. The CDRs defined according to the IMGT system are shown underlined and in bold whereas the CDRs defined according to Kabat are shown in boxes.

FIGS. 14A-14D illustrate the anti-tumour activity of anti-CD151 monoclonal antibodies in the PC3 prostate tumour xenograft model. The PC3 cells were grafted into Swiss Nude mice (n=6) by the subcutaneous route. Five days after grafting of the cells, the mice receive, by the i.p. route, a challenge dose of 2 mg/mouse of the antibody under test followed by two administrations per week of a dose of 1 mg/mouse of that antibody. The tumour volume is determined by the formula $\pi/6 \times \text{length} \times \text{width} \times \text{thickness}$.

Figure 15A:
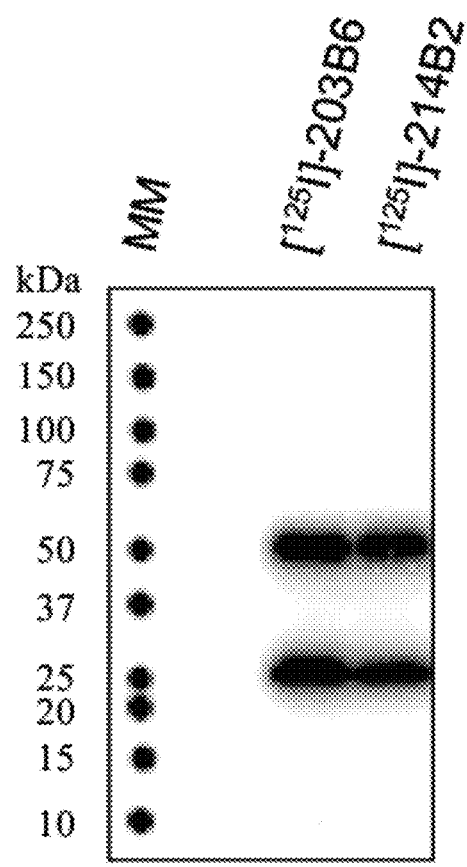
Figure 15B:
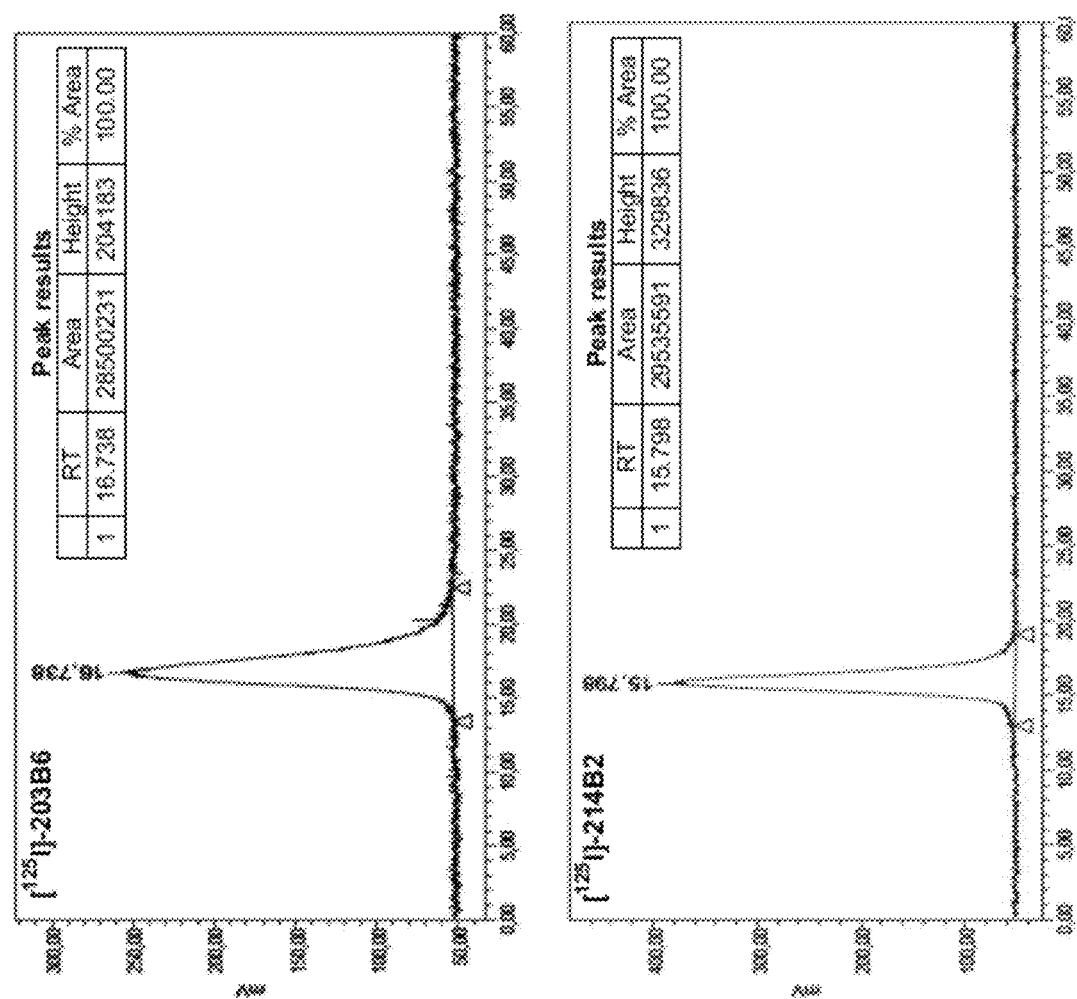

FIGS. 15A-15B show the analysis of the antibodies 203B6 and 214B2 radiolabelled with iodine 125, with (A) Autoradiography after SDS-PAGE electrophoresis under reductive conditions and (B) Analysis by molecular-sieve chromatography.

Figure 16A:
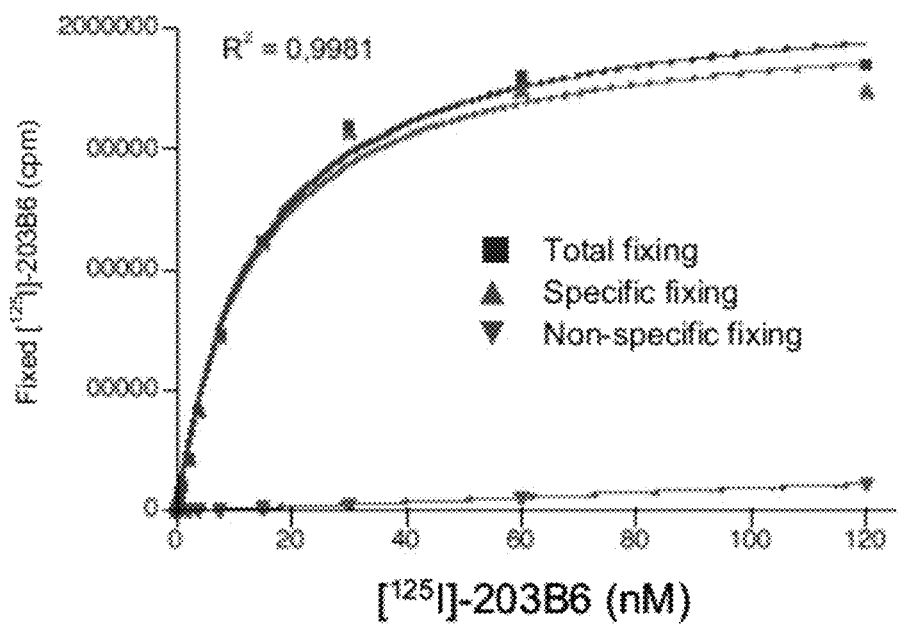
Figure 16B:
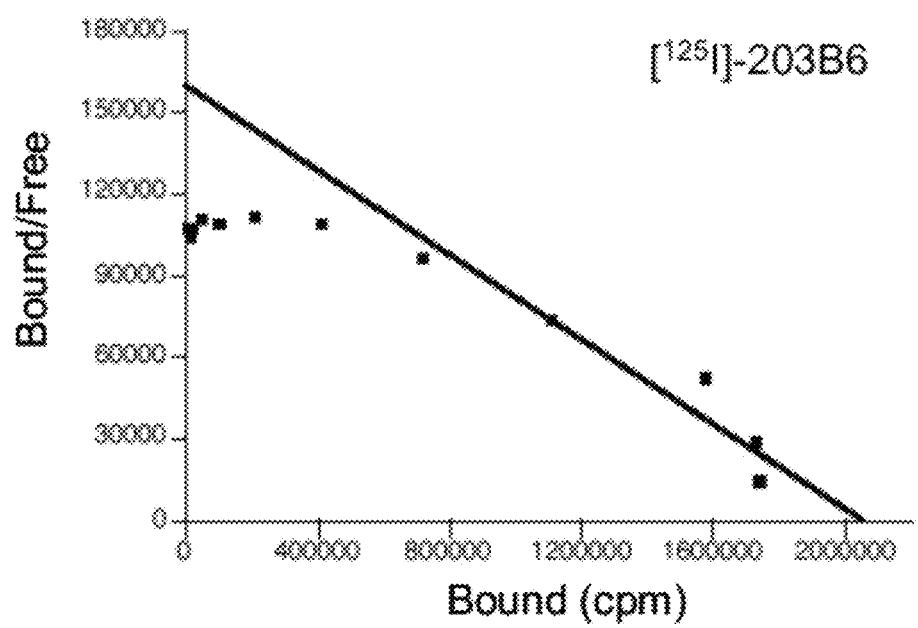

FIGS. 16A-16B illustrate the study of the fixing of the radiolabelled 203B6 antibody to PC3 cells: Determination of the affinity constant at equilibrium with (A) Saturation curve and (B) Scatchard plot.

Figure 17A:
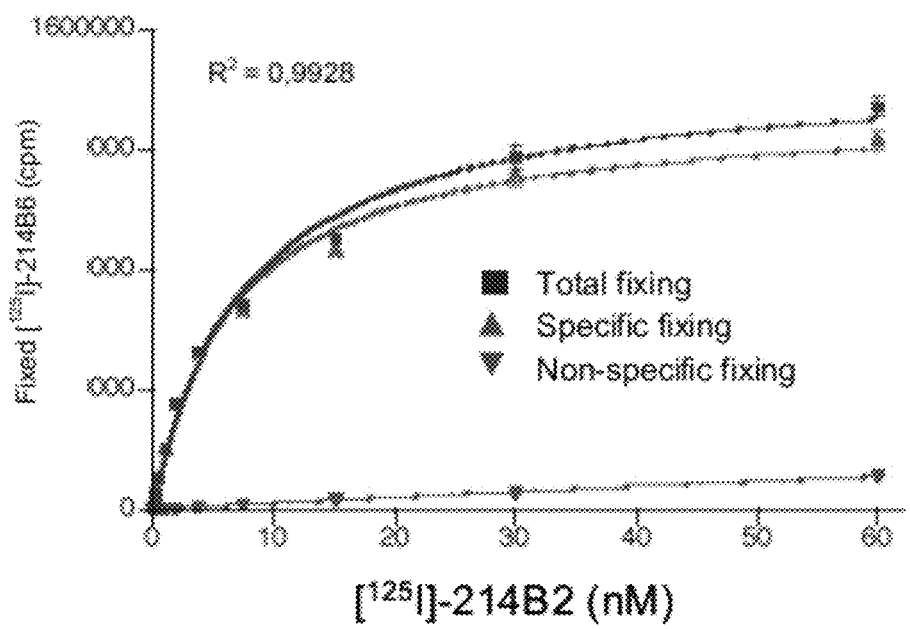
Figure 17B:
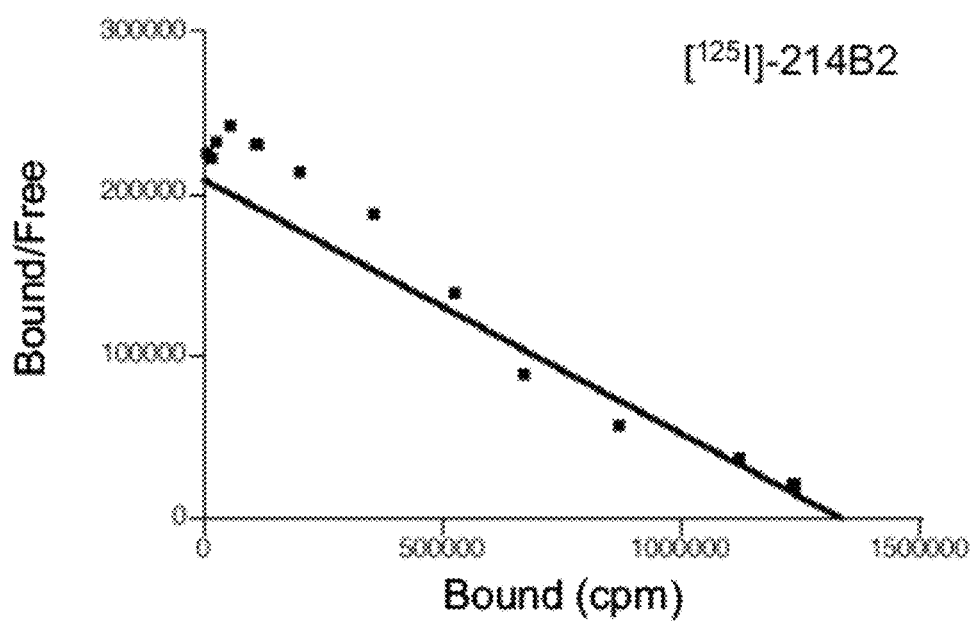

FIG. 17A-17B illustrate the study of the fixing of the radiolabelled 214B2 antibody to PC3 cells: Determination of the affinity constant at equilibrium with (A) Saturation curve and (B) Scatchard plot.

Figure 18A:
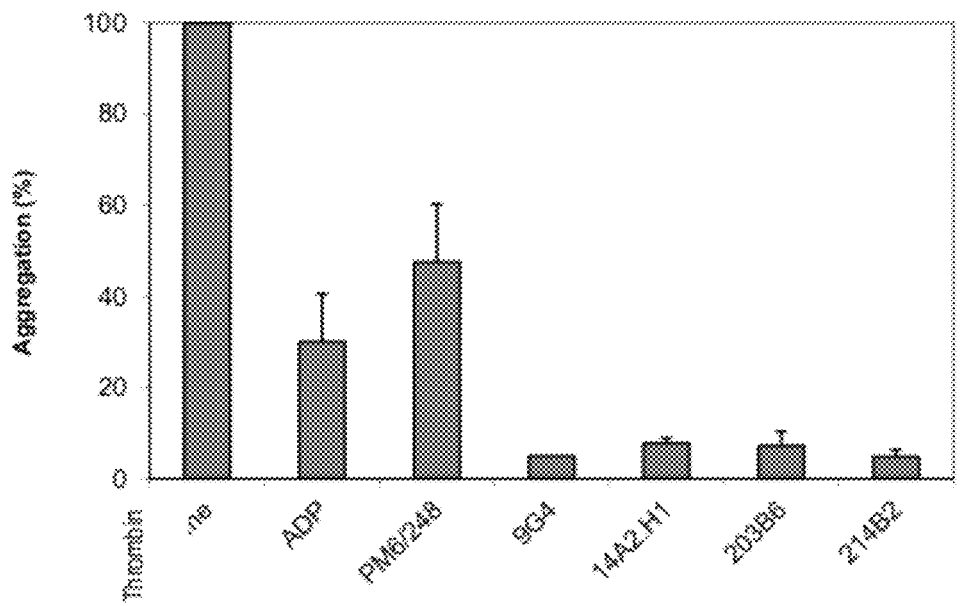
Figure 18B:
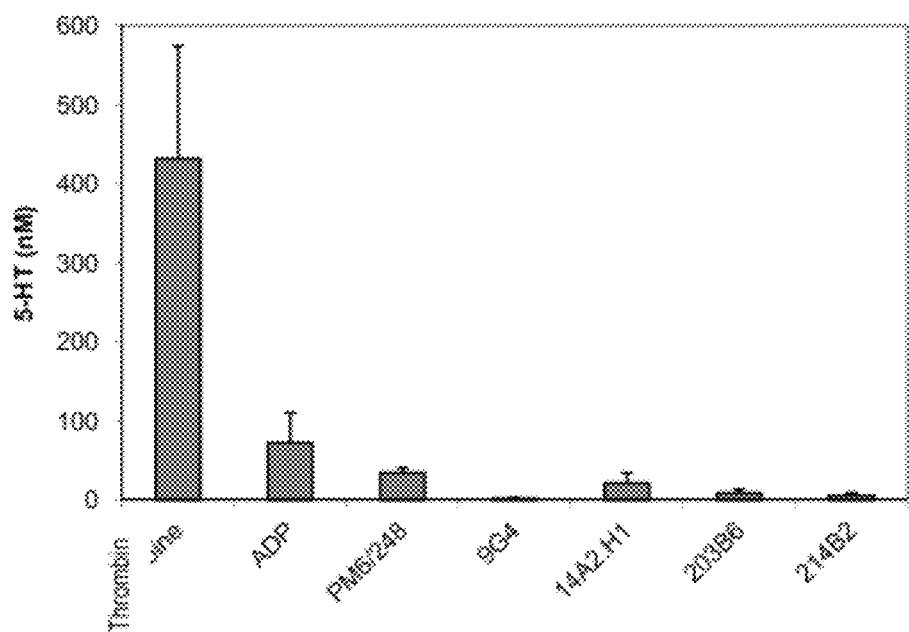

FIGS. 18A-18B show the effect of the anti-CD151 antibodies on platelet functions, with (A) Platelet aggregation and (B) Platelet activation (release of serotonin).

Figure 19:
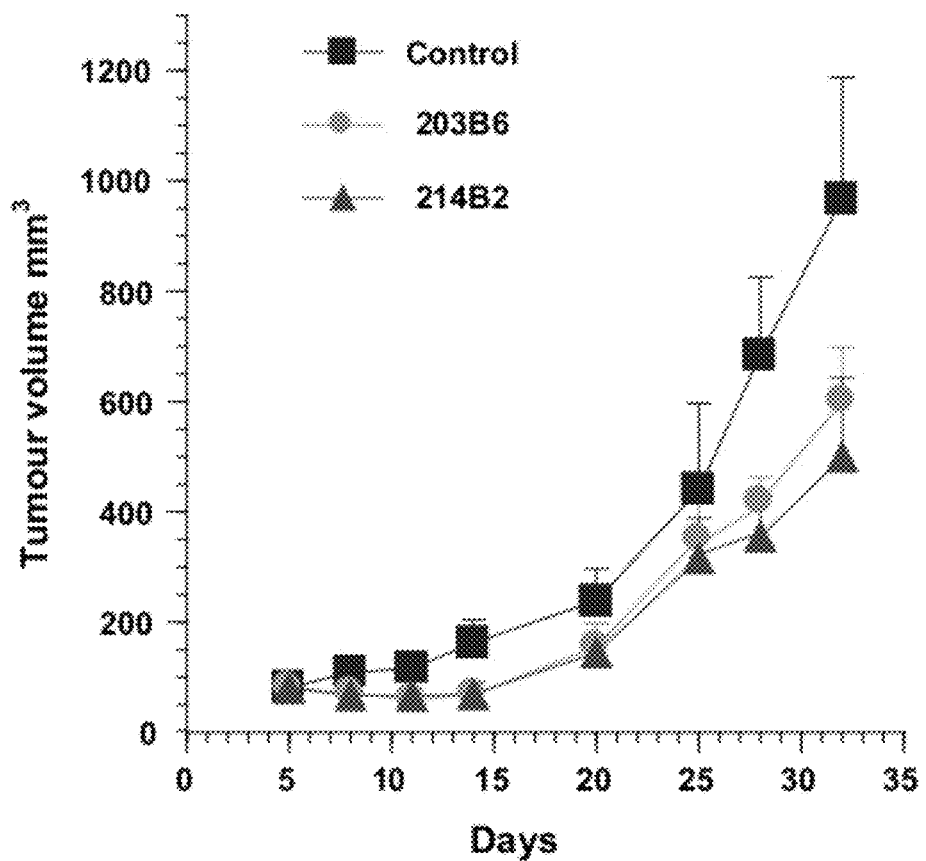

FIG. 19 shows the effect of anti-CD151 antibodies on the tumour growth, in vivo, of NCI-H441 cells.

Figure 20A:
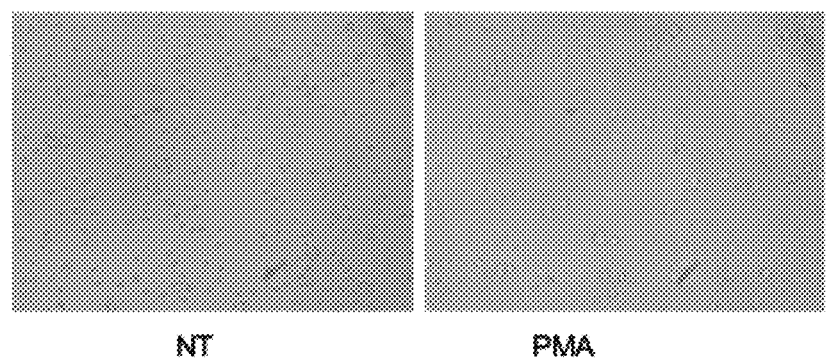
Figure 20B:
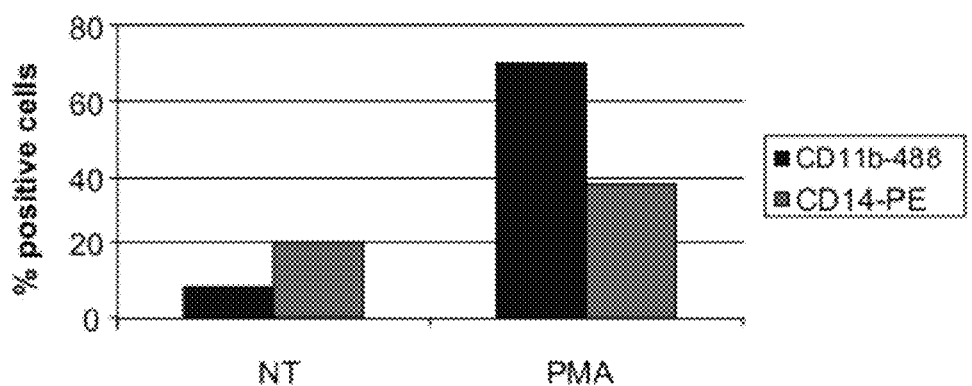
Figure 20C:
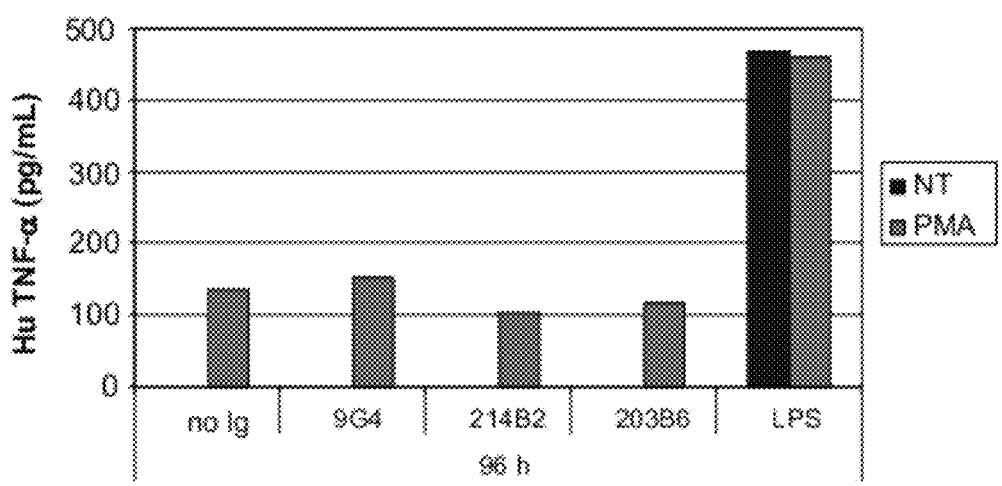

FIGS. 20A-20C illustrate the phenotype A) and differentiation markers B) of THP-1 cells cultured in the absence or presence of PMA. C) Effect of anti-CD151 antibodies (214B2 and 203B6) on the secretion of TNF by THP-1 cells cultured in the absence or presence of PMA. The antibody 9G4 is used as isotype control and LPS as positive activation control.

Figure 21A:
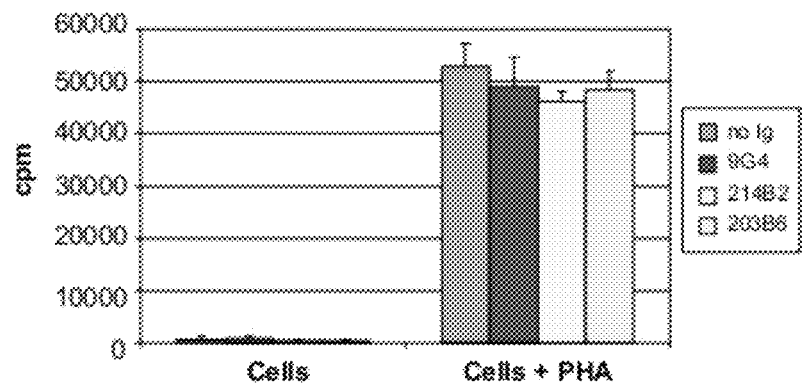
Figure 21B:
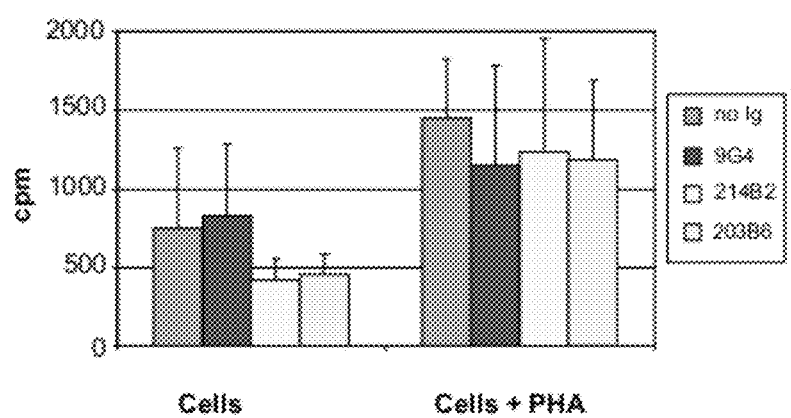

FIGS. 21A-21B show the effect of the antibodies 241B2 and 203B6 on antigen presentation. A) polyclonal proliferation control, B) antigen-specific proliferation.

Figure 22:
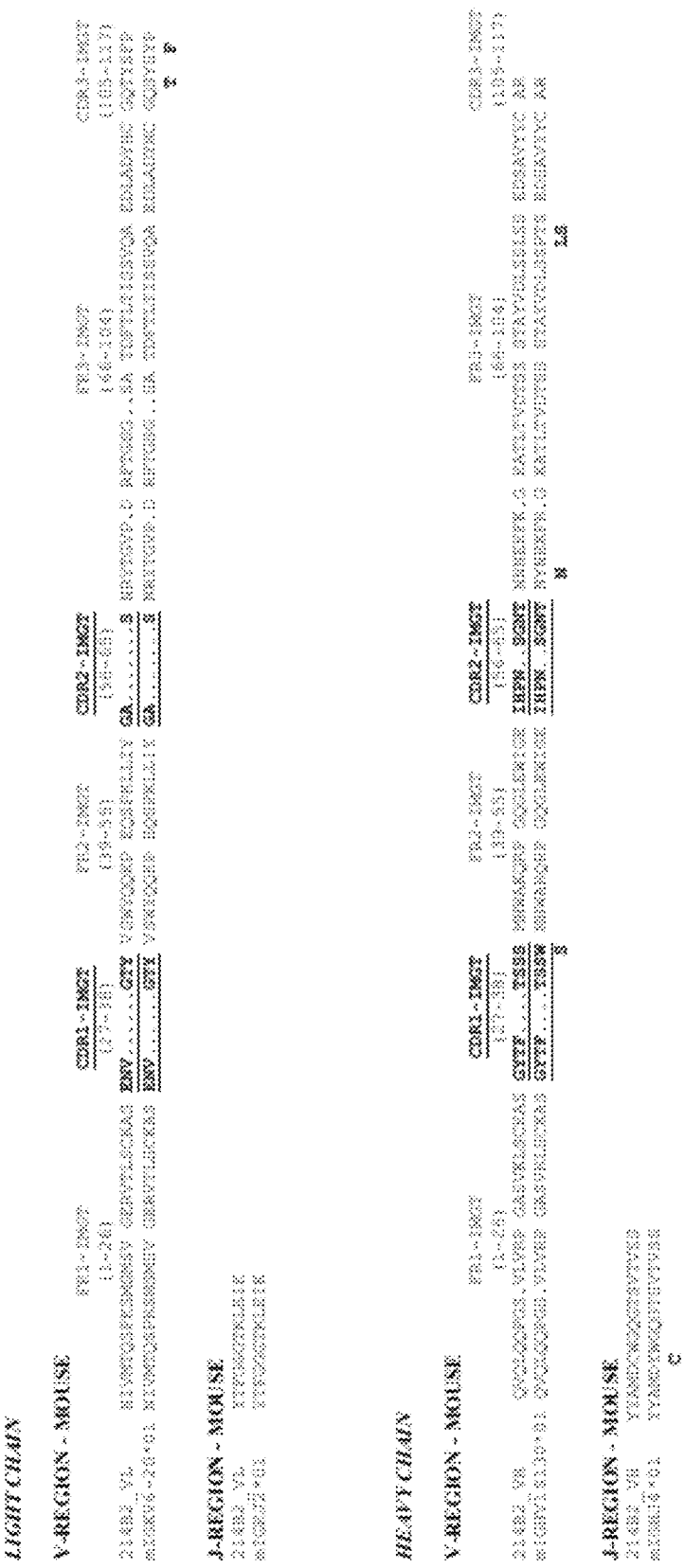

FIG. 22 represents the alignment between mouse 214B2 V- and J-regions and closest mouse germline genes for heavy and light chains variable regions. The following amino acid sequences are represented:

Variable light chain of mouse 214B2: sequence from the V-gene (amino acids 1-95 of SEQ ID No. 49) and the J-gene (amino acids 96-107 of SEQ ID No. 49) regions.

Variable light chain of mouse IGKV6-20*01 V-gene (SEQ ID No. 109) and mouse IGKJ2*01 J-gene (SEQ ID No. 110) regions.

Variable heavy chain of mouse 214B2: sequence from the V-gene (amino acids 1-98 of SEQ ID No. 50) and the J-gene (amino acids 103-119 of SEQ ID No. 50) regions.

Variable heavy chain of mouse IGHV1S130*01 V-gene (SEQ ID No. 111) and mouse IGHJ4*01 J-gene (SEQ ID No. 112) regions.

Figure 23:
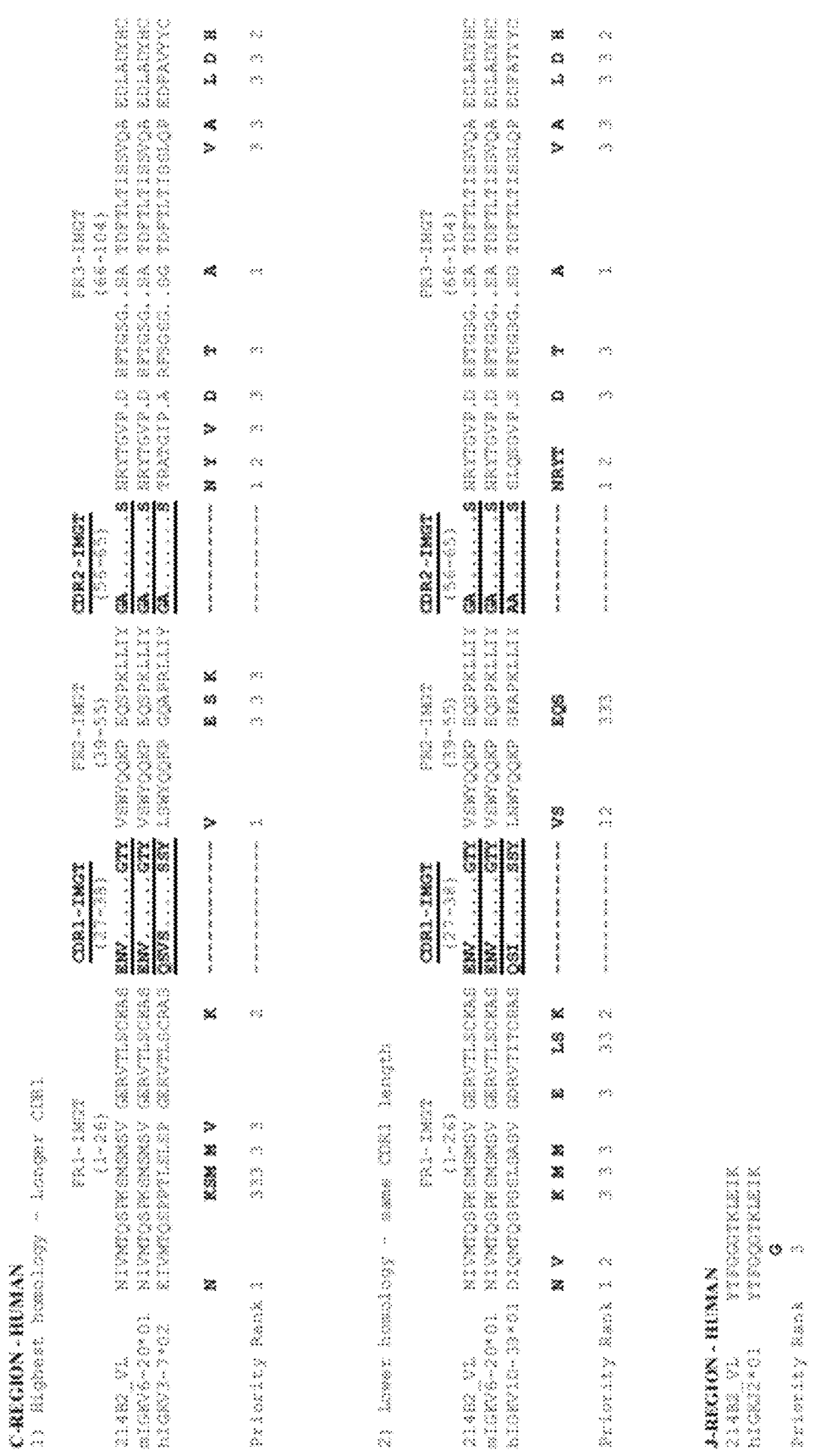

FIG. 23 illustrates the humanization of 214B2 light chain with the different Priority Ranking: #1 is high priority (putative high impact on target recognition, CDR presentation and overall 3D structure); #2 is medium priority; and #3 is low priority (putative low impact on target recognition, CDR presentation and overall 3D structure).

The following SEQ ID Nos. apply for the represented aligned V-regions:
1) Highest homology: 214B2 VL (amino acids 1-88 from SEQ ID No. 49), mIGKV6-20*01 (SEQ ID No. 113), and hIGKV3-7*02 (SEQ ID No. 114).
2) Lower homology: 214B2 VL (amino acids 1-88 from SEQ ID No. 49), mIGKV6-2001 (SEQ ID No. 113), and hIGKV1D-39*01 (SEQ ID No. 115).

The following SEQ ID NOs. apply for the represented J-regions: 214B2 VL (amino acids 103-119 from SEQ ID No. 50) and hIGKJ2*01 (SEQ ID No. 116).

Figure 24:
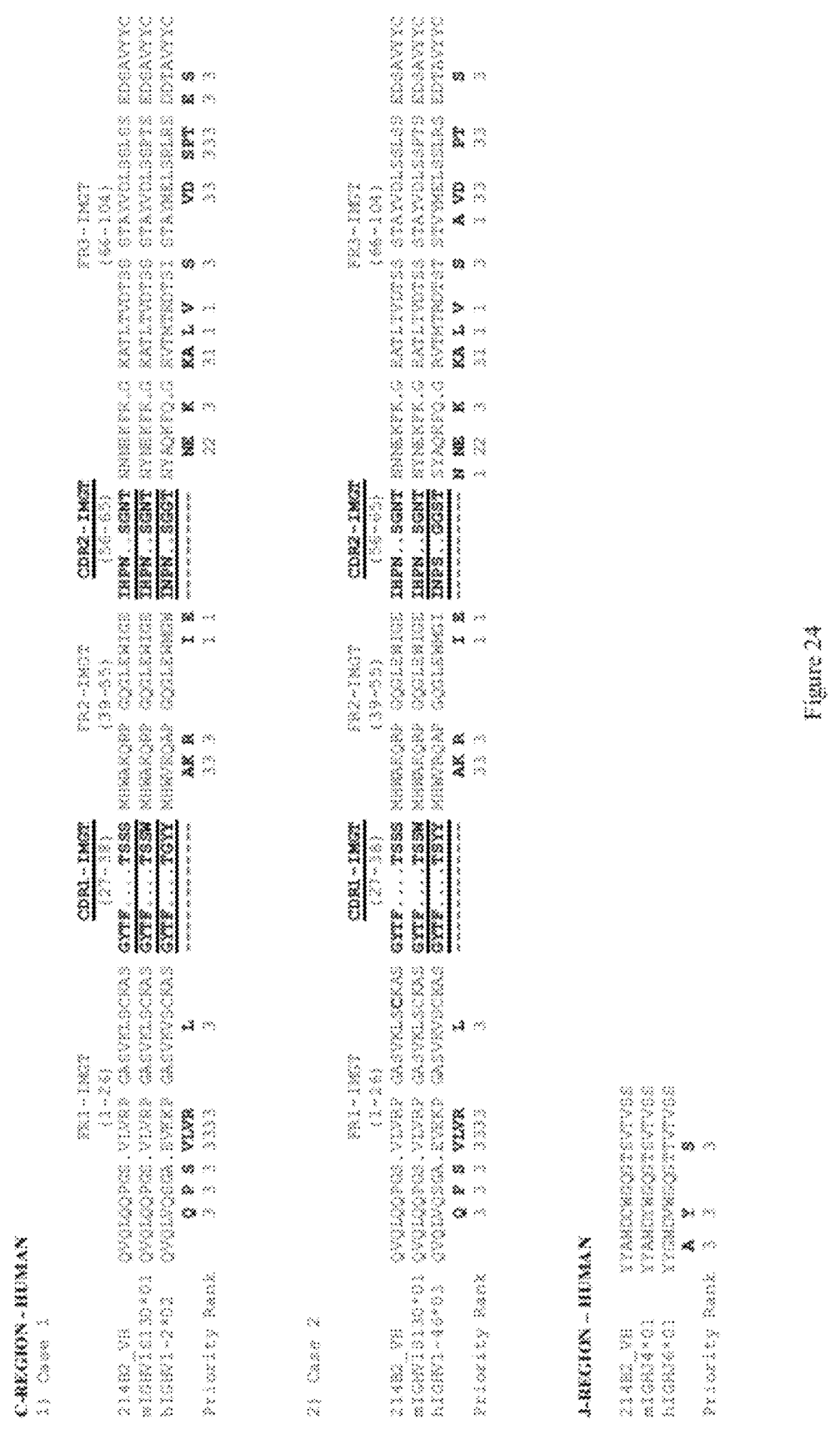

FIG. 24 illustrates the humanization of 214B2 heavy chain with the different Priority Ranking: #1 is high priority (putative high impact on target recognition, CDR presentation and overall 3D structure); #2 is medium priority; and #3 is low priority (putative low impact on target recognition, CDR presentation and overall 3D structure).

The following SEQ ID NOs. apply for the represented V-regions:
1) Case 1: 214B2 VH (amino acids 1-98 from SEQ ID No. 50), mIGHV1S130*01 (SEQ ID No. 111), and hIGHV1-2*02 (SEQ ID No. 117).
2) Case 2: 214B2 VH (amino acids 1-98 from SEQ ID No. 50), mIGHV1S130*01 (SEQ ID No. 111), and hIGHV1-46*03 (SEQ ID No. 118).

The following SEQ ID NOs. apply for the represented J-regions: 214B2 VH (SEQ ID No. 112), mIGHJ4*01, and hIGHJ6*01 (SEQ ID No. 119).

Figure 25:
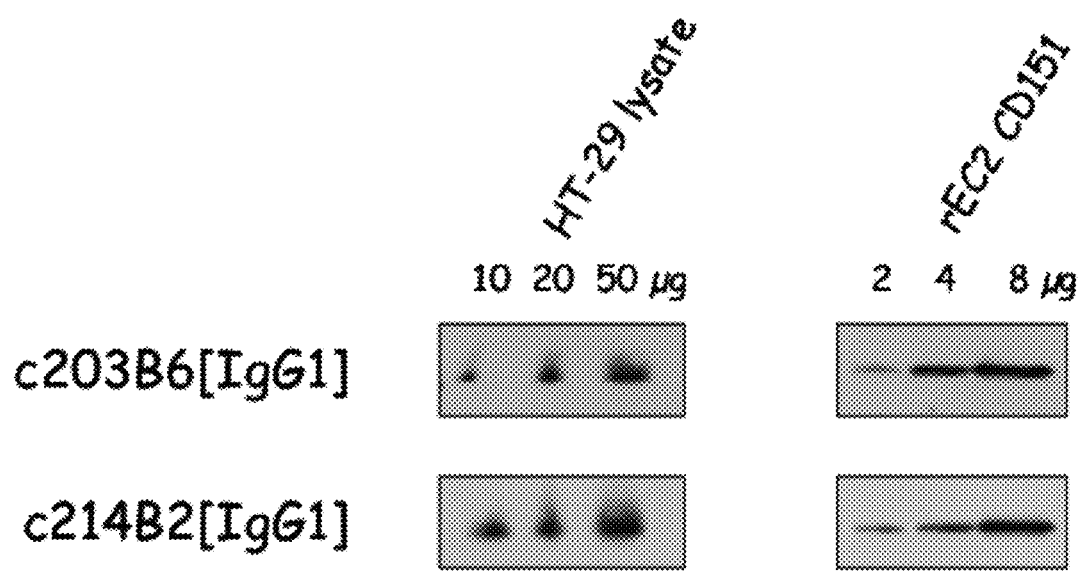

FIG. 25 illustrates the specificity study of chimeric antibodies c203B6[IgG1] and c214B2[IgG1] by western blot.

Figure 26A:
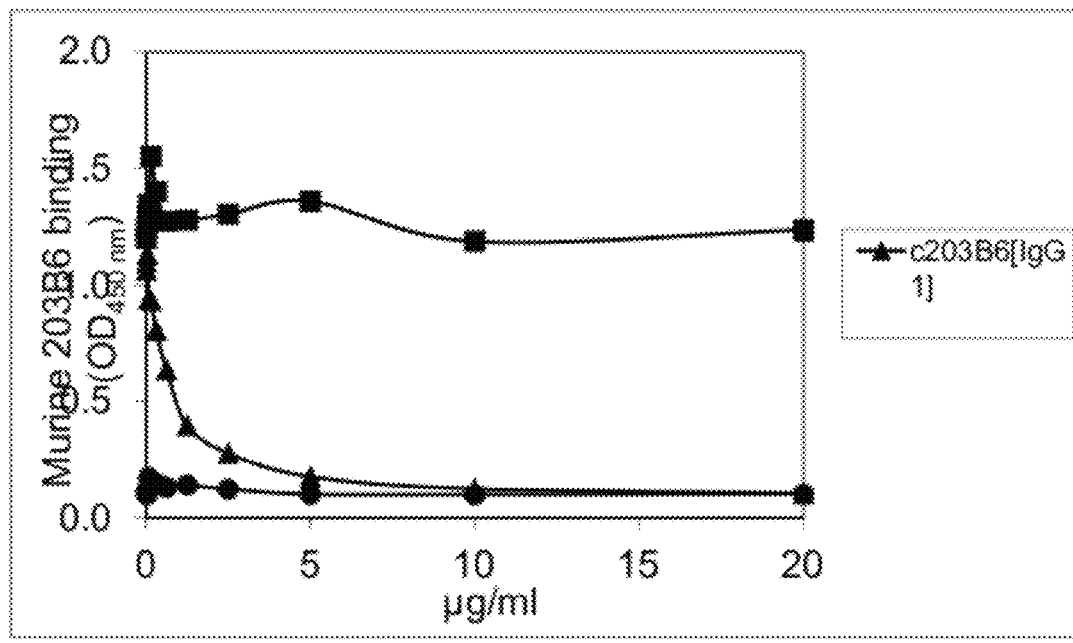
Figure 26B:
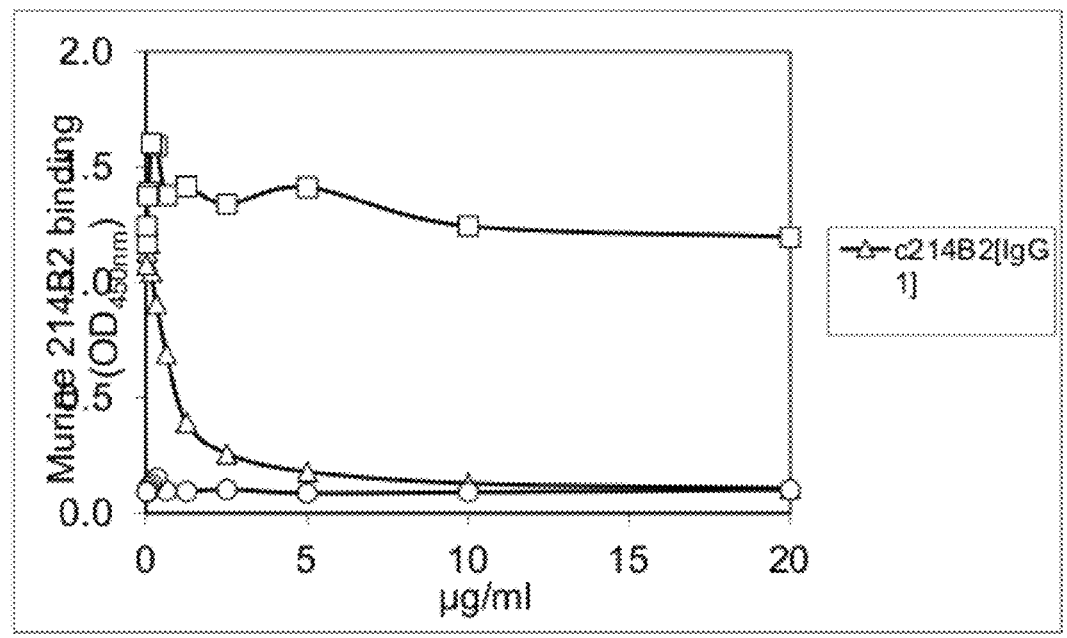

FIGS. 26A-26B illustrate the inhibition of binding of murine Mabs 203B6 and 214B2 to recombinant EC2 by their respective chimeric forms: c203B6[IgG1] (A); c214B2 [IgG1] (B).

FIGS. 27A-27B: Binding of chimeric antibodies to PC3 cells with A: c214B2[IgG1] and B: c203B6[IgG1].

Figure 28:
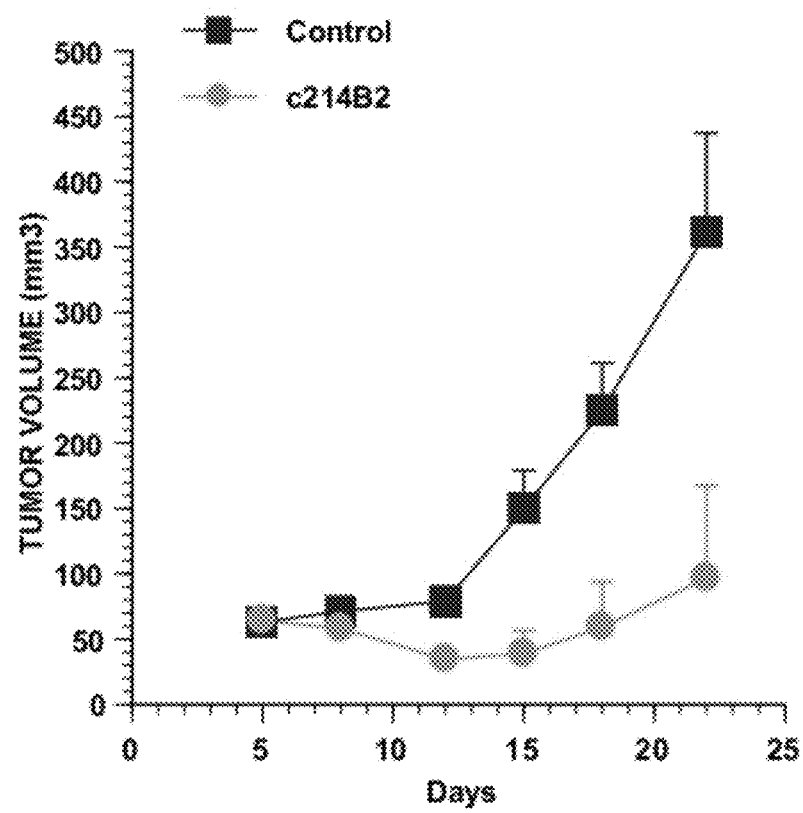

FIG. 28 illustrates the in vivo activity of the c214B2[IgG1] Mab on tumor growth of PC3, an androgen-independent prostate cell line.

EXAMPLES

Example 1

Study of Expression of the CD151 Molecule

The expression of the CD151 protein was researched by immunohistochemistry (IHC) in samples of human tissues obtained from patients suffering from prostate cancers or lung cancer. For these patients, slides of normal tissues adjacent to the tumour were available and were therefore included in order to calibrate the level of expression in the tumour tissues versus normal tissues.

For these experiments, commercially available slides of the "Tissue array" type are used. After deparaffinisation, antigen unmasking is performed at 30° C. with the aid of an enzymatic solution containing pepsin (Labvision ref. AP-9007-005). This step is followed by a step of removal of endogenous peroxidases by incubation of the sections in a solution of hydrogen peroxide (Sigma) 0.3% in water. Saturation of the non-specific sites is then carried out with a solution of Ultra-V-Block (Labvision, ref. TA-125-UB) and labelling is carried out using a commercially available murine anti-CD151 antibody (Serotech, Ref. MCA 1856) used at a final concentration of 5 μg/ml. A murine IgG1 isotype control antibody (DakoCytomation, Ref. X0931) is used as a negative experimental control. Labelling visualisation is performed using the Envision Dual Link visualisation system (DakoCytomation, Ref. K4061) and the reference of the DAB peroxidase substrate is S3309 from DakoCytomation.

Figure 2:
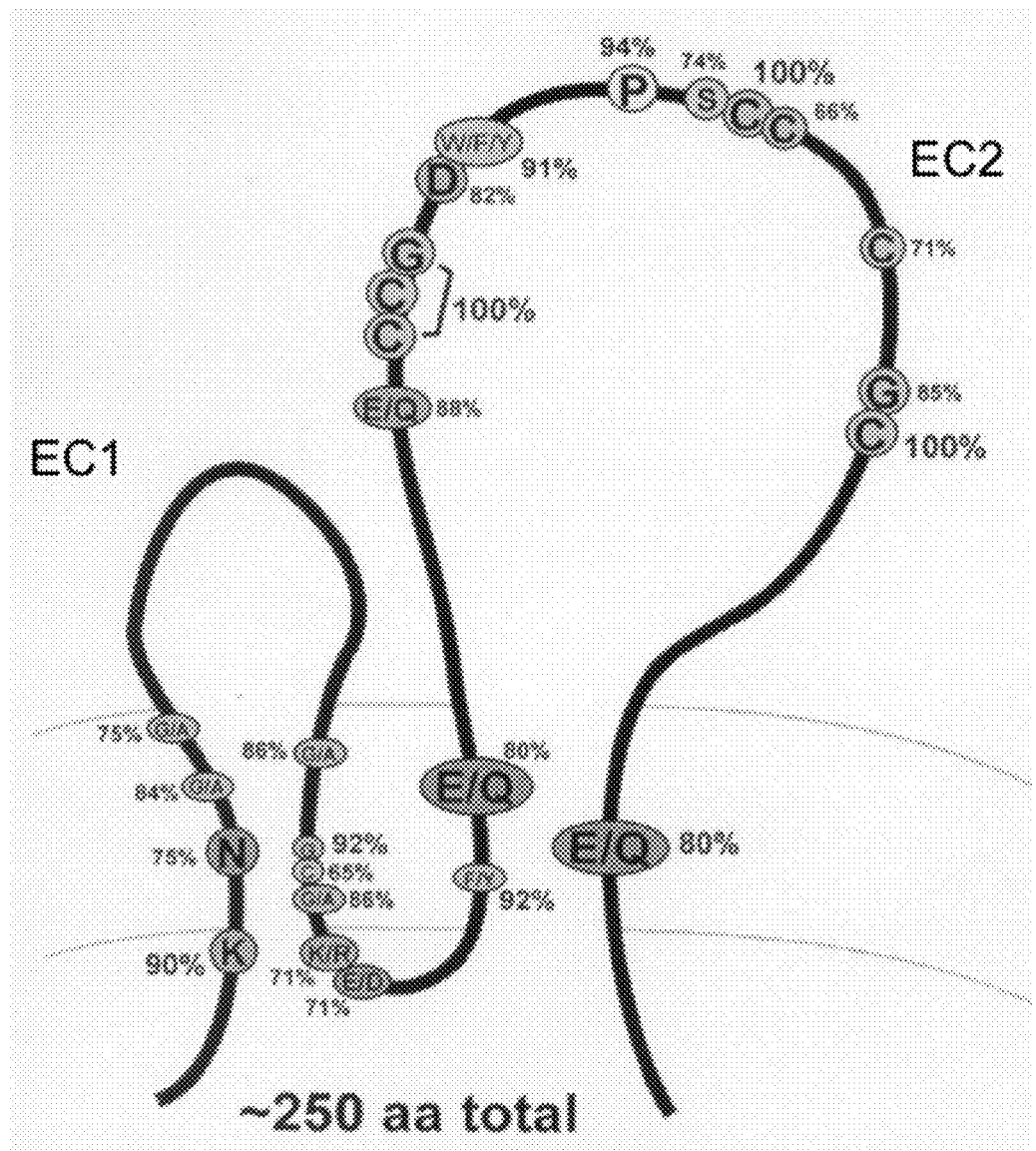
FIG. 2 is a diagram illustrating the structure of the tetraspanins, to which the CD151 protein belongs, and very especially the two extracellular loops EC1 and EC2.
Figures 7A, 7B, 7C, 7D, 7E:
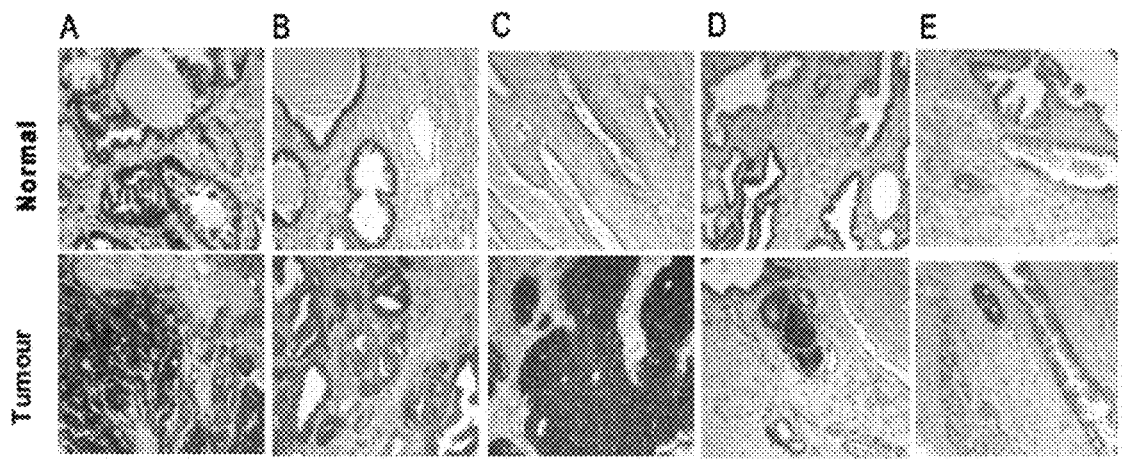
FIGS. 7A-7E illustrate the expression of the CD151 molecule in patients suffering from prostate cancer. Each letter corresponds to study of one patient and for each patient the upper panel corresponds to the normal tissue adjacent to the tumour and the lower panel corresponds to the tumour tissue.

The results presented in FIG. 7 show that a number of patients developing prostate tumours exhibit overexpression of the CD151 molecule. This overexpression may be very significant for 20% of the patients studied (patients A and C) or moderate (patients A and D). It is to be noted that, except at the level of the endothelial cells, the corresponding normal prostatic tissues do not express CD151 or express it only a little and that, where it is expressed, it seems to be limited to glandular type structures. Patient E exhibits an example of a tumour not expressing CD151.

Figures 8A, 8B, 8C:
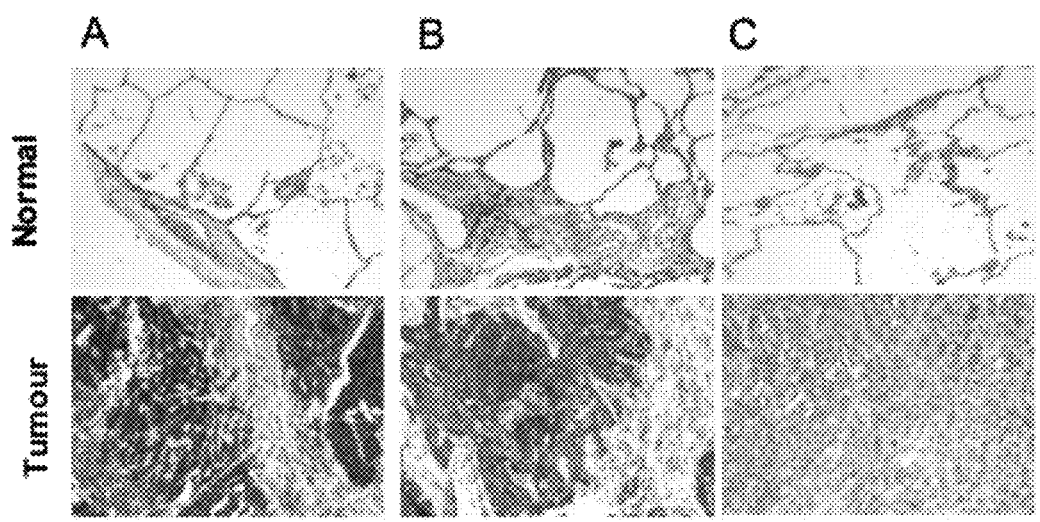
FIGS. 8A-8C illustrate the expression of the CD151 molecule in patients suffering from lung cancer. Each letter corresponds to study of one patient and for each patient the upper panel corresponds to the normal tissue adjacent to the tumour and the lower panel corresponds to the tumour tissue.
Figure 9A:
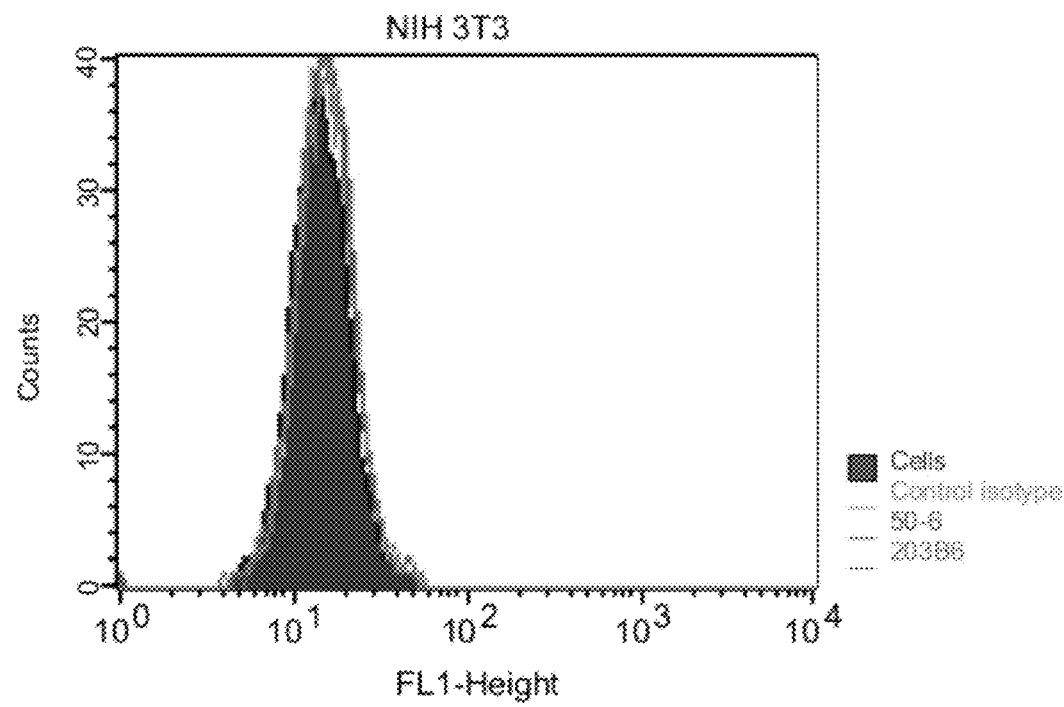
FIGS. 9A-9D show the analysis, by flow cytometry, of the recognition of CD151 by the murine antibody 203B6 on the surface of NIH 3T3-CD151, PC3 and A549 cells.
Figure 9B:
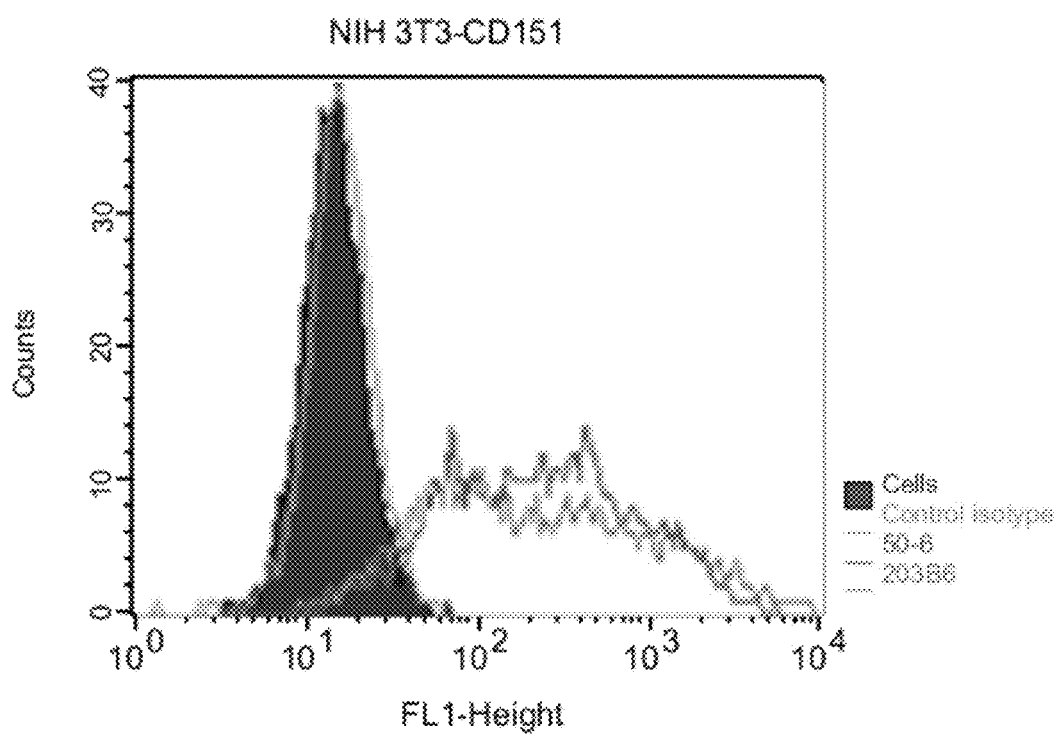
Figure 9C:
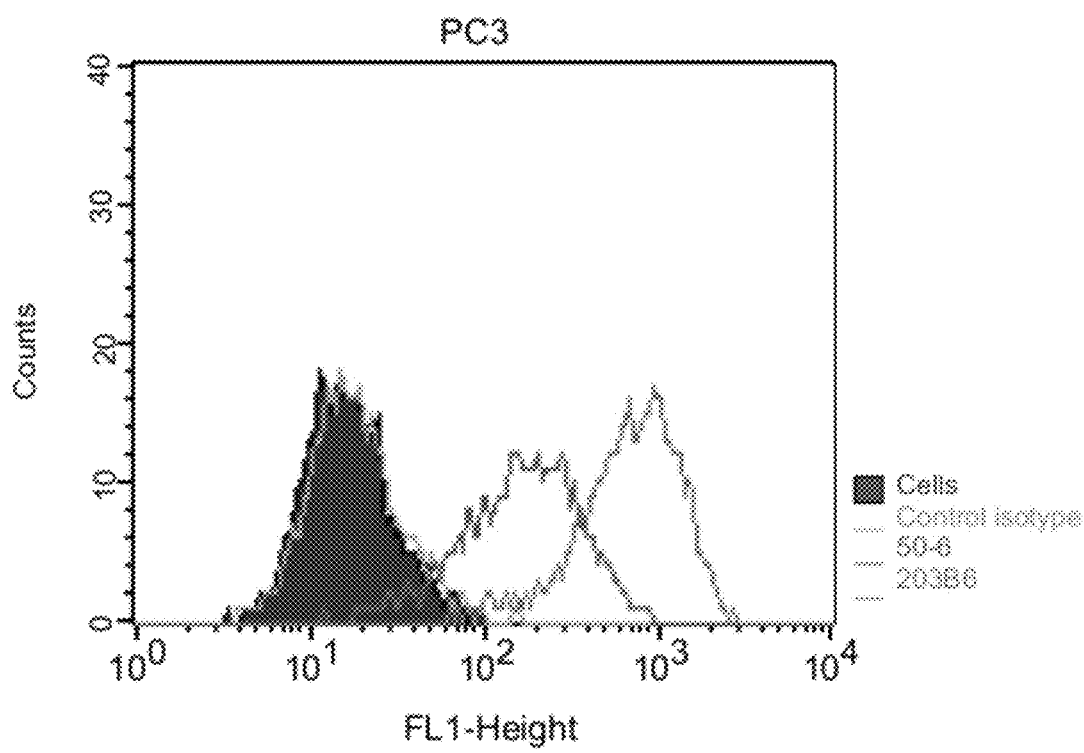
Figure 9D:
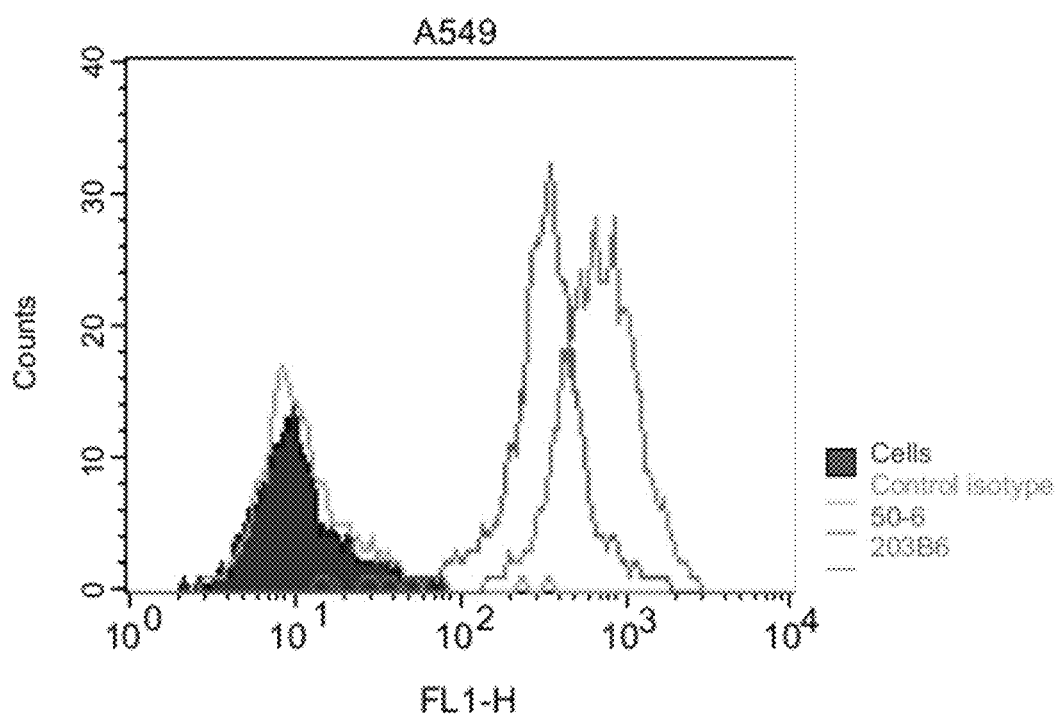
Figure 10A:
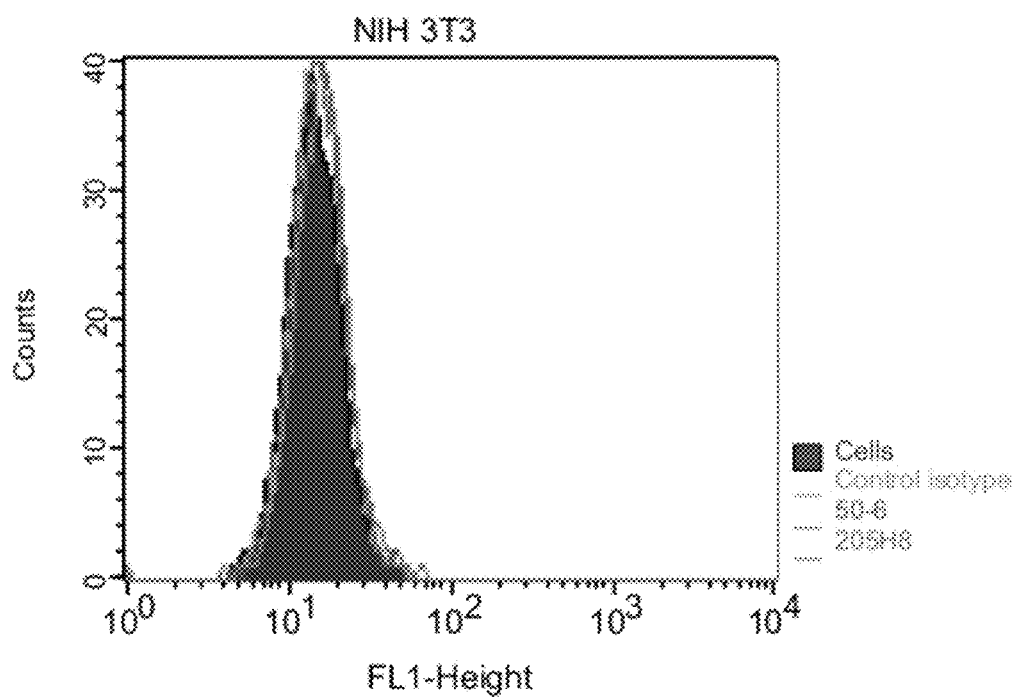
FIGS. 10A-10D show the analysis, by flow cytometry, of the recognition of CD151 by the murine antibody 205H8 on the surface of NIH 3T3-CD151, PC3 and A549 cells.
Figure 10B:
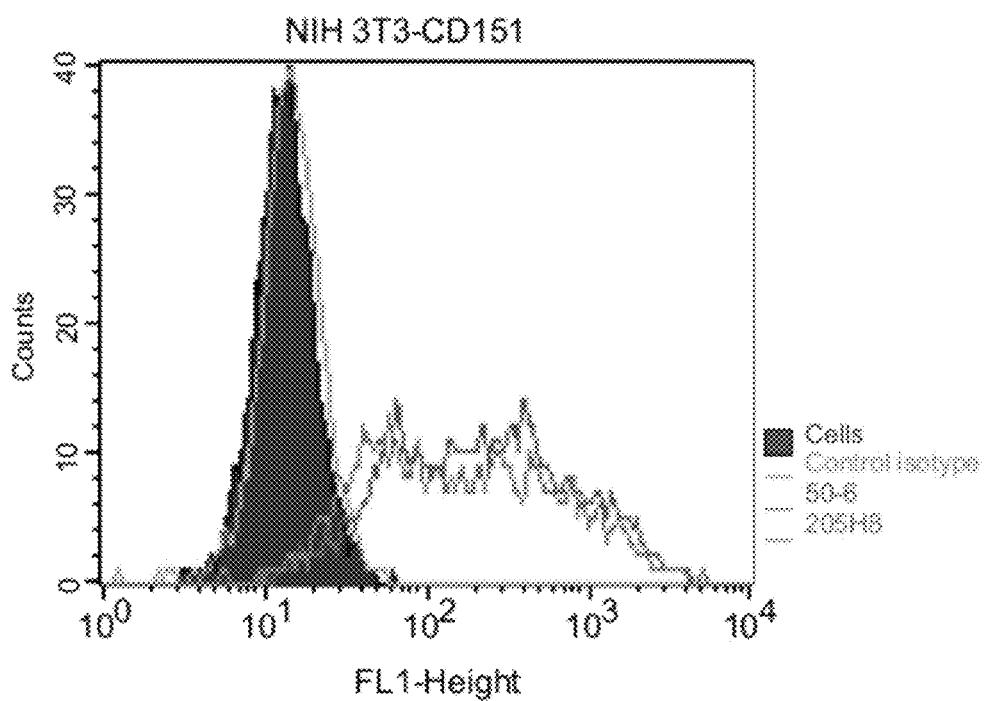
Figure 10C:
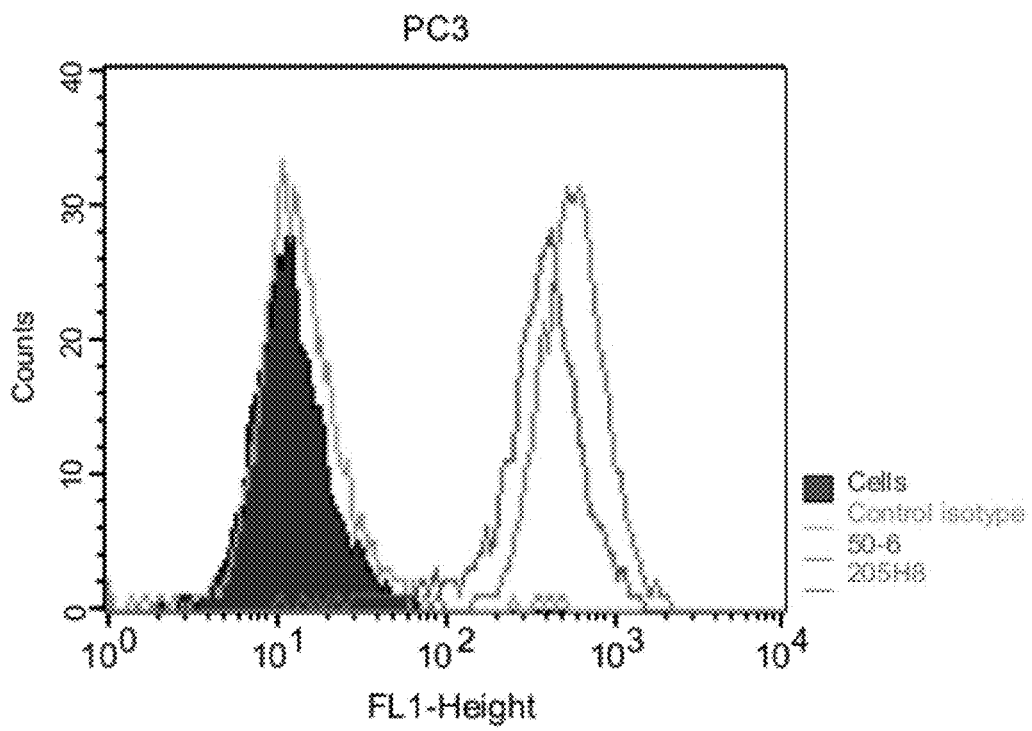
Figure 10D:
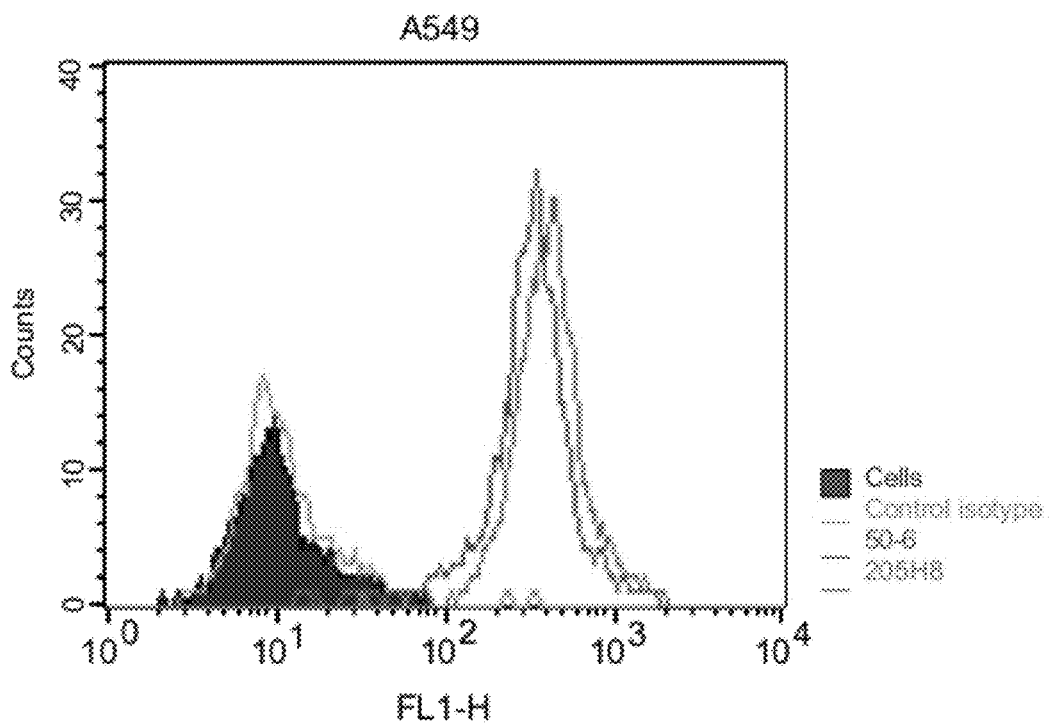
Figure 11A:
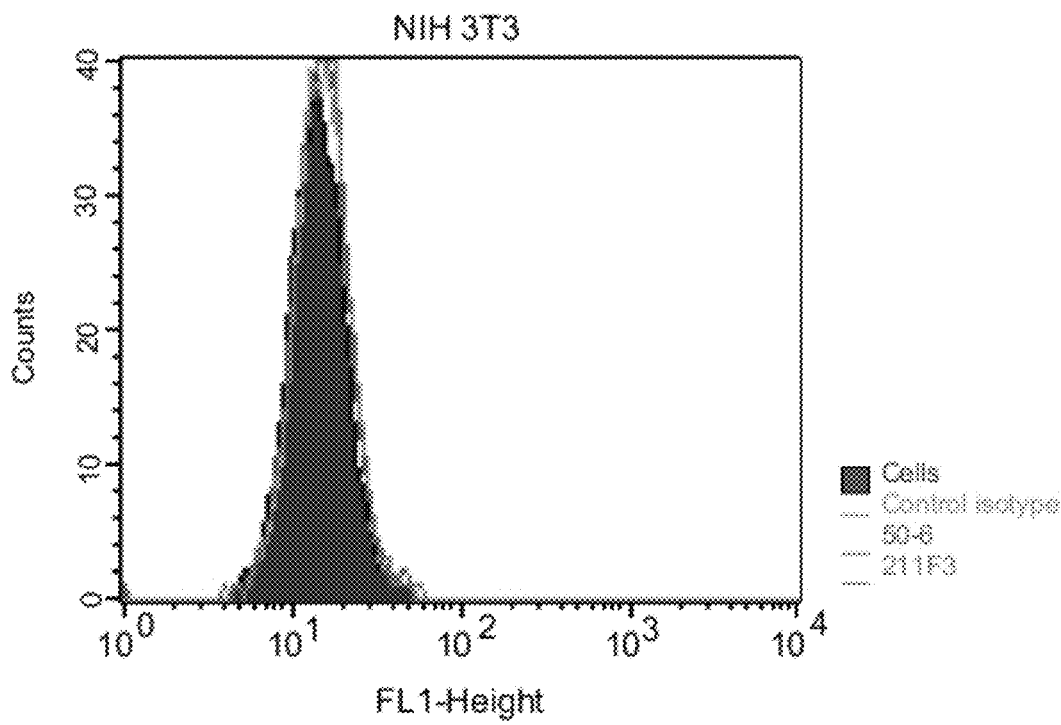
FIGS. 11A-11D show the analysis, by flow cytometry, of the recognition of CD151 by the murine antibody 211F3 on the surface of NIH 3T3-CD151, PC3 and A549 cells.
Figure 11B:
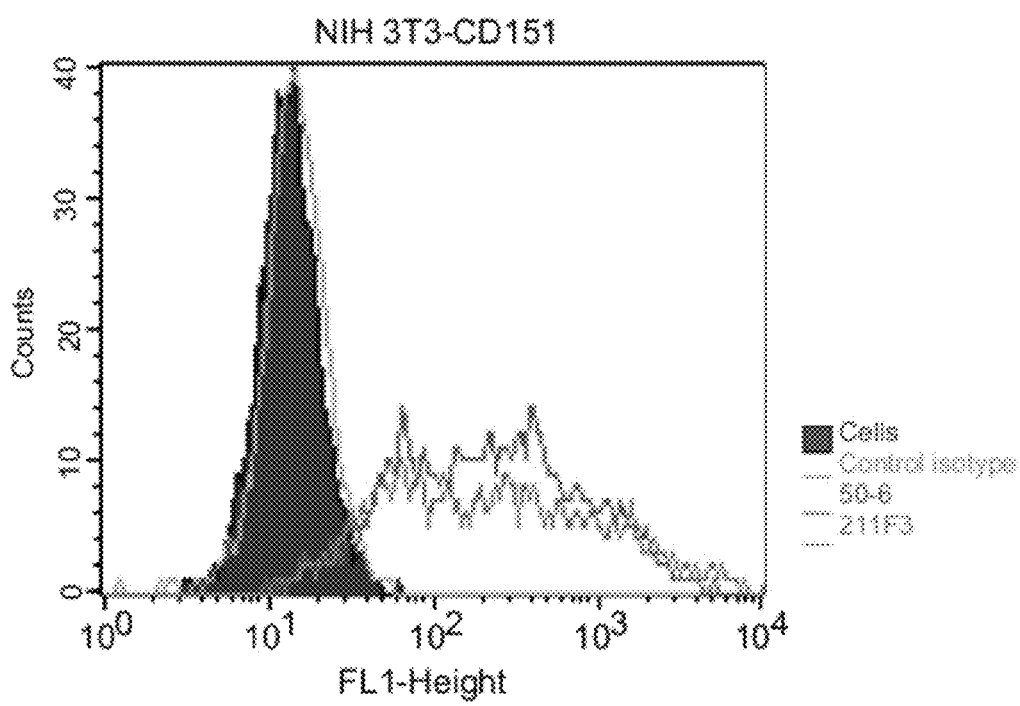
Figure 11C:
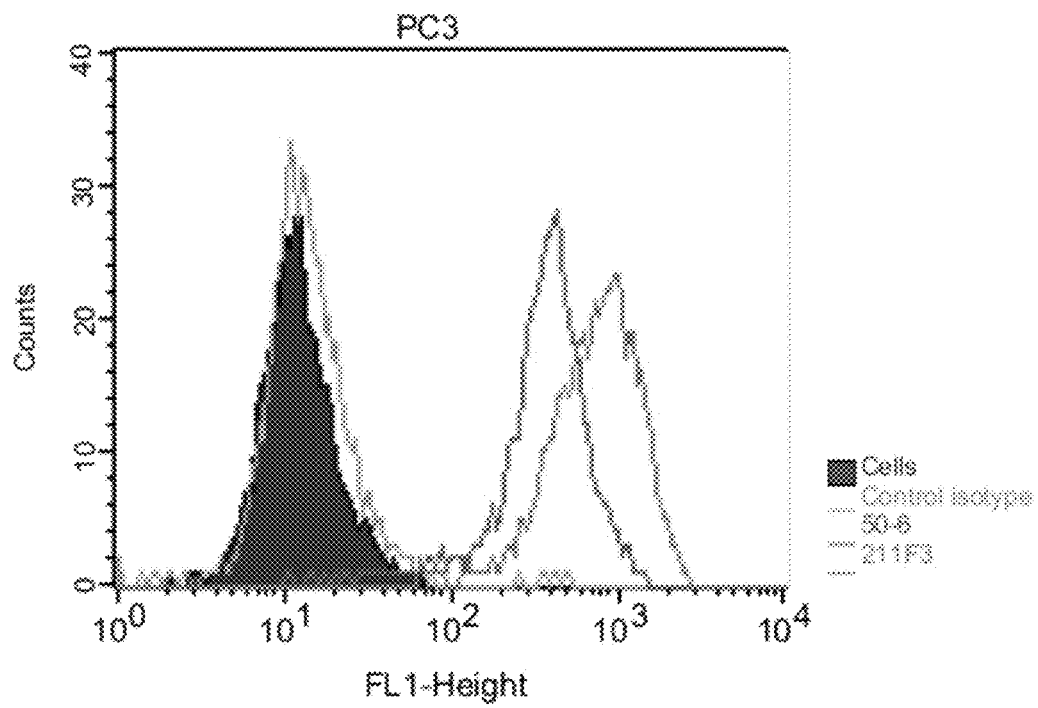
Figure 11D:
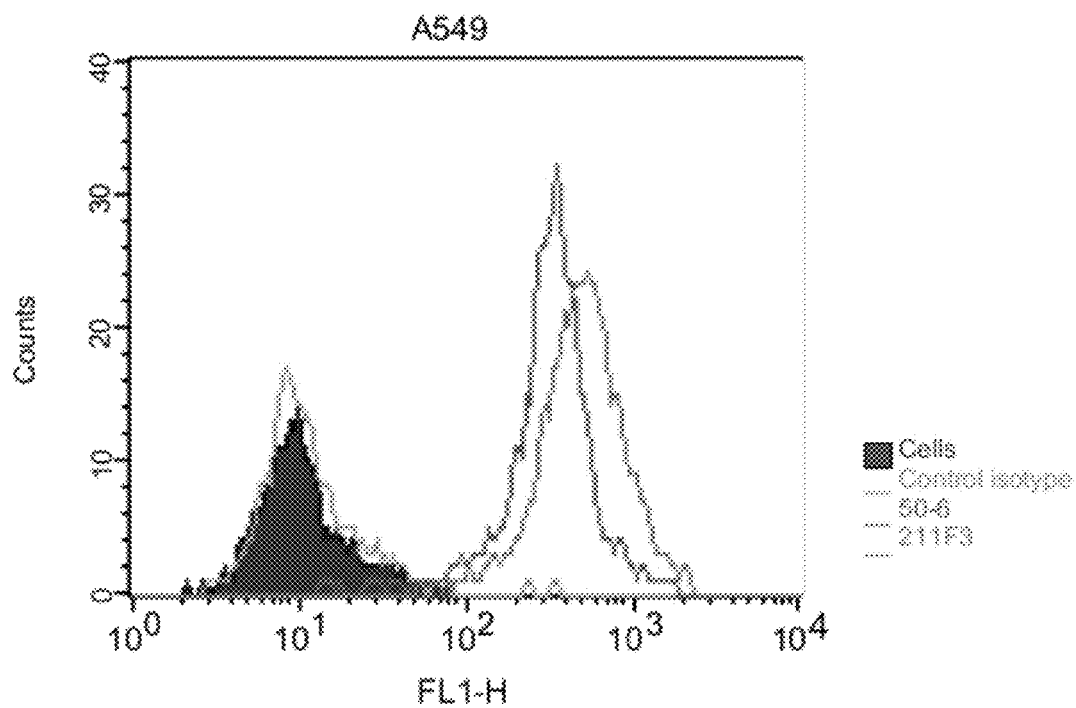
Figure 12A:
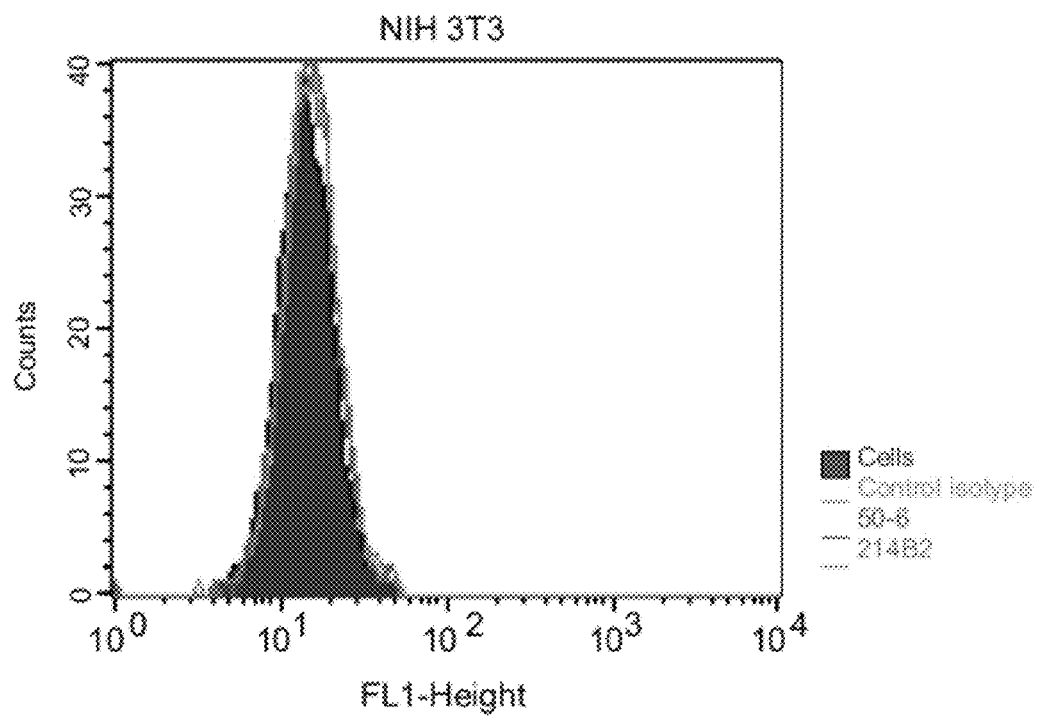
FIGS. 12A-12D show the analysis, by flow cytometry, of the recognition of CD151 by the murine antibody 214B2 on the surface of NIH 3T3-CD151, PC3 and A549 cells.
Figure 12B:
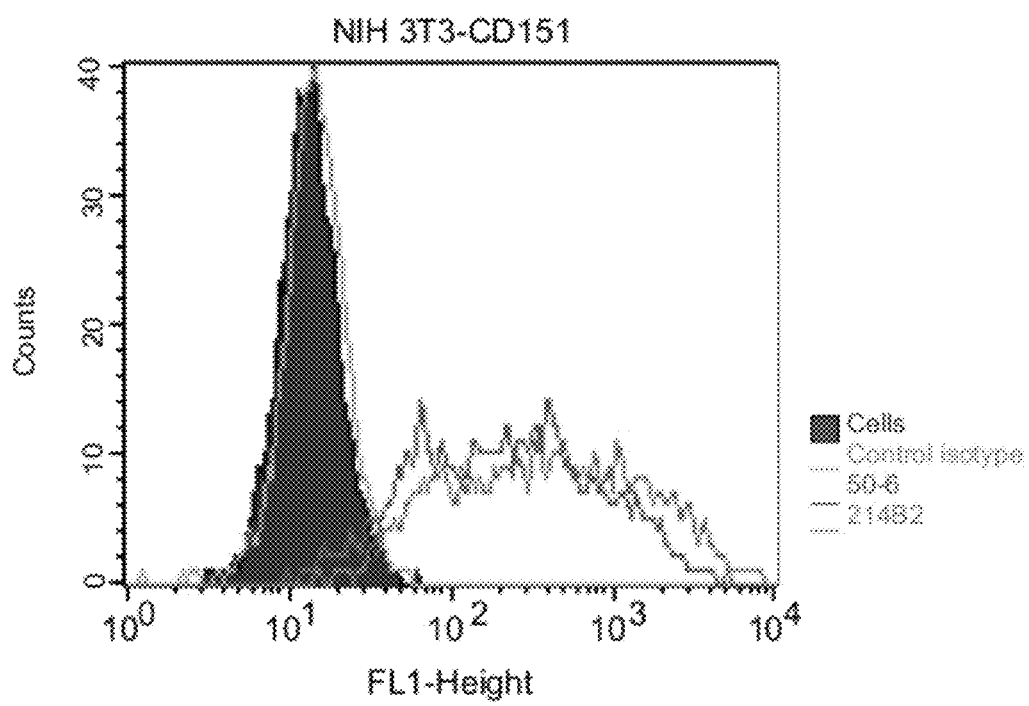
Figure 12C:
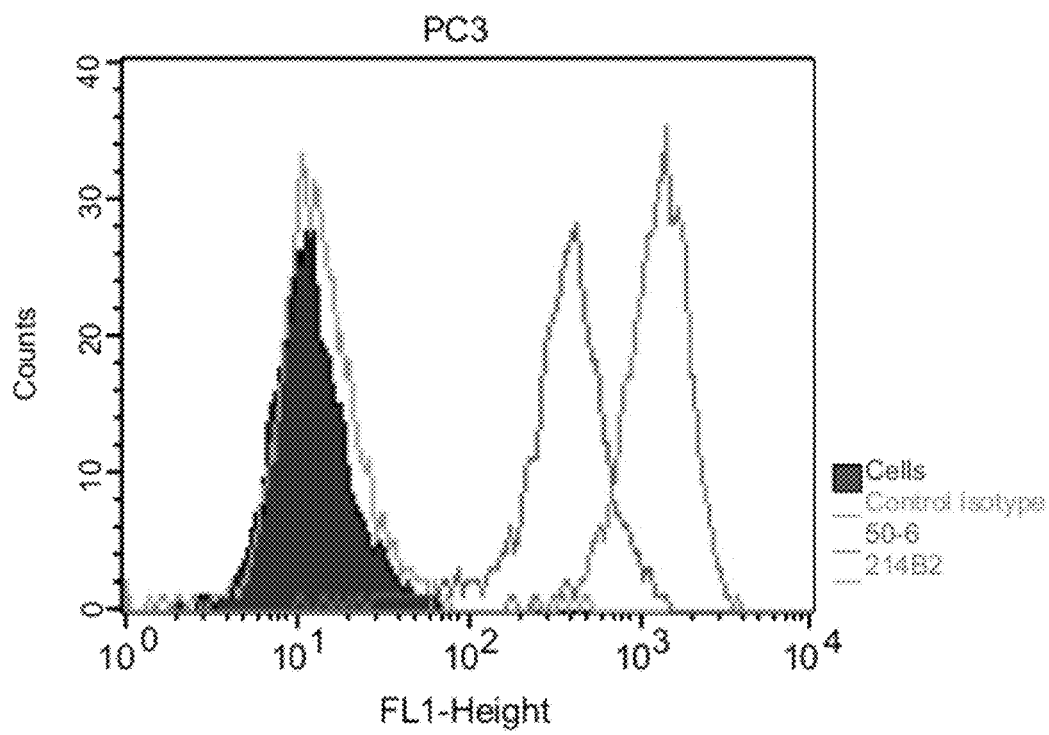
Figure 12D:
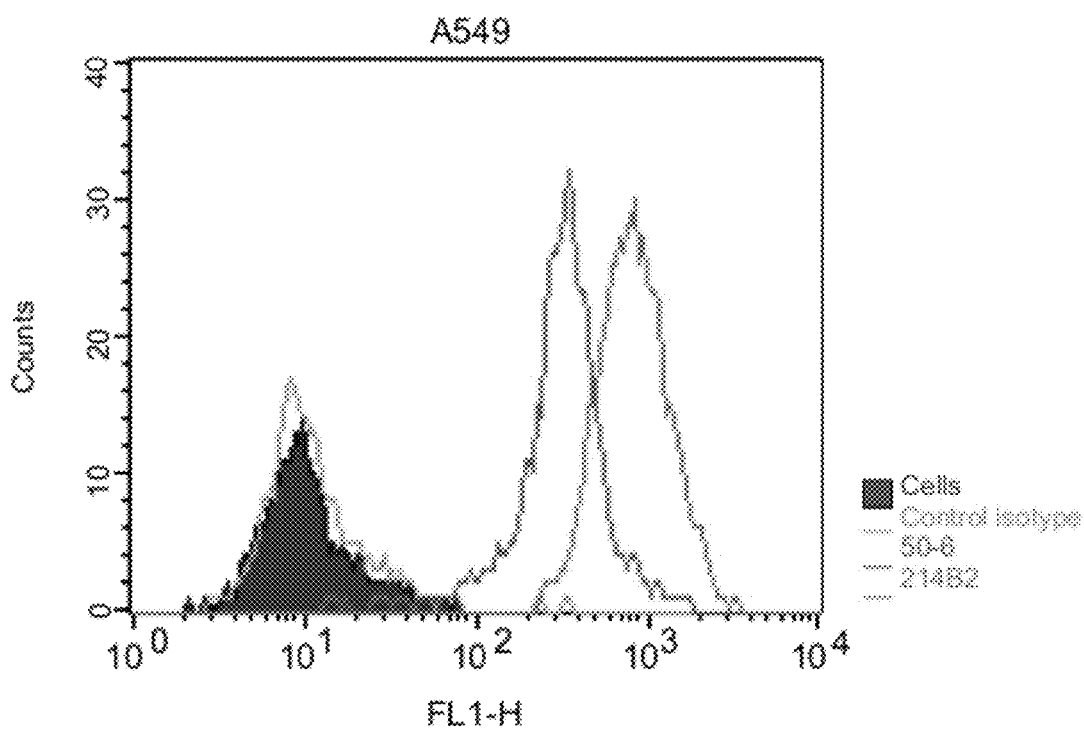

In the case of the lung cancer (FIG. 8), moderate (patient A) to marked (patient B) expression is observed in certain cells of normal pulmonary tissue. However, the tumour tissue exhibits a very high density of heavily labelled cells (patients A and B). Patient C exhibits an example of a tumour not expressing CD151.

Example 2

Generation and Selection of the Antibodies

BALB/c mice were immunised by the subcutaneous route using $20 \times 10^6$ NIH 3T3 cells expressing human CD151 on their surface, those cells having been generated by transfection with the CD151 gene. The first immunisation was carried out in the presence of Freund's complete adjuvant, and the next 2 in the presence of Freund's incomplete adjuvant. Three days before fusion, a final booster injection of $10 \times 10^6$ NIH 3T3-CD151 cells was carried out by the intraperitoneal route. Mouse spleen cells were then fused to SP2/0-Ag14 myeloma cells in a ratio of 1/1 using conventional techniques described by Köhler and Milstein.

The antibodies secreted into the supernatants from the hybridomas resulting from the fusion were then screened for their ability to recognise the recombinant extracellular loop EC2 of CD151 by ELISA, and CD 151 expressed on the surface of the human PC3 prostate cancer tumour line by flow cytometry.

For the ELISA, 96-well plates are sensitized for 1 night at +4° C. with the recombinant extracellular loop EC2 at 5 μg/ml in PBS. After washing with PBS, the wells are saturated with 0.5% gelatin solution in PBS for 1 hour at 37° C. and then washed again with PBS. The hybridoma culture supernatants are evaluated without dilution (incubation for 1 hour at 37° C.). The antibodies fixed to the immobilised EC2 loop are detected by successive incubation with a peroxidase-conjugated goat anti-mouse IgG polyclonal antibody (Jackson/USA, dilution to 1/5000, 1 hour at 37° C.) and then with a peroxidase substrate (TMB, Interchim/France, 10 minutes at ambient temperature). The reaction is stopped by addition of 1M sulfuric acid and the optical density (OD) is measured at 450 nm.

The flow cytometry analyses are carried out on 96-well plates. The undiluted hybridoma supernatants are added to 100000 PC3 cells previously introduced into the wells. After incubation for 20 minutes at +4° C. followed by washing, an Alexa488-labelled goat anti-mouse IgG polyclonal antibody (Molecular Probes, dilution to 1/500) is added. The fluorescence intensity (MFI) is determined with the aid of a cytofluorimeter after further incubation for 20 minutes at +4° C.

At the end of that screening, the following 4 hybridomas were selected (selection criteria: OD>0.5 for the ELISA and MFI>50 for the flow cytometry): 203B6, 205H8, 211F3 and 214B2. The results obtained for those 4 hybridomas are presented in Table 4 below:

TABLE 4

| Hybridoma | ELISA OD 450 nm | Cytometry (PC3) MFI |
|---|---|---|
| 203B6 | 1.130 | 975 |
| 205H8 | 0.649 | 595 |
| 211F3 | 0.959 | 936 |
| 214B2 | 0.684 | 1004 |

After cloning, a clone of each selected hybridoma was amplified. The isotypes of the antibodies produced were determined for each culture supernatant using a murine antibody isotyping kit (SBA clonotyping system, Southern Biotech), and then final characterisation was carried out by ELISA (extracellular loop EC2) and by flow cytometry on the murine line NIH 3T3 and the stable transfectant NIH 3T3-CD151, and then on human tumour lines of lung cancer A549, prostate cancer DU145 and pancreatic cancer BxPC3 under the conditions previously described. The antibody concentration of the supernatants was adjusted to 5 μg/ml for the ELISA and to 10 μg/ml for the flow cytometry analyses. The results obtained are presented in Table 5 below:

TABLE 5

| Anti-CD151 antibody | Isotype | ELISA OD at 450 nm | Flow cytometry MFI | | | | |
|---|---|---|---|---|---|---|---|
| | | | NIH3T3 | NIH3T3-CD151 | A549 | DU145 | BxPC3 |
| 203B6 cl1A | IgG1 K | 2.218 | 16 | 540 | 675 | 860 | 768 |
| 205H8 cl1A | IgG3 K | 1.842 | 16 | 332 | 388 | 584 | 350 |
| 211F3 cl1A | IgG1 K | 2.301 | 16 | 556 | 481 | 524 | 536 |
| 214B2 cl1A | IgG1 K | 2.477 | 16 | 748 | 820 | 1332 | 849 |

FIGS. 9, 10, 11 and 12 show the recognition profiles for the NIH 3T3-CD151, PC3 and A549 cells, by flow cytometry, which are obtained for the antibodies 203B6, 205H8, 211F3 and 214B2. These profiles are comparable to those obtained with the anti-CD151 antibody 50-6 (ATCC CRL-2696) and demonstrate the specificity of these antibodies for CD151.

The hybridomas were then deposited at the CNCM, Collection Nationale de Cultures de Microorganismes, Institut Pasteur, 25 Rue du Docteur Roux, 75724 PARIS Cedex 15.

Example 3

Specificity of the Antibodies

The specificity of the 203B6, 205H8, 211F3 and 214B2 antibodies was evaluated by Western blot.

The EC2 loop of CD151 was cloned into the vector pET22b for expression in soluble form in the periplasm of *Escherichia coli*. The protein that is produced includes amino acids 130 to 221 of the human CD151 peptide sequence to which there is added a Poly-His tail at the C-terminal position in order to facilitate purification. The recombinant EC2 protein was purified by immobilised metal affinity chromatography (IMAC) on a Chelating Sepharose HP support (GE Healthcare).

Increasing amounts of the recombinant CD151 EC2 protein (1, 2, 4 and 8 μg) and of HT-29 cell lysate (10, 20 and 50 mg of total proteins) were placed on a 4-12% acrylamide gel (BioRad). After electrophoresis (non-reductive conditions), the proteins were transferred onto nitrocellulose membranes. The transfer membranes were then incubated with the purified 203B6, 205H8, 211F3 and 214B2 antibodies (0.5 μg/ml) and then with a rabbit anti-mouse Ig polyclonal antibody coupled to peroxidase (GE Healthcare) before visualisation by chemoluminescence.

Figure 13:
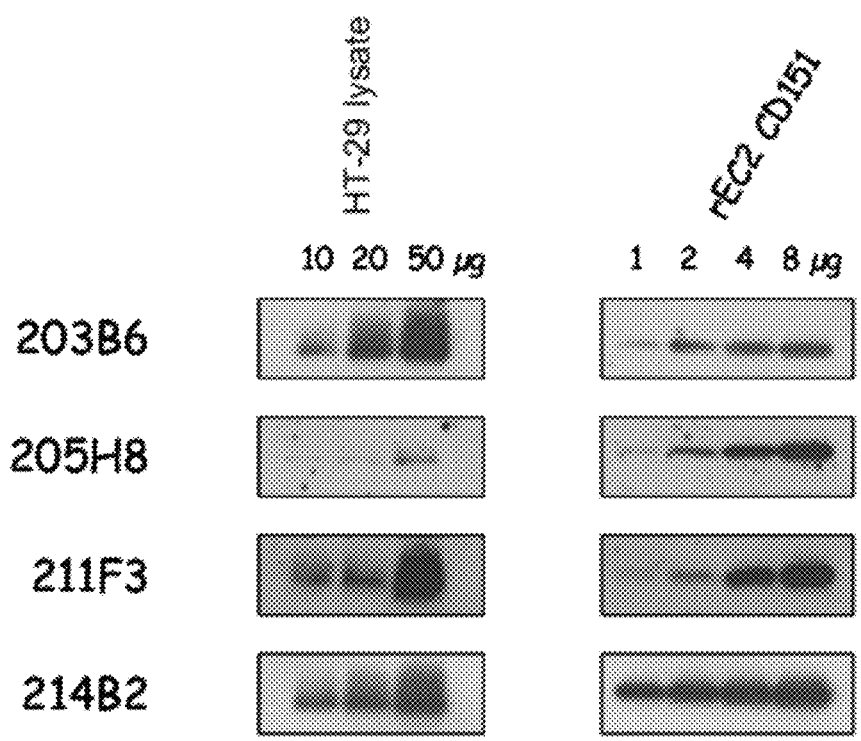
FIG. 13 shows the results of evaluation of the specificity of antibodies 203B6, 205H8, 211F3 and 214B2 by Western blot.
Figure 14A:
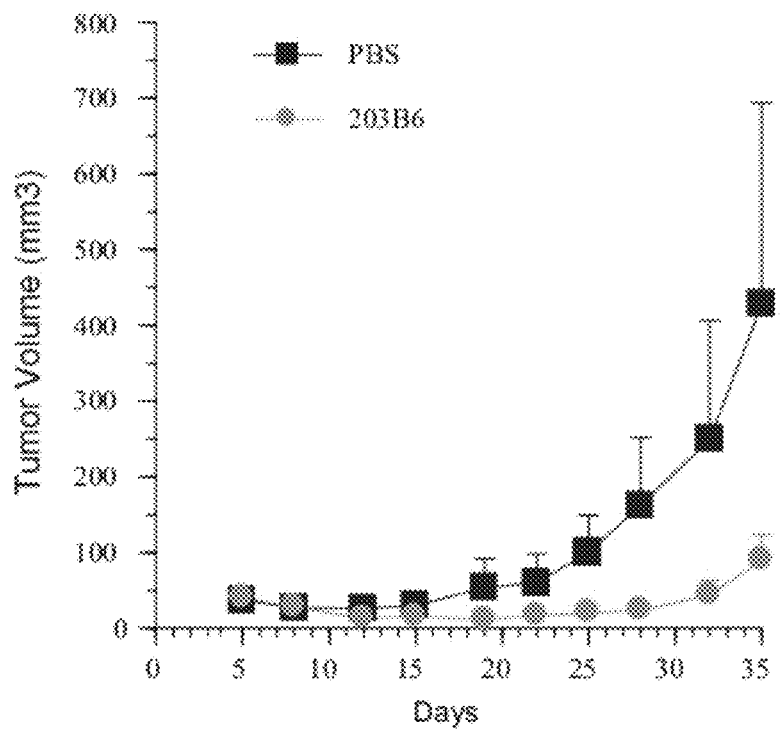
Figure 14B:
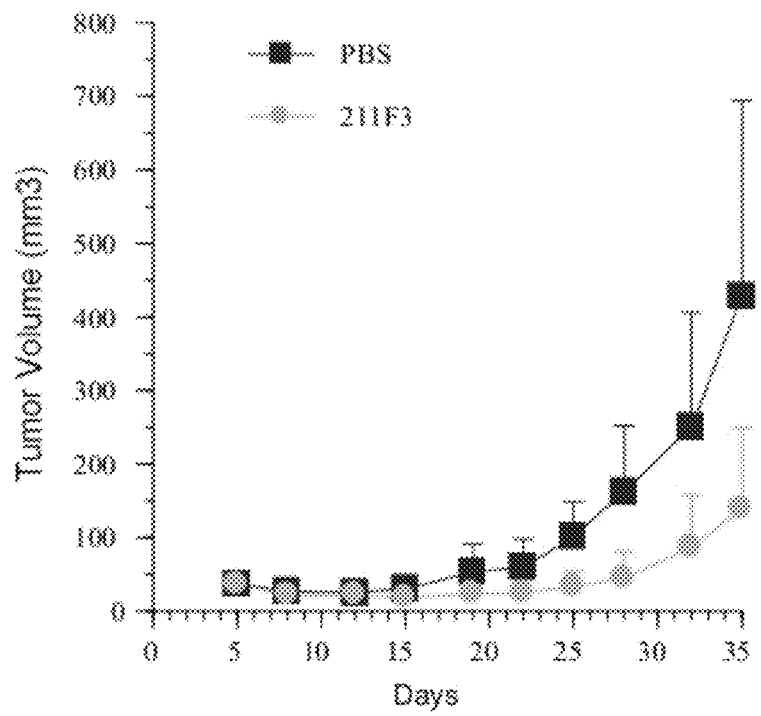
Figure 14C:
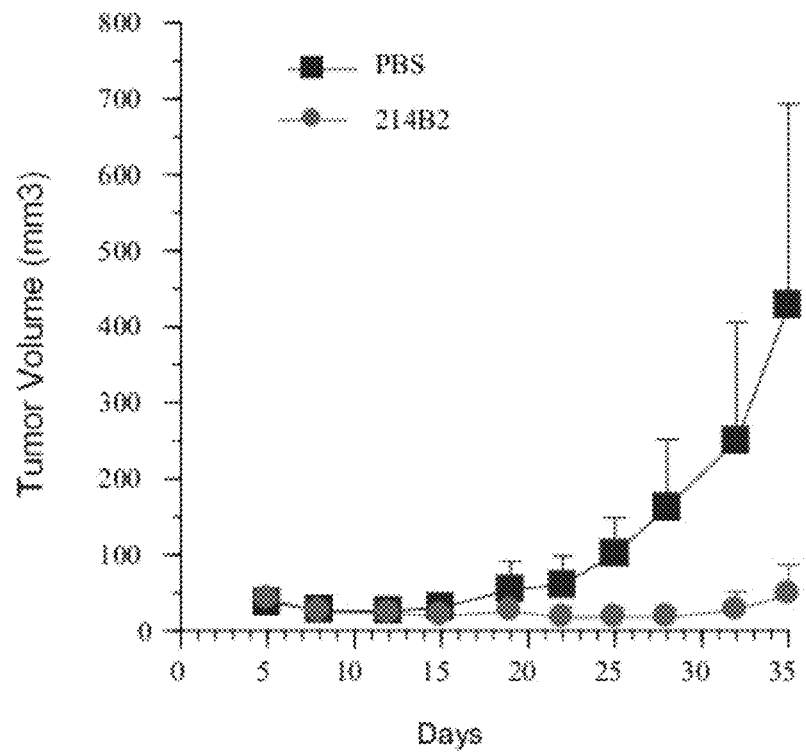
Figure 14D:
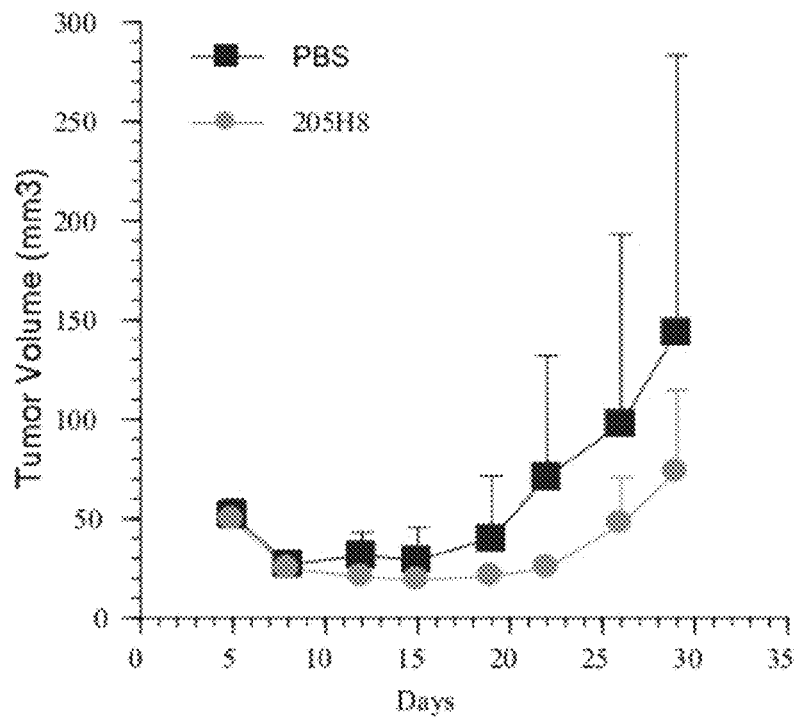

The 203B6, 205H8, 211F3 and 214B2 antibodies recognise the complete CD151 protein and the recombinant EC2 loop by Western blot (FIG. 13). The antibody 205H8 has less reactivity for the complete CD151 protein under the conditions of analysis. Compared to the signal observed for the antibodies 203B6, 211F3 and 214B2, the signal obtained for the antibody 205H8 is found to be weaker. This difference is not observed for recognition of the recombinant EC2 protein.

Example 4

Anti-Tumour Activity of Anti-CD151 Antibodies in the PC3 Xenograft Model

Material and Methods

Having observed CD151 overexpression in tumour tissues of prostate cancer by means of immunohistochemistry on a human tissue array series, the evaluation of anti-CD151 antibodies on a PC3 prostate cancer cell xenograft was planned. The PC3 line is an androgen-independent prostate line obtained from ATCC and cultured in F12K medium (Invitrogen Corporation, Scotland, United Kingdom), 10% FCS (Invitrogen Corporation). The cells are divided two days before the graft so that they are in the exponential growth phase. Five million PC3 cells are subcutaneously grafted onto six-week-old male Swiss Nude mice. Five days after implantation, the tumour volumes are measured, the mice are randomised so as to form groups that are not statistically different, and the treatment is started by i.p. injection of a challenge dose of 2 mg of antibody per mouse. The animals are then treated twice a week with a dose of 1 mg of antibody per mouse and the tumours are measured twice a week. The animals of the control group are given an injection of PBS. The tumour volumes are calculated according to the formula $\pi/6 \times length \times width \times height$. Statistical analysis is carried out on each measurement using a Mann-Whitney test.

Results

The results presented in FIG. 14 show that the antibodies 203B6, 214B2 and 211F3 exhibit significant inhibition of the tumour growth in vivo of the PC3 cells. The antibody 205H8, whilst being an inhibitor, shows more modest anti-tumour activity in this model.

Example 5

Study of the Fixing of Anti-CD151 Antibodies to PC3 Cells

The anti-CD151 antibodies 203B6 and 214B2 were first labelled with iodine 125 by the method using chloramine T. After labelling, the antibodies were purified by molecular-sieve chromatography on a PD-10 column (GE Healthcare) in order to remove the free iodine 125. The radiochemical purity of the radiolabelled antibodies was determined, after purification, by silica thin-layer chromatography, analytical molecular-sieve chromatography on a Superdex 200 column (GE Healthcare) and by autoradiography after SDS-PAGE electrophoresis. FIG. 15 shows that the heavy chains (~50 kDa) and light chains (~25 kDa) of the 2 antibodies are labelled in equivalent manner (15A) and confirms the absence of free iodine 125 after purification (15B). The specific activity of the radiolabelled antibodies was determined using a gamma counter (Wallace Wizard 1480, Perkin Elmer).

The physico-chemical characteristics of the 203B6 and 214B2 antibodies radiolabelled with iodine 125-[$^{125}$I]-203B6 and [$^{125}$I]-214B2—are collated in Table 6 hereinbelow:

TABLE 6

| Antibody | [$^{125}$I]-203B6 | [$^{125}$I]-214B2 |
|---|---|---|
| Labelling efficiency (%) | 85.5 | 78.1 |
| Specific activity (mCi/mg) | 10.6 | 12.7 |
| Radiochemical purity (%) | 99.7 | 99.5 |
| Atoms of iodine/antibody | 0.73 | 0.87 |

The affinity of the 2 radiolabelled antibodies for their CD151 target on the cell surface was then measured for PC3 prostate cancer cells. The dissociation constant $K_D$ of the antibodies was determined by the method of Scatchard. The PC3 cells ($1 \times 10^6$ cells/50 µl of PBS buffer containing 0.5% BSA) were incubated in the presence of increasing concentrations of the radiolabelled antibodies between 6 ng/ml and 27 µg/ml, inclusive, for 1 hour at 4° C. (final volume: 150 µA). After incubation, the total to radioactivity associated with the cells (fixed radiolabelled antibody) was measured using a gamma counter. The non-specific fixing was determined, for each concentration tested, in the presence of an excess of non-radiolabelled antibody (×100). The specific fixing is calculated by subtracting the non-specific radioactivity from the total radioactivity. The saturation curves are shown in FIGS. 16A and 17A for the antibodies [$^{125}$I]-203B6 and [$^{125}$I]-214B2, respectively. The Scatchard curves obtained (FIGS. 16B and 17B) after processing of the data using Prism software allow the dissociation constant $K_D$ of the 2 antibodies (slope=$-1/K_D$) to be determined:

| 203B6 | $K_D = 12.85 \pm 0.99$ nM |
|---|---|
| 214B2 | $K_D = 6.38 \pm 0.45$ nM |

Example 6

Effect of the Anti-CD151 Antibodies on Platelet Functions

Aggregation is a basic function of platelets in the blood coagulation process, for example in response to a vascular lesion. This phenomenon is generally preceded by activation of the platelets, which involves exposure of certain proteins on their surface and secretion of the contents of their storage granules (alpha granules and dense granules). In view of the fact that CD151 is expressed on the platelets (Goschnick and Jackson, 2007, Mini-Rev. Med. Chem. 7: 1236-1247), the effect of anti-CD151 antibodies on platelet functions was evaluated in vitro using platelet aggregation and activation tests.

For this study, blood samples were taken from fasting donors using trisodium citrate as anticoagulation agent. Centrifuging at 100 g for 10 minutes at 20° C. makes it possible to obtain platelet-rich plasma (PRP), whereas platelet-poor plasma (PPP) is obtained by centrifuging at 1500 g for 10 minutes at 20° C. Platelet aggregation was measured in the PRP of 10 donors, after adjustment to 300000 platelets/mm$^3$, according to Born's principle (modification of the light transmitted), with stirring at 500 rpm at 37° C. The measurement duration was 5 minutes for thrombin and ADP (positive controls) and 15 minutes for the antibodies tested. Platelet activation was measured in the PPP of 10 donors, by measuring the secretion of serotonin (5-hydroxytryptamine or 5-HT) using HPLC with fluorimetric detection. The effect of the antibodies on platelet functions was determined for a concentration of 10 µg/ml. Several control antibodies were used: PM6/248 (anti-CD41, integrin $\alpha_{IIb}$) and 14A2.H1 (anti-CD151) as positive control antibodies, and 9G4 as isotype control (IgG1).

The platelet aggregation caused by the various compounds tested is assessed for each donor as a percentage of the aggregation caused by thrombin, which is taken as reference (100%). FIG. 18A shows the mean aggregation values obtained for each compound tested. ADP and the antibody PM6/248, agents which have a causative effect but which are less potent than thrombin, bring about comparable aggregation, 30.1±10.5% and 47.6±12.7%, respectively. The variations in the values obtained are routinely observed in haemostasis and result from the inter-individual variability. As expected, the 9G4 antibody does not cause platelet aggregation: this antibody allows a detection threshold (5 nM) to be defined. The aggregation caused by the anti-CD151 antibodies 203B6 and 214B2, 7.3±3.2% and 4.9±1.6% respectively, is relatively low and close to the detection threshold. The aggregation caused by these 2 antibodies is less than that of the control antibody 14A2.H1.

FIG. 18B shows the mean values for serotonin released by the platelets (in nM) in the presence of the various compounds tested. The results obtained for this test of platelet activation are comparable to those described above. The 9G4 antibody does not cause platelet activation whereas thrombin brings about a very marked release of serotonin (~430 nM). The amounts of serotonin released are less in the presence of ADP, PM6/248 and 14A2.H1 (mean values of 72.6 nM, 34.6 nM and 21.6 nM. respectively) but these compounds can be classed as platelet activators. The serotonin release caused by the anti-CD151 antibodies 203B6 and 214B2 is very low: in fact, the mean values determined for these 2 antibodies are 2.4 and 3.6 times lower, respectively, than the mean value for the control anti-CD151 antibody 14A2.H1.

In conclusion, the 2 tests confirm that the anti-integrin $\alpha_{IIb}$ control antibody PM6/248 and the anti-CD151 control antibody 14A2.H1 are capable of bringing about platelet aggregation in vitro and of causing platelet activation (Roberts et al., 1995, Br. J. Haematol. 89: 853-860; Hornby et al., 1991, Br. J. Haematol. 79: 277-285). In contrast to the 14A2.H1 antibody, the anti-CD151 antibodies 203B6 and 214B2 cause very low levels of platelet aggregation and activation which are not significant in human clinical terms.

Example 7

Study of the Activity of Anti-CD151 Antibodies on the Growth of NCI-H441 Tumours In vivo NCI-H441 cells obtained from the ATCC are cultured in RPMI 1640 medium to which 10% FCS and 1% L-glutamine have been added. The cells are divided two days before grafting so as to obtain cells that are in the exponential growth phase on the day of grafting. Ten million NCI-H441 cells are implanted at a subcutaneous location in athymic Nude mice. Five days after grafting, the tumours are measurable and the animals bearing tumours of comparable size are distributed into groups of 6. The mice are treated, by the i.p. route, with a challenge antibody dose of 2 mg/mouse and then twice a week with a dose of 1 mg of antibody per mouse. The tumour volume is assessed twice a week and is calculated using the formula: $\pi/6 \times length \times width \times height$. Specific analysis of the data is carried out at each measurement, using a Mann-Whitney test.

The results presented in FIG. 19 demonstrate that the antibodies 203B6 and 214B2 are capable of significantly ($p<0.05$) inhibiting the growth, in vivo, of the NCI-H441 cells.

Example 8

Assessment of the Activity of Two Anti-CD151 Antibodies on Macrophage Function

Assessment of the expression of CD151 on cells of the blood shows that this molecule is expressed significantly on the lymphocytes and monocytes. In order to preclude any possible toxicity problems, the 214B2 and 203B6 antibodies were tested for a potential effect on macrophage activation. In view of the fact that secretion of TNFα is a marker of macrophage activation, the TNFα concentration of the supernatant from a culture of THP-1 cells, cultured in the presence or absence of the antibodies under test, was assessed by ELISA. The THP-1 cell line is a monocytic leukaemia line capable of differentiating into a macrophagic line in the presence of agents of the PMA or 1α,25-dihydroxyvitamin D3 type. This activation process is accompanied by very significant secretion of TNFα. For assessment of the antibodies, the THP-1 cells are seeded into 6-well plates in the presence or absence of PMA (250 nM) for 72 hours. After that incubation period, some of the cells are recovered in order to check the differentiation in the presence of PMA by microscopic observation or by FACS analysis of the CD14/CD11b markers. The antibodies under test (241B2 and 203B6) are added to the other wells for an additional period of 24 hours. The 9G4 antibody is used under the same conditions as isotype control. LPS (1 µg/ml) is used as a positive experimental control. The culture supernatants are then withdrawn, centrifuged and stored at −80° C. before being assayed for their TNFα content by means of an ELISA test.

The results shown in FIG. 20A indicate that, in the absence of PMA, the THP-1 cells are non-adherent, refringent and round. In the presence of PMA, these cells become adherent, which is clearly indicative of differentiation of the monocytes into macrophages. The FACS analyses (FIG. 20B) show that, in the absence of PMA, less than 20% of the THP-1 cells express CD11b or CD14. The cellular differentiation caused by the PMA is, as expected, associated with a significant increase in the cells expressing CD11b, which changes from 9 to 65%. CD14 expression is also substantially increased, with the number of positive cells changing from 20 to 37%. The validity of the assessment model employed having been demonstrated by this data, assessment of the anti-CD151 antibodies was carried out in this test. FIG. 20C shows that no TNFα production is observed when the THP-1 cells are cultured in the absence of the differentiation inducer. In contrast, very significant production of TNFα (100 to 200 pg/ml) is observed. As expected, the LPS introduced as positive experimental control also brings about the secretion of a high level of cytokine, this being the case in the presence or absence of the differentiation inducer.

None of the anti-CD151 antibodies assessed causes secretion of TNFα whatever the state of cellular differentiation.

Example 9

Assessment of Two Anti-CD151 Antibodies with Respect to Antigen Presentation Function In view of the fact that the CD151 molecule is widely expressed on antigen-presenting cells, a study was carried out in order to check the potential impact, on antigen presentation function, of a therapy directed against CD151. The experiment performed consists of monitoring the specific lymphocyte proliferation of the TT antigen when the tetanus toxoid protein is introduced into PBMCs. In this arrangement, the protein should be processed by the antigen-presenting cells and exhibited by those same cells in association with the molecules of the MHC. This antigen presentation to CD4+ or CD8+ lymphocytes will cause proliferation of antigen-specific clones. Any impact on antigen presentation will therefore manifest itself in modulation of lymphocyte proliferation. For this experiment, PBMCs are isolated by centrifuging total blood on a Ficoll gradient. The cells, having been washed twice with PBS, are counted and re-suspended, at a concentration of $0.25 \times 10^6$ cells/ml, in RPMI 1640 medium to which 10% FCS and 1% glutamine have been added. 100 µl of the cell suspension are seeded into each well of a 96-well plate in the presence of the antigen and the antibodies under test. The 214B2 and 203B6 antibodies are assessed at a final concentration of 10 µg/ml. The 9G4 antibody is introduced at the same final concentration as experimental isotype control. PHA (2.5 µg/ml in well), a polyclonal activator of lymphocyte proliferation, is used as positive proliferation control. Tetanus toxoid (TT) was selected as test antigen and is used at a final concentration of 100 µg/ml. The plates are incubated at 37° C. for 96 hours, at the end of which 0.25 µCi of $^3$H-thymidine are added to each well for an additional period of 24 hours. After incubation, the cells are collected on filters and the radioactivity is assessed.

The results shown in FIG. 21A indicate that, as expected, the PHA used as positive control causes very marked lymphocyte proliferation. The intensity of the signal agrees well with polyclonal activation of cell proliferation. The 9G4 included in the experiment as isotype control has no impact on cell proliferation in the absence or presence of PHA. Similarly, the two anti-CD151 antibodies tested do not, in either case, modify the proliferation. The TT antigen causes significant proliferation of part of the lymphocyte population (FIG. 21B). There is no impact on this proliferation in the presence of 9G4 or of the two anti-CD151 antibodies tested, which indicates that, under the conditions of the experiment, antigen presentation is not affected by the compounds tested.

Example 10

Cloning and Production of Chimeric and Humanized Antibodies

Chimeric formats of murine 203B6 and 214B2 Mabs were designed: they correspond to the light and heavy chain variable domains of the murine antibodies of interest, genetically fused to human Ckappa and either IgG1 and IgG4 constant domains. Similarly, the below described humanized forms are produced as human IgG1/kappa or IgG4/kappa molecules. All recombinant Mabs are produced upon transient transfection by using the HEK293/EBNA system with a pCEP4 expression vector (InVitrogen, US).

The entire nucleotide sequences corresponding to the variable domains of 203B6 and 214B2 Mabs light and heavy chains (chimeric or humanized) were synthesized by global gene synthesis (Genecust, Luxembourg). They were subcloned into a pCEP4 vector (InVitrogen, US) carrying the entire coding sequence of the constant domain of either the light [Ckappa] or the heavy [CH1-Hinge-CH2-CH3] chain of a human IgG1 or human IgG4 immunoglobulin. All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US).

Suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2.10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$ cells/ml. Cultivation process was monitored on the basis of cell viability and Mab production. Typically, cultures were maintained for 4 to 5 days. Mabs were purified using a conventional chromatography approach on a Protein A resin (GE Healthcare, US).

All different Mabs are produced at levels suitable with functional evaluations.

Example 11

Humanization of Mouse Anti-CD151 Antibody 214B2 Variable Domains

The heavy and light chain variable domains VH and VL from mouse 214B2 antibody were submitted to an immunogenetic analysis by using the IMGT libraries and tools. The below described humanization strategy is based on the unique IMGT numbering scheme (Lefranc, 1997). First, the selected mouse germlines for each domain was identified via a BLAST search against IMGT LIGM DB database, by using the DomainGapAlign tool. The mouse IGKV6-20*01 germline yielded 97.9% identity with the rearranged 214B2 V-region and IGKJ2*01 was fully identical to the 214B2 J-region (FIG. 22). Concerning the heavy chain, 214B2 V-region is most homologous to the mouse IGHVS 130*01 germline (about 96% identity, FIG. 22) and concerning the J-region, mouse IGHJ4*01 corresponds to the closest J germline gene (94% identity, one divergent residue, FIG. 22). The Diversity D-germline gene corresponds to mouse IGHD5-1*01, it corresponds essentially to CDR3.

As an example of mouse 214B2 Mab humanization, a conventional strategy by CDR-grafting is described below. Each heavy and light chain is humanized individually and evaluated by co-expression either with its respective chimeric or humanized counterpart.

Humanization of 214B2 Light Chain VL

An atypical residue corresponding to Asn1 is identified, it exists in some mouse germline V-genes but never in human. Since it is located in proximity to CDR1, its modification into Glu as found in the selected human V-genes may me cautious and must be evaluated (FIG. 23). Otherwise, search for the most suitable human germline for grafting mouse 214B2 light chain CDRs identified two potential hits. The first corresponds to the human V-region showing the closest degree of homology with mouse IGKV6-20*01, it is human IGKV3-7*02 germline allele (68.4% identity). Nevertheless, its CDR1 is one amino acid longer than the one of 214B2, thus these CDR anchors are eventually not best suited for CDR1 grafting (see FIG. 23). A second human donor germline can be IGKV1D-39*01; it is 64% identical to mouse IGKV6-20*01 but CDR lengths are identical (6:3, FIG. 23). Criteria to evaluate the putative importance of each of the divergent residues between 214B2 VL and selected human V-gene include but are not restricted to: localization in the Vernier zone, location close to CDR anchors, presence at same position in another allele of same human germline group.

Considering IGKV6-20*01 V-gene, one residue within the Vernier zone is different as compared to both m214B2 and mIGKV6-20*02 (A84), it must be considered with high priority and conserved as mouse in a first instance (#1, FIG. 23). Otherwise, two important residues correspond to the CDR1 and CDR2 anchors V39 and N66, they are as well ranked with high priority and conserved as mouse in a first instance. Three residues are ranked as medium priority residues to consider because of their position close to CDR anchors (K24, Y68 and H103, FIG. 23). The remaining amino acids (ranked as #3) are likely to have a weak impact on the overall conformation of the humanized heavy chain and on CD151 recognition, they can easily be replaced by their human counterpart.

Considering IGKV1D-39*01 V-gene, one residue within the Vernier zone is different as compared to both m214B2 and mIGKV6-20*02 (A84), it must be considered with high priority and conserved as mouse in a first instance (#1, FIG. 23). Otherwise, two important residues correspond to the CDR1 and CDR2 anchors V39 and N66, they are as well ranked with high priority and conserved as mouse in a first instance. Five residues are ranked as medium priority residues to consider because of their position close to CDR anchors (K24, S40, Y68 and H103; FIG. 23) or in proximity to CDR1 (V3, FIG. 23). The remaining amino acids (ranked as #3) are likely to have a weak impact on the overall conformation of the humanized heavy chain and on CD151 recognition, they can easily be replaced by their human counterpart.

Considering the J-region, the human IGKJ2*01 gene contains 1 divergent residue (G) as compared to both m214B2 and mIGKJ2*01. Since this region corresponds essentially to FR4, it will be fully humanized in a first instance (FIG. 23).

The IMGT-CDR3 sequence (GQTYSFPYT) will be grafted per se without sequence modification.

Humanization of 214B2 Heavy Chain

Search for the most suitable human germline for grafting mouse 214B2 heavy chain CDRs identified one preferential hit corresponding to human IGHV1-2*02 V-gene allele. It is 66% identical to the mouse IGHVS130*01 germline gene, and CDR lengths are identical. Twenty-eight positions are divergent between 214B2_VH and IGHV1-2*02 in their FRs (FIG. 24). The closely related human IGHV1-46*03 germline may as well be suitable, it yielded the same amount of divergent residues, and similarly 15 out of 28 are located in FR3. Criteria to evaluate the putative importance of each of these 28 divergent residues include but are not restricted to: localization in the Vernier zone, location close to CDR anchors, presence at same position in another allele of same human germline group.

Considering IGHV1-2*02 V-gene, five residues within the Vernier zone are different as compared to both m214B2 and mIGHVS130*01 (I53, E55, A76, L78, V80), they must be considered with high priority and conserved as mouse in a first instance (#1, FIG. 24). Otherwise, N68 and E69 are ranked as medium priority residues to consider because of their position close to the CDR2 anchor (FIG. 24). The 21 remaining amino acids are likely to have a weak impact on the overall conformation of the humanized heavy chain and on CD151 recognition, they can easily be replaced by their human counterpart.

Considering IGHV1-46*03 V-gene, seven residues within the Vernier zone are different as compared to both m214B2 and mIGHVS130*01 (I53, E55, N66, A76, L78, V80, A87), they must be considered with high priority and conserved as mouse in a first instance (#1, FIG. 24). Otherwise, N68 and E69 are ranked as medium priority residues to consider because of their position close to the CDR2 anchor (FIG. 24). The 19 remaining amino acids are likely to have a weak impact on the overall conformation of the humanized heavy chain and on CD151 recognition, they can easily be replaced by their human counterpart.

Considering the J-region, the human IGHJ6*01 gene contains 3 divergent residues as compared to both m214B2 and mIGHJ4*01. Since this region corresponds essentially to FR4, it can be fully humanized in a first instance (FIG. 24).

The Diversity D-gene corresponding essentially to the sequence of CDR3 (ARARSFYYAMDC) will be grafted without modification.

All the above described amino acids are important positions to consider. All combinations of human versus mouse residue for each of these positions will be considered during the humanization process. Selection of humanized forms will be based on their degree of humanness and conserved functional in vitro and in vivo properties.

Example 12

Antibody Specificity by Western Blot

The specificity of the chimeric antibodies c214B2[IgG1] and c203B6[IgG1] was evaluated first by western blot. Briefly, purified recombinant large extracellular loop EC2 (2-8 µg) and HT-29 cell lysate (10-50 µg) were loaded on 12% acrylamide gels (BioRad). After electrophoresis under non reducing conditions, proteins were transferred to a nitrocellulose membrane, which was further incubated with the purified chimeric antibodies c214B2[IgG1] and c203B6[IgG1] at 0.5 µg/ml, and then with a peroxidase-conjugated rabbit polyclonal anti-human Ig (GE Healthcare). Proteins were detected by chemiluminescence. Both c214B2[IgG1] and c203B6[IgG1] were able to recognise full length CD151 by western blot (FIG. 10). Moreover, they were also shown to be specific for the large extracellular loop, as assessed by their reactivity for the recombinant EC2 loop (FIG. 25).

Example 13

Competition Experiments by ELISA

Cross-competition experiments were further performed by ELISA to evaluate the ability of the chimeric antibodies c214B2[IgG1] and c203B6[IgG1] to inhibit the binding of their corresponding murine forms to the recombinant EC2 loop. Briefly, 96-well ELISA plates were coated with recombinant EC2 at 5 µg/ml in PBS overnight at 4° C. Murine Mabs 203B6 and 214B2 at 80 ng/ml were further incubated in the absence or in the presence of increasing concentrations of their corresponding chimeric antibody forms, ranging from 0.01 to 20 µg/ml, for 1 h at 37° C. For control experiments, no murine antibody was added. Horseradish peroxidase-conjugated polyclonal goat anti-mouse IgG was added at a 1/5000 dilution in PBS and incubated for 1 h at 37° C. After incubation with the peroxidase substrate TMB for 10 min at room temperature, the reaction was stopped with 1 M sulfuric acid and the optical density at 450 nm was measured. FIG. 26 shows that the chimeric antibodies c214B2[IgG1] and c203B6[IgG1] were able to displace their murine forms of 214B2 and 203B6, respectively. $IC_{50}$ values, calculated by using the GraphPad Prism software, were 0.69 µg/ml and 0.71 µg/ml for c214B2[IgG1] and c203B6[IgG1], respectively.

Example 14

Binding of Chimeric Antibodies to Prostate Cancer Cells

The binding of the chimeric antibodies c203B6[IgG1] and c214B2[IgG1] to the prostate cancer cells PC3 was assessed by flow cytometry. Briefly, PC3 cells were incubated at $1.10^5$ cells/100 µl in PBS buffer containing 1% BSA and 0.01% sodium azide, in the presence of varying concentrations of c203B6[IgG1] or c214B2[IgG1] for 20 min at 4° C. Cells were further washed and incubated with an Alexa488-conjugated goat anti-human antibody (Molecular Probes, 1/500 dilution in PBS) for 20 min at 4° C. Labelled cells were washed, centrifuged and resuspended in the previous buffer (150 µl) before analysis with a Facscalibur cytometer (Becton Dickinson). Propidium iodide was added to perform analyses on viable cells only. Binding of chimeric antibodies c203B6 [IgG1] and c214B2[IgG1] to CD151 expressed at the surface of PC3 cells increased as a function of the antibody concentration (FIG. 27). A plateau was reached at 2.5 mg/ml and 5 µg/ml for c214B2[IgG1] and c203B6[IgG1], respectively, indicating that the binding of these antibodies to PC3 cells is highly specific.

Example 15

Antitumoral Activity of a Chimeric Antibody C214B2]IgG1] Against CD151 on the Prostate PC3 Xenograft Model An over-expression of CD151 has been previously shown on prostate tissue using a tissue array analysis. To determine whether prostate cancer cells would be responsive to a targeted-CD151 therapy, the chimeric c214B2[IgG1], directed against CD151, has been tested, in vivo, in the PC3 xenograft model. The PC3 cell line is an androgen-independent cell line provided by the ATCC and grown in F12K medium supplemented with 10% FCS. Five million PC3 cells were implanted s.c. to 6 week old male Swiss mice. Five days after implantation, tumors were measurable and mice were randomized into 2 groups of 6 mice before starting i.p. injections with the c214B2[IgG1] chimeric antibody. A 2 mg/dose of c214B2 was injected as a loading dose and then twice a week injections at 1 mg/dose were performed. Tumour volume was evaluated twice a week and calculated with the following formula: π/6×length×width×height. Results presented in FIG. 28 demonstrated that c214B2[IgG1], referred in this figure as c214B2, inhibited significantly in vivo tumor growth of PC3 cells. This result shows that targeting CD151 could be an efficient therapy for cancer.

The invention claimed is:

1. A composition comprising an isolated nucleic acid chosen from a DNA or RNA nucleic acid comprising a nucleotide sequence coding for a heavy chain variable domain of an antibody that is capable of binding to the CD151 protein, or coding for a heavy chain variable domain of a CD151-binding fragment of said antibody;

wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

2. A vector comprising a nucleic acid chosen from a DNA or RNA nucleic acid comprising a nucleotide sequence coding for a heavy chain variable domain of an antibody that is capable of binding to the CD151 protein, or coding for a heavy chain variable domain of a CD151-binding fragment of said antibody; wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

3. A cell host comprising a vector according to claim 2.

4. A transgenic animal, with the exception of a human being, comprising a cell according to claim 3.

5. A composition comprising an isolated nucleic acid chosen from a DNA or RNA nucleic acid comprising a nucleotide sequence coding for a light chain variable domain of an antibody that is capable of binding to the CD151 protein or coding for a light chain variable domain of a CD151-binding fragment of said antibody;

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

6. A vector comprising a nucleic acid chosen from a DNA or RNA nucleic acid comprising a nucleotide sequence coding for a light chain variable domain of an antibody that is capable of binding to the CD151 protein or coding for a light chain variable domain of a CD151-binding fragment of said antibody; wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

7. A cell host comprising a vector according to claim 6.

8. A transgenic animal, with the exception of a human being, comprising a cell according to claim 7.

9. A composition comprising isolated first and second nucleic acids comprising a first DNA or RNA sequence encoding a heavy chain variable domain and a second DNA or RNA sequence encoding a light chain variable domain, respectively, of an antibody that is capable of binding to the CD151 protein or of a CD151-binding fragment of said antibody, wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

10. A vector comprising isolated first and second nucleic acids comprising a first DNA or RNA sequence encoding a heavy chain variable domain and a second DNA or RNA sequence encoding a light chain variable domain, respectively, of an antibody that is capable of binding to the CD151 protein or of a CD151-binding fragment of said antibody, wherein the antibody that is capable of binding to the CD151 protein is chosen from:

an isolated antibody comprising i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

11. A cell host comprising a vector according to claim 10.

12. A transgenic animal, with the exception of a human being, comprising a cell according to claim 11.

13. A method of producing an antibody that is capable of binding to the CD151 protein or a CD151-binding fragment of said antibody, the method comprising: a) culturing a cell according to claim 11, in a suitable culture medium and under suitable culture conditions; and b) recovering the antibody, or the CD151-binding fragment of said antibody, thereby produced, from the culture medium or from said cultured cells; wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No. 87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

14. The composition of claim 9, wherein the isolated first and second nucleic acids are linked to separate vectors.

15. A recombinant expression vector comprising:

a) a DNA or RNA nucleic acid comprising a nucleotide sequence coding for a heavy chain variable domain of an antibody that is capable of binding to the CD151 protein or coding for a heavy chain variable domain of a CD151-binding fragment of said antibody; and b) a DNA or RNA nucleic acid comprising a nucleotide sequence coding for the light chain variable domain of said antibody or said CD151-binding fragment of said antibody;

wherein the antibody that is capable of binding to the CD151 protein is chosen from:

an isolated antibody comprising: i) a light chain comprising CDR-L1, CDR-L2, and CDR-L3, wherein: CDR-L1 is chosen from SEQ ID No. 43 and SEQ ID No. 85; CDR-L2 is chosen from SEQ ID No. 44 and SEQ ID No. 86; CDR-L3 is SEQ ID No. 45; and ii) a heavy chain comprising CDR-H1, CDR-H2 and CDR-H3, wherein CDR-H1 is chosen from SEQ ID No. 46 and SEQ ID No.

87; CDR-H2 is chosen from SEQ ID No. 47 and SEQ ID No. 88; CDR-H3 is chosen from SEQ ID No. 48 and SEQ ID No. 89;

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

16. The recombinant expression vector of claim 15 comprising:
  a) a DNA nucleic acid comprising a nucleotide sequence coding for a heavy chain variable domain of an antibody that is capable of binding to the CD151 protein or coding for a heavy chain variable domain of a CD151-binding fragment of said antibody; and
  b) a DNA nucleic acid comprising a nucleotide sequence coding for the light chain variable domain of said antibody or said CD151-binding fragment of said antibody;

wherein the antibody that is capable of binding to the CD151 protein is chosen from:

an isolated antibody comprising a light chain comprising SEQ ID No. 49 and a heavy chain comprising SEQ ID No. 50;

an isolated antibody comprising a light chain comprising SEQ ID No. 95 and a heavy chain comprising SEQ ID No. 96; and an isolated antibody comprising a light chain comprising SEQ ID No. 95 and a heavy chain comprising SEQ ID No. 97.

* * * * *

```
                            SEQUENCE LISTING

<160> NUMBER OF SEQ ID NOS: 119

<210> SEQ ID NO 1
<211> LENGTH: 10
<212> TYPE: PRT
<213> ORGANISM: mus musculus

<400> SEQUENCE: 1

Ala Ser Val Glu Tyr Tyr Gly Thr Ser Leu
1               5                   10

<210> SEQ ID NO 2
<211> LENGTH: 3
<212> TYPE: PRT
<213> ORGANISM: mus musculus

<400> SEQUENCE: 2

Glu Ala Ser
1

<210> SEQ ID NO 3
<211> LENGTH: 9
<212> TYPE: PRT
<213> ORGANISM: mus musculus

<400> SEQUENCE: 3

Gln Gln Ser Arg Lys Ala Pro Tyr Thr
1               5

<210> SEQ ID NO 4
<211> LENGTH: 8
<212> TYPE: PRT
<213> ORGANISM: mus musculus

<400> SEQUENCE: 4

Gly Phe Thr Phe Ser Thr Tyr Thr
1               5

<210> SEQ ID NO 5
<211> LENGTH: 8
<212> TYPE: PRT
<213> ORGANISM: mus musculus

<400> SEQUENCE: 5

Ile Ser Ser Gly Gly Gly Thr Thr
1               5

<210> SEQ ID NO 6
<211> LENGTH: 11
<212> TYPE: PRT
<213> ORGANISM: mus musculus

<400> SEQUENCE: 6

Ala Thr Pro Arg Ile Gly Thr Gly Phe Ala Tyr
1               5                   10

<210> SEQ ID NO 7
<211> LENGTH: 111
```

```
<212> TYPE: PRT
<213> ORGANISM: mus musculus

<400> SEQUENCE: 7

Asp Ile Val Leu Ser Gln Ser Pro Ala Ser Leu Ala Leu Ser Leu Gly
1               5                   10                  15

Gln Arg Ala Thr Ile Ser Cys Arg Ala Ser Ala Ser Val Glu Tyr Tyr
                20                  25                  30

Gly Thr Ser Leu Met His Trp Tyr Gln Gln Lys Pro Gly Gln Pro Pro
            35                  40                  45

Lys Leu Leu Ile Tyr Glu Ala Ser Asn Val Glu Ser Gly Val Pro Ala
        50                  55                  60

Arg Phe Ser Gly Ser Gly Ser Gly Thr Asp Phe Ser Leu Asn Ile His
65                  70                  75                  80

Pro Val Glu Glu Asp Asp Leu Ala Ile Tyr Phe Cys Gln Gln Ser Arg
                85                  90                  95

Lys Ala Pro Tyr Thr Phe Gly Gly Gly Thr Lys Leu Glu Ile Lys
                100                 105                 110

<210> SEQ ID NO 8
<211> LENGTH: 118
<212> TYPE: PRT
<213> ORGANISM: mus musculus

<400> SEQUENCE: 8

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
                20                  25                  30

Thr Met Ser Trp Val Arg Gln Thr Pro Glu Lys Arg Leu Glu Trp Val
            35                  40                  45

Ala Tyr Ile Ser Ser Gly Gly Gly Thr Thr Tyr Tyr Pro Asp Thr Val
        50                  55                  60

Lys Gly Arg Phe Thr Ile Ser Arg Asp Asn Ala Arg Asn Thr Leu Tyr
65                  70                  75                  80

Leu Gln Met Asn Ser Leu Lys Ser Glu Asp Thr Ala Met Tyr Tyr Cys
                85                  90                  95

Ala Thr Pro Arg Ile Gly Thr Gly Phe Ala Tyr Trp Gly Gln Gly Thr
                100                 105                 110

Leu Val Thr Val Ser Ala
        115

<210> SEQ ID NO 9
<211> LENGTH: 30
<212> TYPE: DNA
<213> ORGANISM: mus musculus

<400> SEQUENCE: 9
gccagtgttg aatattatgg cacaagttta                                   30

<210> SEQ ID NO 10
<211> LENGTH: 9
<212> TYPE: DNA
<213> ORGANISM: mus musculus

<400> SEQUENCE: 10 gaagcatcc                                                           9

<210> SEQ ID NO 11
```

```
<211> LENGTH: 27
<212> TYPE: DNA
<213> ORGANISM: mus musculus

<400> SEQUENCE: 11
cagcaaagta ggaaggctcc ttacacg                                          27

<210> SEQ ID NO 12
<211> LENGTH: 24
<212> TYPE: DNA
<213> ORGANISM: mus musculus

<400> SEQUENCE: 12
ggattcactt tcagtaccta tacc                                             24

<210> SEQ ID NO 13
<211> LENGTH: 24
<212> TYPE: DNA
<213> ORGANISM: mus musculus

<400> SEQUENCE: 13
attagtagtg gtggtggtac tacc                                             24

<210> SEQ ID NO 14
<211> LENGTH: 33
<212> TYPE: DNA
<213> ORGANISM: mus musculus

<400> SEQUENCE: 14
gcaactcccc gaattgggac ggggtttgct tac                                   33

<210> SEQ ID NO 15
<211> LENGTH: 333
<212> TYPE: DNA
<213> ORGANISM: mus musculus

<400> SEQUENCE: 15
gacattgtgc tcagccaatc tccagcttct ttggctctgt ctctggggca gagagccacc      60
atctcctgca gagccagtgc cagtgttgaa tattatggca caagtttaat gcattggtac     120
caacagaaac caggacagcc acccaaactc ctcatctatg aagcatccaa cgtagaatct     180
ggggtccctg ccaggtttag tggcagtggg tctgggacag acttcagcct caacatccat     240
cctgtggagg aggatgatct tgcaatatat ttctgtcagc aaagtaggaa ggctccttac     300
acgttcggag ggggaccaa gctggaaata aaa                                   333

<210> SEQ ID NO 16
<211> LENGTH: 354
<212> TYPE: DNA
<213> ORGANISM: mus musculus

<400> SEQUENCE: 16
gaagtgaagc tggtggagtc tggggagagt ttagtgcagc ctggagggtc cctgaaactc      60
tcctgtgcag cctctggatt cactttcagt acctatacca tgtcttgggt tcgccagact     120
ccagagaaga ggctggagtg ggtcgcatac attagtagtg gtggtggtac tacctattat     180
ccagacactg taaagggccg attcaccatc tccagagaca tgccaggaa caccctgtac     240 ctgcaaatga acagtctgaa gtctgaggac acggccatgt attactgtgc aactccccga     300
attgggacgg ggtttgctta ctggggccaa gggactctgg tcactgtctc tgct           354

<210> SEQ ID NO 17
```

```
<211> LENGTH: 6
<212> TYPE: PRT
<213> ORGANISM: mus musculus

<400> SEQUENCE: 17

Gln Asn Val Gly Ile Ala
1               5

<210> SEQ ID NO 18
<211> LENGTH: 3
<212> TYPE: PRT
<213> ORGANISM: mus musculus

<400> SEQUENCE: 18

Ser Ala Ser
1

<210> SEQ ID NO 19
<211> LENGTH: 8
<212> TYPE: PRT
<213> ORGANISM: mus musculus

<400> SEQUENCE: 19

Gln Gln Tyr Ser Ser Asn Pro Thr
1               5

<210> SEQ ID NO 20
<211> LENGTH: 10
<212> TYPE: PRT
<213> ORGANISM: mus musculus

<400> SEQUENCE: 20

Gly Phe Thr Leu Ser Thr Ser Gly Met Gly
1               5                   10

<210> SEQ ID NO 21
<211> LENGTH: 7
<212> TYPE: PRT
<213> ORGANISM: mus musculus

<400> SEQUENCE: 21

Ile Tyr Trp Asp Asp Asp Lys
1               5

<210> SEQ ID NO 22
<211> LENGTH: 15
<212> TYPE: PRT
<213> ORGANISM: mus musculus

<400> SEQUENCE: 22

Ala Arg Arg Asp His Tyr Gly Asp Tyr Ser Tyr Ala Met Asp Tyr
1               5                   10                  15

<210> SEQ ID NO 23
<211> LENGTH: 106
<212> TYPE: PRT
<213> ORGANISM: mus musculus

<400> SEQUENCE: 23

Asp Ile Val Met Thr Gln Ser Gln Lys Phe Met Ser Thr Ser Glu Gly
1               5                   10                  15

Asp Arg Val Ser Ile Thr Cys Lys Ala Ser Gln Asn Val Gly Ile Ala
                20                  25                  30

Val Ala Trp Tyr Gln Gln Lys Pro Gly Gln Ser Pro Lys Leu Leu Ile
            35                  40                  45
```

```
Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Asn Pro Thr
                85                  90                  95

Phe Gly Ala Gly Thr Lys Leu Glu Leu Lys
            100                 105

<210> SEQ ID NO 24
<211> LENGTH: 123
<212> TYPE: PRT
<213> ORGANISM: mus musculus

<400> SEQUENCE: 24

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Thr Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Asp His Tyr Gly Asp Tyr Ser Tyr Ala Met Asp Tyr
            100                 105                 110

Trp Gly Gln Gly Thr Ser Val Thr Val Ser Ser
        115                 120

<210> SEQ ID NO 25
<211> LENGTH: 18
<212> TYPE: DNA
<213> ORGANISM: mus musculus

<400> SEQUENCE: 25
cagaatgtgg gtattgct                                                    18

<210> SEQ ID NO 26
<211> LENGTH: 9
<212> TYPE: DNA
<213> ORGANISM: mus musculus

<400> SEQUENCE: 26 tcggcatcc                                                               9

<210> SEQ ID NO 27
<211> LENGTH: 24
<212> TYPE: DNA
<213> ORGANISM: mus musculus

<400> SEQUENCE: 27
cagcaatata gcagcaatcc cacg                                             24

<210> SEQ ID NO 28
<211> LENGTH: 30
<212> TYPE: DNA
<213> ORGANISM: mus musculus
```

```
<400> SEQUENCE: 28
ggttttacac tgagtacttc tggtatgggt                                    30

<210> SEQ ID NO 29
<211> LENGTH: 21
<212> TYPE: DNA
<213> ORGANISM: mus musculus

<400> SEQUENCE: 29
atttactggg atgatgacaa g                                             21

<210> SEQ ID NO 30
<211> LENGTH: 45
<212> TYPE: DNA
<213> ORGANISM: mus musculus

<400> SEQUENCE: 30
gctcgaagag accactatgg tgactactcc tatgctatgg actac                   45

<210> SEQ ID NO 31
<211> LENGTH: 318
<212> TYPE: DNA
<213> ORGANISM: mus musculus

<400> SEQUENCE: 31
gacattgtga tgacccagtc tcaaaaattc atgtccacat cagaaggaga cagggtcagc   60
atcacctgca aggccagtca gaatgtgggt attgctgtag cctggtatca acagaaacca  120
ggacaatctc ctaaactact gatttactcg gcatccaatc gctacactgg agtccctgat  180
cgcttcacag gcagtggatc tgggacagat ttcactctca ccatcagcaa tatgcagtct  240
gaagacctgg cagattattt ctgccagcaa tatagcagca atcccacgtt cggtgctggg  300
accaagttgg agctgaaa                                                318

<210> SEQ ID NO 32
<211> LENGTH: 369
<212> TYPE: DNA
<213> ORGANISM: mus musculus

<400> SEQUENCE: 32
caggttactc tgaaagagtc tggccctggg atattgcagc cctcccagac cctcagtctg   60
acttgttctt tctctggttt tacactgagt acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgca gatactgcca catactactg tgctcgaaga  300
gaccactatg gtgactactc ctatgctatg gactactggg gtcaaggaac ctcagtcacc  360
gtctcctca                                                          369

<210> SEQ ID NO 33
<211> LENGTH: 10
<212> TYPE: PRT
<213> ORGANISM: mus musculus

<400> SEQUENCE: 33

Ala Ser Val Asp Tyr Tyr Gly Thr Ser Leu
1               5                   10

<210> SEQ ID NO 34
```

```
<211> LENGTH: 8
<212> TYPE: PRT
<213> ORGANISM: mus musculus

<400> SEQUENCE: 34

Ile Ser Ser Gly Gly Val Thr Thr
1               5

<210> SEQ ID NO 35
<211> LENGTH: 11
<212> TYPE: PRT
<213> ORGANISM: mus musculus

<400> SEQUENCE: 35

Thr Ser Pro Arg Thr Gly Thr Gly Phe Ala Tyr
1               5                   10

<210> SEQ ID NO 36
<211> LENGTH: 111
<212> TYPE: PRT
<213> ORGANISM: mus musculus

<400> SEQUENCE: 36

Asp Ile Val Leu Thr Gln Ser Pro Ala Ser Leu Ala Leu Ser Leu Gly
1               5                   10                  15

Gln Arg Ala Thr Ile Ser Cys Arg Ala Ser Ala Ser Val Asp Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Glu Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Leu Ala Ile Tyr Phe Cys Gln Gln Ser Arg
                85                  90                  95

Lys Ala Pro Tyr Thr Phe Gly Gly Gly Thr Lys Leu Glu Ile Lys
            100                 105                 110

<210> SEQ ID NO 37
<211> LENGTH: 118
<212> TYPE: PRT
<213> ORGANISM: mus musculus

<400> SEQUENCE: 37

Glu Val Lys Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Tyr Ile Ser Ser Gly Gly Val Thr Thr Tyr Pro Asp Thr Ile
    50                  55                  60

Lys Gly Arg Phe Thr Ile Ser Arg Asp Asn Ala Lys Asn Thr Leu Phe
65                  70                  75                  80

Leu Gln Met Asn Ser Leu Lys Ser Glu Asp Thr Ala Met Tyr Tyr Cys
                85                  90                  95

Thr Ser Pro Arg Thr Gly Thr Gly Phe Ala Tyr Trp Gly Gln Gly Thr
            100                 105                 110

Leu Val Thr Val Ser Ala
            115
```

<210> SEQ ID NO 38
<211> LENGTH: 30
<212> TYPE: DNA
<213> ORGANISM: mus musculus

<400> SEQUENCE: 38
gcaagtgttg attattatgg cacaagttta                                      30

<210> SEQ ID NO 39
<211> LENGTH: 24
<212> TYPE: DNA
<213> ORGANISM: mus musculus

<400> SEQUENCE: 39
attagtagtg gtggtgttac tacc                                            24

<210> SEQ ID NO 40
<211> LENGTH: 33
<212> TYPE: DNA
<213> ORGANISM: mus musculus

<400> SEQUENCE: 40
acaagccccc gaactgggac ggggtttgct tac                                  33

<210> SEQ ID NO 41
<211> LENGTH: 333
<212> TYPE: DNA
<213> ORGANISM: mus musculus

<400> SEQUENCE: 41
gacattgtgc tcacccaatc tccagcttct ttggctctgt ctctggggca gagagccacc     60
atctcctgca gagccagtgc aagtgttgat tattatggca caagtttaat gcagtggtac    120
caacagaaac caggacagcc acccaaactc ctcatctatg aagcatccaa cgtagaatct    180
ggggtccctg ccaggtttag tggcagtggg tctgggacag acttcagcct caacatccat    240
cctgtggagg aggatgatct tgcaatatat ttctgtcagc aaagtaggaa ggctccttac    300
acgttcggag gggggaccaa gctggaaata aaa                                 333

<210> SEQ ID NO 42
<211> LENGTH: 354
<212> TYPE: DNA
<213> ORGANISM: mus musculus

<400> SEQUENCE: 42
gaagtgaagc tggtggagtc tgggggagat ttagtgcagc ctggagggtc cctgaaactc     60
tcctgtgcag cctctggatt cactttcagt acctatacca tgtcttgggt tcgccagact    120
ccagagaaga ggctggagtg ggtcgcatac attagtagtg gtggtgttac tacctactat    180
ccagacacta taaagggccg attcaccatc tccagagaca tgccaagaa cacctgttc     240 ctgcaaatga acagtctgaa gtctgaagac acggccatgt attactgtac aagccccga    300 actgggacgg ggtttgctta ctggggccaa gggactctgg tcactgtctc tgct          354

<210> SEQ ID NO 43
<211> LENGTH: 6
<212> TYPE: PRT
<213> ORGANISM: mus musculus

<400> SEQUENCE: 43

Glu Asn Val Gly Thr Tyr

<210> SEQ ID NO 44
<211> LENGTH: 3
<212> TYPE: PRT
<213> ORGANISM: mus musculus

<400> SEQUENCE: 44

Gly Ala Ser
1

<210> SEQ ID NO 45
<211> LENGTH: 9
<212> TYPE: PRT
<213> ORGANISM: mus musculus

<400> SEQUENCE: 45

Gly Gln Thr Tyr Ser Phe Pro Tyr Thr
1               5

<210> SEQ ID NO 46
<211> LENGTH: 8
<212> TYPE: PRT
<213> ORGANISM: mus musculus

<400> SEQUENCE: 46

Gly Tyr Thr Phe Thr Ser Ser Ser
1               5

<210> SEQ ID NO 47
<211> LENGTH: 8
<212> TYPE: PRT
<213> ORGANISM: mus musculus

<400> SEQUENCE: 47

Ile His Pro Asn Ser Gly Asn Thr
1               5

<210> SEQ ID NO 48
<211> LENGTH: 12
<212> TYPE: PRT
<213> ORGANISM: mus musculus

<400> SEQUENCE: 48

Ala Arg Ala Arg Ser Phe Tyr Tyr Ala Met Asp Cys
1               5                   10

<210> SEQ ID NO 49
<211> LENGTH: 107
<212> TYPE: PRT
<213> ORGANISM: mus musculus

<400> SEQUENCE: 49

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

```
Glu Asp Leu Ala Asp Tyr His Cys Gly Gln Thr Tyr Ser Phe Pro Tyr
                85                  90                  95

Thr Phe Gly Gly Gly Thr Lys Leu Glu Ile Lys
        100                 105
```

<210> SEQ ID NO 50
<211> LENGTH: 119
<212> TYPE: PRT
<213> ORGANISM: mus musculus

<400> SEQUENCE: 50

```
Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Ser Met His Trp Ala Lys Gln Arg Pro Gly Gln Gly Leu Glu Trp Ile
        35                  40                  45

Gly Glu Ile His Pro Asn Ser Gly Asn Thr Asn Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Ser Ser Glu Asp Ser Ala Val Tyr Tyr Cys
                85                  90                  95

Ala Arg Ala Arg Ser Phe Tyr Tyr Ala Met Asp Cys Trp Gly Gln Gly
            100                 105                 110

Thr Ser Val Thr Val Ser Ser
        115
```

<210> SEQ ID NO 51
<211> LENGTH: 18
<212> TYPE: DNA
<213> ORGANISM: mus musculus

<400> SEQUENCE: 51
gagaatgtgg gtacttat                                                    18

<210> SEQ ID NO 52
<211> LENGTH: 9
<212> TYPE: DNA
<213> ORGANISM: mus musculus

<400> SEQUENCE: 52 ggggcatcc                                                               9

<210> SEQ ID NO 53
<211> LENGTH: 27
<212> TYPE: DNA
<213> ORGANISM: mus musculus

<400> SEQUENCE: 53
ggacagactt acagctttcc gtacacg                                          27

<210> SEQ ID NO 54
<211> LENGTH: 24
<212> TYPE: DNA
<213> ORGANISM: mus musculus

<400> SEQUENCE: 54
ggctacacct tcaccagctc ctcg                                             24

<210> SEQ ID NO 55

```
<211> LENGTH: 24
<212> TYPE: DNA
<213> ORGANISM: mus musculus

<400> SEQUENCE: 55
attcatccta atagtggtaa tact                                             24

<210> SEQ ID NO 56
<211> LENGTH: 36
<212> TYPE: DNA
<213> ORGANISM: mus musculus

<400> SEQUENCE: 56
gcaagggcga ggtcctttta ctatgctatg gactgc                                36

<210> SEQ ID NO 57
<211> LENGTH: 321
<212> TYPE: DNA
<213> ORGANISM: mus musculus

<400> SEQUENCE: 57
aacattgtaa tgacccaatc tcccaaatcc atgtccatgt cagtaggaga gagggtcacc      60
ttgagctgca aggccagtga aatgtgggt  acttatgtat cctggtatca acagaaacca     120
gagcagtctc ctaaactact aatatacggg gcatccaacc ggtacactgg ggtccccgat     180
cgcttcacag gcagtgggtc tgcaacagat ttcacactga ccatcagcag tgtgcaggct     240
gaagaccttg cagactatca ctgtggacag acttacagct ttccgtacac gttcggaggg     300
gggaccaagc tggaaataaa a                                               321

<210> SEQ ID NO 58
<211> LENGTH: 357
<212> TYPE: DNA
<213> ORGANISM: mus musculus

<400> SEQUENCE: 58
caggtccaac tgcagcagcc tgggtctgtg ctggtgaggc ctggagcttc agtgaagctg      60
tcctgcaagg cttctggcta caccttcacc agctcctcga tgcactgggc gaagcagagg     120
cctggacaag gccttgagtg gatcggagag attcatccta atagtggtaa tactaacaac     180
aatgagaagt tcaagggcaa ggccacactg actgtagaca catcctccag cacagcctac     240
gtggatctca gcagcctgtc atctgaggac tctgcggtct attactgtgc aagggcgagg     300 tcctttttact atgctatgga ctgctggggt caaggaacct cagtcaccgt ctcctca       357

<210> SEQ ID NO 59
<211> LENGTH: 15
<212> TYPE: PRT
<213> ORGANISM: mus musculus

<400> SEQUENCE: 59

Arg Ala Ser Ala Ser Val Glu Tyr Tyr Gly Thr Ser Leu Met His
1               5                   10                  15

<210> SEQ ID NO 60
<211> LENGTH: 7
<212> TYPE: PRT
<213> ORGANISM: mus musculus

<400> SEQUENCE: 60

Glu Ala Ser Asn Val Glu Ser
1               5
```

<210> SEQ ID NO 61
<211> LENGTH: 6
<212> TYPE: PRT
<213> ORGANISM: mus musculus

<400> SEQUENCE: 61

Ser Thr Tyr Thr Met Ser
1               5

<210> SEQ ID NO 62
<211> LENGTH: 17
<212> TYPE: PRT
<213> ORGANISM: mus musculus

<400> SEQUENCE: 62

Tyr Ile Ser Ser Gly Gly Gly Thr Thr Tyr Tyr Pro Asp Thr Val Lys
1               5                   10                  15

Gly

<210> SEQ ID NO 63
<211> LENGTH: 9
<212> TYPE: PRT
<213> ORGANISM: mus musculus

<400> SEQUENCE: 63

Pro Arg Ile Gly Thr Gly Phe Ala Tyr
1               5

<210> SEQ ID NO 64
<211> LENGTH: 45
<212> TYPE: DNA
<213> ORGANISM: mus musculus

<400> SEQUENCE: 64
agagccagtg ccagtgttga atattatggc acaagtttaa tgcat           45

<210> SEQ ID NO 65
<211> LENGTH: 21
<212> TYPE: DNA
<213> ORGANISM: mus musculus

<400> SEQUENCE: 65
gaagcatcca acgtagaatc t                                     21

<210> SEQ ID NO 66
<211> LENGTH: 18
<212> TYPE: DNA
<213> ORGANISM: mus musculus

<400> SEQUENCE: 66
agtacctata ccatgtct                                         18

<210> SEQ ID NO 67
<211> LENGTH: 51
<212> TYPE: DNA
<213> ORGANISM: mus musculus

<400> SEQUENCE: 67
tacattagta gtggtggtgg tactacctat tatccagaca ctgtaaaggg c     51

<210> SEQ ID NO 68
<211> LENGTH: 27
<212> TYPE: DNA
<213> ORGANISM: mus musculus

<400> SEQUENCE: 68
ccccgaattg ggacggggtt tgcttac                                          27

<210> SEQ ID NO 69
<211> LENGTH: 11
<212> TYPE: PRT
<213> ORGANISM: mus musculus

<400> SEQUENCE: 69

Lys Ala Ser Gln Asn Val Gly Ile Ala Val Ala
1               5                   10

<210> SEQ ID NO 70
<211> LENGTH: 7
<212> TYPE: PRT
<213> ORGANISM: mus musculus

<400> SEQUENCE: 70

Ser Ala Ser Asn Arg Tyr Thr
1               5

<210> SEQ ID NO 71
<211> LENGTH: 8
<212> TYPE: PRT
<213> ORGANISM: mus musculus

<400> SEQUENCE: 71

Ser Thr Ser Gly Met Gly Val Ser
1               5

<210> SEQ ID NO 72
<211> LENGTH: 16
<212> TYPE: PRT
<213> ORGANISM: mus musculus

<400> SEQUENCE: 72

His Ile Tyr Trp Asp Asp Asp Lys Arg Tyr Asn Pro Ser Leu Lys Ser
1               5                   10                  15

<210> SEQ ID NO 73
<211> LENGTH: 13
<212> TYPE: PRT
<213> ORGANISM: mus musculus

<400> SEQUENCE: 73

Arg Asp His Tyr Gly Asp Tyr Ser Tyr Ala Met Asp Tyr
1               5                   10

<210> SEQ ID NO 74
<211> LENGTH: 33
<212> TYPE: DNA
<213> ORGANISM: mus musculus

<400> SEQUENCE: 74
aaggccagtc agaatgtggg tattgctgta gcc                                   33

<210> SEQ ID NO 75
<211> LENGTH: 21
<212> TYPE: DNA
<213> ORGANISM: mus musculus

<400> SEQUENCE: 75
tcggcatcca atcgctacac t                                                21

-continued

<210> SEQ ID NO 76
<211> LENGTH: 24
<212> TYPE: DNA
<213> ORGANISM: mus musculus

<400> SEQUENCE: 76
agtacttctg gtatgggtgt gagc                                              24

<210> SEQ ID NO 77
<211> LENGTH: 48
<212> TYPE: DNA
<213> ORGANISM: mus musculus

<400> SEQUENCE: 77
cacatttact gggatgatga caagcgctat aacccatccc tgaagagc                    48

<210> SEQ ID NO 78
<211> LENGTH: 39
<212> TYPE: DNA
<213> ORGANISM: mus musculus

<400> SEQUENCE: 78
agagaccact atggtgacta ctcctatgct atggactac                              39

<210> SEQ ID NO 79
<211> LENGTH: 15
<212> TYPE: PRT
<213> ORGANISM: mus musculus

<400> SEQUENCE: 79

Arg Ala Ser Ala Ser Val Asp Tyr Tyr Gly Thr Ser Leu Met Gln
1               5                   10                  15

<210> SEQ ID NO 80
<211> LENGTH: 17
<212> TYPE: PRT
<213> ORGANISM: mus musculus

<400> SEQUENCE: 80

Tyr Ile Ser Ser Gly Gly Val Thr Thr Tyr Tyr Pro Asp Thr Ile Lys
1               5                   10                  15

Gly

<210> SEQ ID NO 81
<211> LENGTH: 9
<212> TYPE: PRT
<213> ORGANISM: mus musculus

<400> SEQUENCE: 81

Pro Arg Thr Gly Thr Gly Phe Ala Tyr
1               5

<210> SEQ ID NO 82
<211> LENGTH: 45
<212> TYPE: DNA
<213> ORGANISM: mus musculus

<400> SEQUENCE: 82
agagccagtg caagtgttga ttattatggc acaagtttaa tgcag                       45

<210> SEQ ID NO 83
<211> LENGTH: 51
<212> TYPE: DNA
<213> ORGANISM: mus musculus -continued

```
<400> SEQUENCE: 83
tacattagta gtggtggtgt tactacctac tatccagaca ctataaaggg c        51

<210> SEQ ID NO 84
<211> LENGTH: 27
<212> TYPE: DNA
<213> ORGANISM: mus musculus

<400> SEQUENCE: 84
ccccgaactg ggacggggtt tgcttac                                   27

<210> SEQ ID NO 85
<211> LENGTH: 11
<212> TYPE: PRT
<213> ORGANISM: mus musculus

<400> SEQUENCE: 85

Lys Ala Ser Glu Asn Val Gly Thr Tyr Val Ser
1               5                   10

<210> SEQ ID NO 86
<211> LENGTH: 11
<212> TYPE: PRT
<213> ORGANISM: mus musculus

<400> SEQUENCE: 86

Gly Ala Ser Asn Arg Tyr Thr Gly Val Pro Asp
1               5                   10

<210> SEQ ID NO 87
<211> LENGTH: 6
<212> TYPE: PRT
<213> ORGANISM: mus musculus

<400> SEQUENCE: 87

Thr Ser Ser Ser Met His
1               5

<210> SEQ ID NO 88
<211> LENGTH: 17
<212> TYPE: PRT
<213> ORGANISM: mus musculus

<400> SEQUENCE: 88

Glu Ile His Pro Asn Ser Gly Asn Thr Asn Asn Asn Glu Lys Phe Lys
1               5                   10                  15

Gly

<210> SEQ ID NO 89
<211> LENGTH: 10
<212> TYPE: PRT
<213> ORGANISM: mus musculus

<400> SEQUENCE: 89

Ala Arg Ser Phe Tyr Tyr Ala Met Asp Cys
1               5                   10

<210> SEQ ID NO 90
<211> LENGTH: 33
<212> TYPE: DNA
<213> ORGANISM: mus musculus

<400> SEQUENCE: 90
```

```
aaggccagtg agaatgtggg tacttatgta tcc                                    33

<210> SEQ ID NO 91
<211> LENGTH: 33
<212> TYPE: DNA
<213> ORGANISM: mus musculus

<400> SEQUENCE: 91 gggcatcca accggtacac tggggtcccc gat                                     33

<210> SEQ ID NO 92
<211> LENGTH: 18
<212> TYPE: DNA
<213> ORGANISM: mus musculus

<400> SEQUENCE: 92
accagctcct cgatgcac                                                     18

<210> SEQ ID NO 93
<211> LENGTH: 51
<212> TYPE: DNA
<213> ORGANISM: mus musculus

<400> SEQUENCE: 93
gagattcatc ctaatagtgg taatactaac aacaatgaga agttcaaggg c                51

<210> SEQ ID NO 94
<211> LENGTH: 30
<212> TYPE: DNA
<213> ORGANISM: mus musculus

<400> SEQUENCE: 94
gcgaggtcct tttactatgc tatggactgc                                        30

<210> SEQ ID NO 95
<211> LENGTH: 214
<212> TYPE: PRT
<213> ORGANISM: Artificial sequence
<220> FEATURE:
<223> OTHER INFORMATION: Chimeric anti-CD151 antibody light chain
      derived from the murine 214B2 monoclonal antibody

<400> SEQUENCE: 95

Asn Ile Val Met Thr Gln Ser Pro Lys Ser Met Ser Met Ser Val Gly
  1               5                  10                  15

Glu Arg Val Thr Leu Ser Cys Lys Ala Ser Glu Asn Val Gly Thr Tyr
                 20                  25                  30

Val Ser Trp Tyr Gln Gln Lys Pro Glu Gln Ser Pro Lys Leu Leu Ile
             35                  40                  45

Tyr Gly Ala Ser Asn Arg Tyr Thr Gly Val Pro Asp Arg Phe Thr Gly
         50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Thr Tyr Ser Phe Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 449
<212> TYPE: PRT
<213> ORGANISM: Artificial sequence
<220> FEATURE:
<223> OTHER INFORMATION: Chimeric anti-CD151 antibody heavy chain
      derived from the murine 214B2 monoclonal antibody

<400> SEQUENCE: 96

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
                20                  25                  30

Ser Met His Trp Ala Lys Gln Arg Pro Gly Gln Gly Leu Glu Trp Ile
            35                  40                  45

Gly Glu Ile His Pro Asn Ser Gly Asn Thr Asn Asn Glu Lys Phe
        50                  55                  60

Lys Gly Lys Ala Thr Leu Thr Val Asp Thr Ser Ser Ser Thr Ala Tyr
65                  70                  75                  80

Val Asp Leu Ser Ser Leu Ser Ser Glu Asp Ser Ala Val Tyr Tyr Cys
                85                  90                  95

Ala Arg Ala Arg Ser Phe Tyr Tyr Ala Met Asp Cys Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 97
<211> LENGTH: 446
<212> TYPE: PRT
<213> ORGANISM: Artificial sequence
<220> FEATURE:
<223> OTHER INFORMATION: Chimeric anti-CD151 antibody heavy chain
      derived from the murine 214B2 monoclonal antibody

<400> SEQUENCE: 97

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Ser Met His Trp Ala Lys Gln Arg Pro Gly Gln Gly Leu Glu Trp Ile
        35                  40                  45

Gly Glu Ile His Pro Asn Ser Gly Asn Thr Asn Asn Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Ser Ser Glu Asp Ser Ala Val Tyr Tyr Cys
                85                  90                  95

Ala Arg Ala Arg Ser Phe Tyr Tyr Ala Met Asp Cys Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
```

```
                   195                 200                 205
Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 98
<211> LENGTH: 642
<212> TYPE: DNA
<213> ORGANISM: Artificial sequence
<220> FEATURE:
<223> OTHER INFORMATION: Chimeric anti-CD151 antibody light chain
      derived from the murine 214B2 monoclonal antibody

<400> SEQUENCE: 98
aacatcgtga tgacccagag ccccaagagc atgagcatga gcgtgggcga gagagtgacc        60
ctgagctgca aggccagcga gaacgtgggc acctacgtgt cctggtatca gcagaagccc       120
gagcagtccc ccaagctgct gatctacggc gccagcaacc ggtacaccgg cgtgcccgac       180
agattcaccg gcagcggcag cgccaccgac ttcaccctga ccatcagcag cgtgcaggcc       240
gaggacctgg ccgactacca ctgcggccag acctacagct cccctacac ctttggcggc        300 ggaacaaagc tggaaatcaa gcgtacggtg gccgctccca gcgtgttcat cttccccca        360 agcgacgagc agctgaagag cggcaccgcc agcgtggtgt gtctgctgaa caacttctac       420
cccagggagg ccaaggtgca gtggaaggtg gacaacgccc tgcagagcgg caacagccag       480
gagagcgtca ccgagcagga cagcaaggac tccacctaca gcctgagcag caccctgacc       540
ctgagcaagg ccgactacga gaagcacaag gtgtacgcct gtgaggtgac ccaccagggc       600
ctgtccagcc ccgtgaccaa gagcttcaac agggggcgagt gc                         642
```

<210> SEQ ID NO 99
<211> LENGTH: 1347
<212> TYPE: DNA
<213> ORGANISM: Artificial sequence
<220> FEATURE:
<223> OTHER INFORMATION: Chimeric anti-CD151 antibody heavy chain derived from the murine 214B2 monoclonal antibody

<400> SEQUENCE: 99

```
caggtgcagc tgcagcagcc cggcagcgtg ctggtgagac ctggcgcctc cgtgaagctg      60
tcctgcaagg cctccggcta caccttcacc agcagcagca tgcactgggc caagcagcgg     120
ccaggccagg gactggaatg gatcggcgag atccacccca cagcggcaa caccaacaac      180
aacgagaagt tcaagggcaa ggccaccctg accgtggaca ccagcagctc caccgcctac     240
gtggacctga gcagcctgtc cagcgaggac agcgccgtgt actactgcgc cagagccaga     300
tccttctact acgctatgga ctgctggggc cagggcacca gcgtgaccgt gtccagcgcc     360
agcaccaagg gcccaagcgt gttcccgcta gcccccagca gcaagagcac cagcggcggc     420
acagccgccc tgggctgcct ggtgaaggac tacttccccg agcccgtgac cgtgtcctgg     480
aacagcggag ccctgacctc cggcgtgcac accttccccg ccgtgctgca gagcagcggc     540
ctgtacagcc tgagcagcgt ggtgaccgtg cccagcagca gcctgggcac ccagacctac     600
atctgtaacg tgaaccacaa gcccagcaac accaaggtgg acaagagagt ggagcccaag     660
agctgtgaca agacccacac ctgccccccc tgcccagccc ccgagctgct gggcggaccc     720
agcgtgttcc tgttccccccc caagcccaag gacaccctga tgatcagcag aaccccgag   780
gtgacctgtg tggtggtgga cgtgtcccac gaggacccag aggtgaagtt caactggtac     840
gtggacggcg tggaggtgca caacgccaag accaagccca gaggagca gtacaacagc      900
acctacaggg tggtgtccgt gctgaccgtg ctgcaccagg actggctgaa cggcaaggag     960
tacaagtgta aggtgtccaa caaggccctg ccagccccaa tcgaaaagac catcagcaag    1020
gccaagggcc agccaagaga gccccaggtg tacaccctgc acccagcag ggaggagatg    1080
accaagaacc aggtgtccct gacctgtctg gtgaagggct tctacccaag cgacatcgcc    1140
gtggagtggg agagcaacgg ccagcccgag aacaactaca agaccacccc cccagtgctg    1200
gacagcgacg gcagcttctt cctgtacagc aagctgaccg tggacaagag cagatggcag    1260
cagggcaacg tgttcagctg ctccgtgatg cacgaggccc tgcacaacca ctacacccag    1320
aagagcctga gcctgtcccc caggcaag                                      1347
```

<210> SEQ ID NO 100
<211> LENGTH: 1338
<212> TYPE: DNA
<213> ORGANISM: Artificial sequence
<220> FEATURE:
<223> OTHER INFORMATION: Chimeric anti-CD151 antibody heavy chain derived from the murine 214B2 monoclonal antibody

<400> SEQUENCE: 100

```
caggtgcagc tgcagcagcc cggcagcgtg ctggtgagac ctggcgcctc cgtgaagctg      60
tcctgcaagg cctccggcta caccttcacc agcagcagca tgcactgggc caagcagcgg     120
ccaggccagg gactggaatg gatcggcgag atccacccca cagcggcaa caccaacaac      180
aacgagaagt tcaagggcaa ggccaccctg accgtggaca ccagcagctc caccgcctac     240
gtggacctga gcagcctgtc cagcgaggac agcgccgtgt actactgcgc cagagccaga     300
tccttctact acgctatgga ctgctggggc cagggcacca gcgtgaccgt gtccagcgcc     360
```

```
agcaccaagg gcccaagcgt gttccccctg gcccctgct ccagaagcac cagcgagagc    420
acagccgccc tgggctgcct ggtgaaggac tacttccccg agcccgtgac cgtgtcctgg    480
aacagcggag ccctgaccag cggcgtgcac accttccccg ccgtgctgca gagcagcggc    540
ctgtacagcc tgagcagcgt ggtgaccgtg cccagcagca gcctgggcac caagacctac    600
acctgtaacg tggaccacaa gcccagcaac accaaggtgg acaagagggt ggagagcaag    660 tacgcccac cctgccccag ctgcccagcc ccgagttcc tgggcggacc cagcgtgttc    720
ctgttccccc caagcccaa ggacaccctg atgatcagca gaacccccga ggtgacctgt    780
gtggtggtgg acgtgtccca ggaggacccc gaggtccagt tcaactggta cgtggacggc    840
gtggaggtgc acaacgccaa gaccaagccc agagaggagc agtttaacag cacctaccgg    900
gtggtgtccg tgctgaccgt gctgcaccag gactggctga acggcaaaga gtacaagtgt    960
aaggtctcca acaagggcct gccaagcagc atcgaaaaga ccatcagcaa ggccaagggc   1020
cagcctagag agccccaggt ctacaccctg ccacccagcc aagaggagat gaccaagaac   1080
caggtgtccc tgacctgtct ggtgaagggc ttctacccaa gcgacatcgc cgtggagtgg   1140
gagagcaacg gccagcccga gaacaactac aagaccaccc cccagtgct ggacagcgac   1200 ggcagcttct tcctgtacag caggctgacc gtggacaagt ccagatggca ggagggcaac   1260
gtctttagct gctccgtgat gcacgaggcc ctgcacaacc actacaccca gaagagcctg   1320
agcctgtccc tgggcaag                                                  1338
```

<210> SEQ ID NO 101
<211> LENGTH: 218
<212> TYPE: PRT
<213> ORGANISM: Artificial sequence
<220> FEATURE:
<223> OTHER INFORMATION: Chimeric anti-CD151 antibody light chain
      derived from the murine 203B6 monoclonal antibody

<400> SEQUENCE: 101

```
Asp Ile Val Leu Ser Gln Ser Pro Ala Ser Leu Ala Leu Ser Leu Gly
1               5                   10                  15

Gln Arg Ala Thr Ile Ser Cys Arg Ala Ser Ala Ser Val Glu Tyr Tyr
            20                  25                  30

Gly Thr Ser Leu Met His Trp Tyr Gln Gln Lys Pro Gly Gln Pro Pro
        35                  40                  45

Lys Leu Leu Ile Tyr Glu Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Leu Ala Ile Tyr Phe Cys Gln Gln Ser Arg
                85                  90                  95

Lys Ala Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 102
<211> LENGTH: 448
<212> TYPE: PRT
<213> ORGANISM: Artificial sequence
<220> FEATURE:
<223> OTHER INFORMATION: Chimeric anti-CD151 antibody heavy chain
      derived from the murine 203B6 monoclonal antibody

<400> SEQUENCE: 102

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Lys Ser Glu Asp Thr Ala Met Tyr Tyr Cys
                85                  90                  95

Ala Thr Pro Arg Ile Gly Thr Gly Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 103
<211> LENGTH: 445
<212> TYPE: PRT
<213> ORGANISM: Artificial sequence
<220> FEATURE:
<223> OTHER INFORMATION: Chimeric anti-CD151 antibody heavy chain
      derived from the murine 203B6 monoclonal antibody

<400> SEQUENCE: 103

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Lys Ser Glu Asp Thr Ala Met Tyr Tyr Cys
                85                  90                  95

Ala Thr Pro Arg Ile Gly Thr Gly Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 104
<211> LENGTH: 654
<212> TYPE: DNA
<213> ORGANISM: Artificial sequence
<220> FEATURE:
<223> OTHER INFORMATION: Chimeric anti-CD151 antibody light chain
      derived from the murine 203B6 monoclonal antibody

<400> SEQUENCE: 104
gacatcgtgc tgtcccagag ccccgcctct ctggccctga gcctgggaca gcgggccacc        60
atctcttgcc gggccagcgc cagcgtggag tactacggca ccagcctgat gcactggtat       120
cagcagaagc ccggccagcc ccccaagctg ctgatctacg aggccagcaa cgtggagagc       180
ggcgtgcccg ccagattcag cggcagcggc tccggcaccg acttcagcct gaacatccac       240
cccgtggaag aggacgacct ggccatctac ttttgccagc agagccggaa ggccccctac       300
acctttggcg gcggaacaaa gctggaaatc aagcgtacgg tggccgctcc cagcgtgttc       360
atcttccccc caagcgacga gcagctgaag agcggcaccg ccagcgtggt gtgtctgctg       420
aacaacttct accccaggga ggccaaggtg cagtggaagg tggacaacgc cctgcagagc       480
ggcaacagcc aggagagcgt caccgagcag gacagcaagg actccaccta cagcctgagc       540
agcaccctga ccctgagcaa ggccgactac gagaagcaca aggtgtacgc ctgtgaggtg       600
acccaccagg gcctgtccag ccccgtgacc aagagcttca caggggcga gtgc              654

<210> SEQ ID NO 105
<211> LENGTH: 1344
<212> TYPE: DNA
<213> ORGANISM: Artificial sequence
<220> FEATURE:
<223> OTHER INFORMATION: Chimeric anti-CD151 antibody heavy chain
      derived from the murine 203B6 monoclonal antibody

<400> SEQUENCE: 105

```
gaagtgaaac tggtggagtc tggcggcgga ctggtgcagc caggcggcag cctgaagctg      60
tcctgcgccg ccagcggctt caccttcagc acctacacca tgagctgggt gcgccagacc     120
cccgagaagc ggctggaatg ggtggcctac atcagcagcg gcggagggac cacctactac     180
cccgacaccg tgaagggccg gttcaccatc agccgggaca acgcccggaa caccctgtac     240
ctgcagatga acagcctgaa gtccgaggac accgccatgt actactgcgc cacccccggg     300
atcggcaccg gcttcgccta ctggggccag ggcaccctgg tgaccgtgtc cgccgccagc     360
accaagggcc caagcgtgtt cccgctagcc ccagcagca agagcaccag cggcggcaca     420
gccgccctgg gctgcctggt gaaggactac ttccccgagc ccgtgaccgt gtcctggaac     480
agcggagccc tgacctccgg cgtgcacacc ttccccgccg tgctgcagag cagcggcctg     540
tacagcctga gcgcgtggt gaccgtgccc agcagcagcc tgggcaccca gacctacatc     600
tgtaacgtga accacaagcc cagcaacacc aaggtggaca gagagtgga gcccaagagc     660 tgtgacaaga cccacacctg cccccccctgc ccagcccccg agctgctggg cggacccagc     720
gtgttcctgt tccccccaa gcccaaggac accctgatga tcagcagaac ccccgaggtg     780
acctgtgtgg tggtggacgt gtcccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaggagtac     960
aagtgtaagg tgtccaacaa ggccctgcca gccccaatcg aaaagaccat cagcaaggcc    1020
aagggccagc caagagagcc ccaggtgtac accctgccac ccagcaggga ggagatgacc    1080
aagaaccagg tgtccctgac ctgtctggtg aagggcttct acccaagcga catcgccgtg    1140
gagtgggaga gcaacggcca gcccgagaac aactacaaga ccaccccccc agtgctggac    1200
agcgacggca gcttcttcct gtacagcaag ctgaccgtgg acaagagcag atggcagcag    1260
ggcaacgtgt tcagctgctc cgtgatgcac gaggccctgc acaaccacta cacccagaag    1320
agcctgagcc tgtccccagg caag                                           1344
```

<210> SEQ ID NO 106  
<211> LENGTH: 1335  
<212> TYPE: DNA  
<213> ORGANISM: Artificial sequence  
<220> FEATURE:  
<223> OTHER INFORMATION: Chimeric anti-CD151 antibody heavy chain derived from the murine 203B6 monoclonal antibody

<400> SEQUENCE: 106

```
gaagtgaaac tggtggagtc tggcggcgga ctggtgcagc caggcggcag cctgaagctg      60
tcctgcgccg ccagcggctt caccttcagc acctacacca tgagctgggt gcgccagacc     120
cccgagaagc ggctggaatg ggtggcctac atcagcagcg gcggagggac cacctactac     180
cccgacaccg tgaagggccg gttcaccatc agccgggaca acgcccggaa caccctgtac     240
ctgcagatga acagcctgaa gtccgaggac accgccatgt actactgcgc cacccccggg     300
atcggcaccg gcttcgccta ctggggccag ggcaccctgg tgaccgtgtc cgccgccagc     360
accaagggcc caagcgtgtt cccctggcc cctgctcca gaagcaccag cgagagcaca     420
gccgccctgg gctgcctggt gaaggactac ttccccgagc ccgtgaccgt gtcctggaac     480
agcggagccc tgaccagcgg cgtgcacacc ttccccgccg tgctgcagag cagcggcctg     540
tacagcctga gcgcgtggt gaccgtgccc agcagcagcc tgggcaccaa gacctacacc     600
tgtaacgtgg accacaagcc cagcaacacc aaggtggaca gagggtgga gagcaagtac     660
```

```
ggcccaccct gccccagctg cccagccccc gagttcctgg gcggaccag cgtgttcctg       720 ttccccccca agcccaagga caccctgatg atcagcagaa cccccgaggt gacctgtgtg       780
gtggtggacg tgtcccagga ggaccccgag gtccagttca actggtacgt ggacggcgtg       840
gaggtgcaca acgccaagac caagcccaga gaggagcagt taacagcac ctaccgggtg       900 gtgtccgtgc tgaccgtgct gcaccaggac tggctgaacg gcaaagagta caagtgtaag       960
gtctccaaca agggcctgcc aagcagcatc gaaaagacca tcagcaaggc caagggccag      1020
cctagagagc cccaggtcta caccctgcca cccagccaag aggagatgac caagaaccag      1080
gtgtccctga cctgtctggt gaagggcttc tacccaagcg acatcgccgt ggagtgggag      1140
agcaacggcc agcccgagaa caactacaag accaccccc cagtgctgga cagcgacggc      1200
agcttcttcc tgtacagcag gctgaccgtg gacaagtcca gatggcagga gggcaacgtc      1260
tttagctgct ccgtgatgca cgaggccctg cacaaccact acacccagaa gagcctgagc      1320
ctgtccctgg gcaag                                                      1335

<210> SEQ ID NO 107
<211> LENGTH: 759
<212> TYPE: DNA
<213> ORGANISM: homo sapiens

<400> SEQUENCE: 107
atgggtgagt tcaacgagaa gaagacaaca tgtggcaccg tttgcctcaa gtacctgctg        60
tttacctaca attgctgctt ctggctggct ggcctggctg tcatggcagt gggcatctgg       120
acgctggccc tcaagagtga ctacatcagc ctgctggcct caggcaccta cctggccaca       180
gcctacatcc tggtggtggc gggcactgtc gtcatggtga ctggggtctt gggctgctgc       240
gccaccttca aggagcgtcg gaacctgctg cgcctgtact tcatcctgct cctcatcatc       300
tttctgctgg agatcatcgc tggtatcctc gcctacgcct actaccagca gctgaacacg       360
gagctcaagg agaacctgaa ggacaccatg accaagcgct accaccagcc gggccatgag       420
gctgtgacca cgctgtgga ccagctgcag caggagttcc actgctgtgg cagcaacaac       480
tcacaggact ggcgagacag tgagtggatc cgctcacagg aggccggtgg ccgtgtggtc       540
ccagacagct gctgcaagac ggtggtggct ctttgtgggc agcgagacca tgcctccaac       600
atctacaagg tggagggcgg ctgcatcacc aagttggaga ccttcatcca ggagcacctg       660
agggtcattg ggctgtggg gatcggcatt gcctgtgtgc aggtctttgg catgatcttc       720
acgtgctgcc tgtacaggag tctcaagctg gagcactac                             759

<210> SEQ ID NO 108
<211> LENGTH: 253
<212> TYPE: PRT
<213> ORGANISM: homo sapiens

<400> SEQUENCE: 108

Met Gly Glu Phe Asn Glu Lys Lys Thr Thr Cys Gly Thr Val Cys Leu
1               5                   10                  15

Lys Tyr Leu Leu Phe Thr Tyr Asn Cys Cys Phe Trp Leu Ala Gly Leu
            20                  25                  30

Ala Val Met Ala Val Gly Ile Trp Thr Leu Ala Leu Lys Ser Asp Tyr
        35                  40                  45

Ile Ser Leu Leu Ala Ser Gly Thr Tyr Leu Ala Thr Ala Tyr Ile Leu
    50                  55                  60

Val Val Ala Gly Thr Val Val Met Val Thr Gly Val Leu Gly Cys Cys
65                  70                  75                  80
```

```
Ala Thr Phe Lys Glu Arg Arg Asn Leu Leu Arg Leu Tyr Phe Ile Leu
                 85                  90                  95

Leu Leu Ile Ile Phe Leu Leu Glu Ile Ala Gly Ile Leu Ala Tyr
            100                 105                 110

Ala Tyr Tyr Gln Gln Leu Asn Thr Glu Leu Lys Glu Asn Leu Lys Asp
                115                 120                 125

Thr Met Thr Lys Arg Tyr His Gln Pro Gly His Glu Ala Val Thr Ser
        130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175

Gly Arg Val Val Pro Asp Ser Cys Cys Lys Thr Val Val Ala Leu Cys
            180                 185                 190

Gly Gln Arg Asp His Ala Ser Asn Ile Tyr Lys Val Glu Gly Gly Cys
                195                 200                 205

Ile Thr Lys Leu Glu Thr Phe Ile Gln Glu His Leu Arg Val Ile Gly
            210                 215                 220

Ala Val Gly Ile Gly Ile Ala Cys Val Gln Val Phe Gly Met Ile Phe
225                 230                 235                 240

Thr Cys Cys Leu Tyr Arg Ser Leu Lys Leu Glu His Tyr
                245                 250

<210> SEQ ID NO 109
<211> LENGTH: 95
<212> TYPE: PRT
<213> ORGANISM: mus musculus

<400> SEQUENCE: 109

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro
                85                  90                  95

<210> SEQ ID NO 110
<211> LENGTH: 12
<212> TYPE: PRT
<213> ORGANISM: mus musculus

<400> SEQUENCE: 110

Tyr Thr Phe Gly Gly Gly Thr Lys Leu Glu Ile Lys
1               5                   10

<210> SEQ ID NO 111
<211> LENGTH: 98
<212> TYPE: PRT
<213> ORGANISM: mus musculus

<400> SEQUENCE: 111

Gln Val Gln Leu Gln Gln Pro Gly Ser Val Leu Val Arg Pro Gly Ala
```

-continued

```
                1               5                  10                 15
Ser Val Lys Leu Ser Cys Lys Ala Ser Gly Tyr Thr Phe Thr Ser Ser
                    20                 25                 30

Trp Met His Trp Ala Lys Gln Arg Pro Gly Gln Gly Leu Glu Trp Ile
            35                 40                 45

Gly Glu Ile His Pro Asn Ser Gly Asn Thr Asn Tyr Asn Glu Lys Phe
        50                 55                 60

Lys Gly Lys Ala Thr Leu Thr Val Asp Thr Ser Ser Thr Ala Tyr
65                  70                 75                 80

Val Asp Leu Ser Ser Pro Thr Ser Glu Asp Ser Ala Val Tyr Tyr Cys
                    85                 90                 95

Ala Arg
```

<210> SEQ ID NO 112
<211> LENGTH: 17
<212> TYPE: PRT
<213> ORGANISM: mus musculus

<400> SEQUENCE: 112

```
Tyr Tyr Ala Met Asp Tyr Trp Gly Gln Gly Thr Ser Val Thr Val Ser
1               5                  10                 15

Ser
```

<210> SEQ ID NO 113
<211> LENGTH: 88
<212> TYPE: PRT
<213> ORGANISM: mus musculus

<400> SEQUENCE: 113

```
Asn Ile Val Met Thr Gln Ser Pro Lys Ser Met Ser Met Ser Val Gly
1               5                  10                 15

Glu Arg Val Thr Leu Ser Cys Lys Ala Ser Glu Asn Val Gly Thr Tyr
                    20                 25                 30

Val Ser Trp Tyr Gln Gln Lys Pro Glu Gln Ser Pro Lys Leu Leu Ile
            35                 40                 45

Tyr Gly Ala Ser Asn Arg Tyr Thr Gly Val Pro Asp Arg Phe Thr Gly
        50                 55                 60

Ser Gly Ser Ala Thr Asp Phe Thr Leu Thr Ile Ser Ser Val Gln Ala
65                  70                 75                 80

Glu Asp Leu Ala Asp Tyr His Cys
                    85
```

<210> SEQ ID NO 114
<211> LENGTH: 89
<212> TYPE: PRT
<213> ORGANISM: homo sapiens

<400> SEQUENCE: 114

```
Glu Ile Val Met Thr Gln Ser Pro Thr Leu Ser Leu Ser Pro Gly
1               5                  10                 15

Glu Arg Val Thr Leu Ser Cys Arg Ala Ser Gln Ser Val Ser Ser Ser
                    20                 25                 30

Tyr Leu Ser Trp Tyr Gln Gln Lys Pro Gly Gln Ala Pro Arg Leu Leu
            35                 40                 45

Ile Tyr Gly Ala Ser Thr Arg Ala Thr Gly Ile Pro Ala Arg Phe Ser
        50                 55                 60

Gly Ser Gly Ser Gly Thr Asp Phe Thr Leu Thr Ile Ser Ser Leu Gln
65                  70                 75                 80
```

```
Pro Glu Asp Phe Ala Val Tyr Tyr Cys
                85

<210> SEQ ID NO 115
<211> LENGTH: 88
<212> TYPE: PRT
<213> ORGANISM: homo sapiens

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 116
<211> LENGTH: 12
<212> TYPE: PRT
<213> ORGANISM: homo sapiens

<400> SEQUENCE: 116

Tyr Thr Phe Gly Gln Gly Thr Lys Leu Glu Ile Lys
1               5                   10

<210> SEQ ID NO 117
<211> LENGTH: 96
<212> TYPE: PRT
<213> ORGANISM: homo sapiens

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

<210> SEQ ID NO 118
<211> LENGTH: 96
<212> TYPE: PRT
<213> ORGANISM: homo sapiens

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<210> SEQ ID NO 119
<211> LENGTH: 17
<212> TYPE: PRT
<213> ORGANISM: homo sapiens

<400> SEQUENCE: 119

Tyr Tyr Gly Met Asp Val Trp Gly Gln Gly Thr Thr Val Thr Val Ser
1               5                   10                  15

Ser
```